(12) United States Patent  
Yamanaka et al.

(10) Patent No.: US 9,499,797 B2  
(45) Date of Patent: Nov. 22, 2016

(54) METHOD OF MAKING INDUCED PLURIPOTENT STEM CELLS

(75) Inventors: Shinya Yamanaka, Kyoto (JP); Keisuke Okita, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 13/572,593

(22) Filed: Aug. 10, 2012

(65) Prior Publication Data

US 2013/0065311 A1    Mar. 14, 2013

Related U.S. Application Data

(62) Division of application No. 12/733,118, filed as application No. PCT/JP2009/058873 on May 1, 2009, now abandoned.

(60) Provisional application No. 61/071,508, filed on May 2, 2008, provisional application No. 61/136,246, filed on Aug. 21, 2008, provisional application No. 61/136,615, filed on Sep. 19, 2008, provisional application No. 61/193,363, filed on Nov. 21, 2008.

(51) Int. Cl.
| | |
|---|---|
| *C12N 15/00* | (2006.01) |
| *C12N 5/074* | (2010.01) |
| *C12N 15/79* | (2006.01) |

(52) U.S. Cl.
CPC ............ *C12N 5/0696* (2013.01); *C12N 15/79* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2506/02* (2013.01); *C12N 2506/13* (2013.01); *C12N 2506/1307* (2013.01); *C12N 2506/1361* (2013.01); *C12N 2510/00* (2013.01)

(58) Field of Classification Search
USPC .................................................. 435/325, 455
See application file for complete search history.

(56) References Cited

U.S. PATENT DOCUMENTS

| | | |
|---|---|---|
| 4,650,764 A | 3/1987 | Temin et al. |
| 4,861,719 A | 8/1989 | Miller |
| 4,937,190 A | 6/1990 | Palmenberg et al. |
| 5,225,348 A | 7/1993 | Nagata et al. |
| 5,266,491 A | 11/1993 | Nagata et al. |
| 5,268,290 A | 12/1993 | Hasegawa et al. |
| 5,288,514 A | 2/1994 | Ellman |
| 5,324,645 A | 6/1994 | Takahara et al. |
| 5,449,614 A | 9/1995 | Danos et al. |
| 5,519,134 A | 5/1996 | Acevedo et al. |
| 5,525,735 A | 6/1996 | Gallop et al. |
| 5,549,974 A | 8/1996 | Holmes |
| 5,591,624 A | 1/1997 | Barber et al. |
| 5,637,456 A | 6/1997 | Roth et al. |
| 5,652,122 A | 7/1997 | Frankel et al. |
| 5,674,980 A | 10/1997 | Frankel |
| 5,707,618 A | 1/1998 | Armentano et al. |
| 5,716,832 A | 2/1998 | Barber et al. |
| 5,744,320 A | 4/1998 | Sherf et al. |
| 5,817,491 A | 10/1998 | Yee et al. |
| 5,817,492 A | 10/1998 | Saito et al. |
| 5,830,725 A | 11/1998 | Nolan et al. |
| 5,834,256 A | 11/1998 | Finer et al. |
| 5,858,740 A | 1/1999 | Finer et al. |
| 5,910,434 A | 6/1999 | Rigg et al. |
| 5,955,331 A | 9/1999 | Danos et al. |
| 6,013,517 A | 1/2000 | Respess et al. |
| 6,017,735 A | 1/2000 | O'Hare |
| 6,017,761 A | 1/2000 | Rigg et al. |
| 6,025,192 A | 2/2000 | Beach et al. |
| 6,140,111 A | 10/2000 | Riviere et al. |
| 6,146,874 A | 11/2000 | Zolotukhin et al. |
| 6,153,432 A | 11/2000 | Halvorsen et al. |
| 6,153,745 A | 11/2000 | Williams et al. |
| 6,203,975 B1 | 3/2001 | Wilson et al. |
| 6,251,398 B1 | 6/2001 | O'Hare et al. |
| 6,255,071 B1 | 7/2001 | Beach et al. |
| 6,312,948 B1 | 11/2001 | Cohen-Haguenauer |
| 6,312,949 B1 | 11/2001 | Sakurada et al. |
| 6,333,195 B1 | 12/2001 | Respess et al. |
| 6,365,352 B1 | 4/2002 | Yerramilli et al. |
| 6,395,546 B1 | 5/2002 | Zobel et al. |
| 6,451,595 B1 | 9/2002 | Kim et al. |
| 6,485,959 B1 | 11/2002 | Demetriou et al. |

(Continued)

FOREIGN PATENT DOCUMENTS

| | | |
|---|---|---|
| AU | 2008201280 A1 | 4/2008 |
| CN | 101250502 A | 8/2008 |

(Continued)

OTHER PUBLICATIONS

Takahashi (Cell, Aug. 25, 2006, vol. 126, p. 663-676).*
Maherali (Cell Stem Cell, Jul. 2007, vol. 1, p. 55-70).*
Blelloch (Cell Stem Cell, Sep. 2007, vol. 1, p. 245-247).*
Yu (Science, Dec. 2007, vol. 318, p. 1917-1920).*
Nakagawa (Nat Biotechnol, Jan. 2008 (published online Nov. 30, 2007), vol. 26: 101-106).*
Wernig (Cell Stem Cell, Jan. 2008, vol. 2:10-12).*
Duinsbergen (Experimental Cell Res. Jul. 9, 2008, vol. 314, p. 3255-3263).*
Eminli (Stem Cells, Jul. 17, 2008, vol. 26, p. 2467-2474).*
Okita (Science, Nov. 7, 2008, vol. 322, p. 949-953).*
Kaji (Nature, Apr. 9, 2009, vol. 458, p. 771-776).*
Aoi (Science, Aug. 2008, vol. 321, p. 699-702; published online Feb. 14, 2008).*
Feng (Cell Stem Cell, Apr. 3, 2009, vol. 4, p. 301-312).*
Kanai-Azuma (Development, 2002, vol. 129, p. 2367-2379).*

(Continued)

*Primary Examiner* — Michael Wilson
(74) *Attorney, Agent, or Firm* — Knobbe, Martens, Olson & Bear, LLP

(57) ABSTRACT

A method of producing an induced pluripotent stem cell includes introducing into a somatic cell one or more non-viral expression vectors. The vectors include one or more of an Oct family gene, a Klf family gene, a Sox family gene, a Myc family gene, a Lin family gene, and Nanog gene. The somatic cell is then cultured in a medium that supports pluripotent stem cells. At least a portion of the one or more introduced non-viral expression vectors is not substantially integrated in the chromosome.

9 Claims, 16 Drawing Sheets

(56) References Cited

U.S. PATENT DOCUMENTS

| | | | |
|---|---|---|---|
| 6,521,453 B1 | 2/2003 | Crameri et al. | |
| 6,521,455 B2 | 2/2003 | O'Hare et al. | |
| 6,605,275 B1 | 8/2003 | Boyse et al. | |
| 6,660,514 B1 | 12/2003 | Zolotukhin et al. | |
| 6,773,920 B1 | 8/2004 | Dalby et al. | |
| 6,833,269 B2 | 12/2004 | Carpenter | |
| 6,835,567 B1 | 12/2004 | Sah et al. | |
| 6,841,535 B2 | 1/2005 | Divita et al. | |
| 6,872,528 B2 | 3/2005 | Klatzmann et al. | |
| 6,875,578 B2 | 4/2005 | Giuliano et al. | |
| 6,881,825 B1 | 4/2005 | Robbins et al. | |
| 6,910,434 B2 | 6/2005 | Lundgren et al. | |
| 6,995,009 B1 | 2/2006 | Kitamura et al. | |
| 7,029,913 B2 | 4/2006 | Thomson | |
| 7,030,292 B2 | 4/2006 | Yan et al. | |
| 7,070,994 B2 | 7/2006 | Barber et al. | |
| 7,250,255 B2 | 7/2007 | Yamanaka | |
| 7,439,064 B2 | 10/2008 | Thomson et al. | |
| 8,048,999 B2 | 11/2011 | Yamanaka et al. | |
| 8,058,065 B2 * | 11/2011 | Yamanaka et al. | 435/377 |
| 8,129,187 B2 * | 3/2012 | Yamanaka et al. | 435/377 |
| 8,211,697 B2 | 7/2012 | Sakurada et al. | |
| 8,278,104 B2 * | 10/2012 | Yamanaka et al. | 435/377 |
| 8,298,825 B1 * | 10/2012 | Hochedlinger et al. | 435/377 |
| 8,440,461 B2 * | 5/2013 | Thomson | C12N 5/0696 435/377 |
| 2002/0090722 A1 | 7/2002 | Dominko et al. | |
| 2002/0123146 A1 | 9/2002 | Klatzmann et al. | |
| 2002/0174013 A1 | 11/2002 | Freeman et al. | |
| 2003/0003574 A1 | 1/2003 | Toma et al. | |
| 2003/0044976 A1 | 3/2003 | Dominko et al. | |
| 2003/0161817 A1 | 8/2003 | Young et al. | |
| 2004/0048297 A1 | 3/2004 | Scherf | |
| 2004/0137460 A1 | 7/2004 | Yamanaka et al. | |
| 2004/0235031 A1 * | 11/2004 | Schultz | C12N 15/1136 435/6.16 |
| 2005/0019801 A1 | 1/2005 | Rubin et al. | |
| 2005/0026133 A1 | 2/2005 | Nakatsuji et al. | |
| 2005/0079606 A1 | 4/2005 | Tamaki et al. | |
| 2005/0130144 A1 | 6/2005 | Nakatsuji et al. | |
| 2005/0162419 A1 | 7/2005 | Kim et al. | |
| 2006/0030041 A1 | 2/2006 | Furcht et al. | |
| 2006/0084172 A1 | 4/2006 | Muller et al. | |
| 2006/0088599 A1 | 4/2006 | Prasad et al. | |
| 2006/0095319 A1 | 5/2006 | Cardwell | |
| 2006/0110830 A1 | 5/2006 | Dominko et al. | |
| 2006/0222636 A1 | 10/2006 | Rambukkana | |
| 2006/0246064 A1 * | 11/2006 | Boyle | C07K 14/70578 424/143.1 |
| 2006/0292620 A1 | 12/2006 | Yamanaka et al. | |
| 2007/0033061 A1 | 2/2007 | Patten et al. | |
| 2007/0053884 A1 | 3/2007 | Suda et al. | |
| 2007/0155013 A1 | 7/2007 | Akaike et al. | |
| 2007/0202592 A1 | 8/2007 | Kitagawa et al. | |
| 2007/0254884 A1 | 11/2007 | Chen et al. | |
| 2007/0269790 A1 | 11/2007 | Amit et al. | |
| 2008/0003560 A1 | 1/2008 | Nakatsuji et al. | |
| 2008/0076176 A1 | 3/2008 | Dominko et al. | |
| 2008/0085555 A1 | 4/2008 | Asahara et al. | |
| 2008/0132803 A1 | 6/2008 | Friedlander | |
| 2008/0171358 A1 | 7/2008 | Perrault | |
| 2008/0171385 A1 | 7/2008 | Bergendahl et al. | |
| 2008/0206865 A1 | 8/2008 | Zhang et al. | |
| 2008/0233610 A1 | 9/2008 | Thomson et al. | |
| 2008/0274914 A1 | 11/2008 | Yamanaka | |
| 2008/0280362 A1 | 11/2008 | Jaenisch et al. | |
| 2008/0293143 A1 | 11/2008 | Lin et al. | |
| 2008/0299548 A1 | 12/2008 | Yamanaka | |
| 2009/0047263 A1 | 2/2009 | Yamanaka et al. | |
| 2009/0068742 A1 | 3/2009 | Yamanaka | |
| 2009/0191159 A1 | 7/2009 | Sakurada et al. | |
| 2009/0191171 A1 | 7/2009 | Ma | |
| 2009/0227032 A1 | 9/2009 | Yamanaka et al. | |
| 2009/0246875 A1 | 10/2009 | Yamanaka et al. | |
| 2009/0299763 A1 | 12/2009 | Sakurada | |
| 2009/0304646 A1 | 12/2009 | Sakurada et al. | |
| 2009/0324559 A1 | 12/2009 | Sakurada | |
| 2010/0003757 A1 | 1/2010 | Mack | |
| 2010/0021437 A1 | 1/2010 | Isacson | |
| 2010/0062533 A1 | 3/2010 | Yamanaka | |
| 2010/0062534 A1 | 3/2010 | Hochedlinger | |
| 2010/0075421 A1 | 3/2010 | Yamanaka | |
| 2010/0093090 A1 | 4/2010 | Deng | |
| 2010/0105100 A1 | 4/2010 | Sakurada | |
| 2010/0120069 A1 | 5/2010 | Sakurada | |
| 2010/0144031 A1 | 6/2010 | Jaenisch | |
| 2010/0184051 A1 | 7/2010 | Hochedlinger | |
| 2010/0184227 A1 | 7/2010 | Thomson | |
| 2010/0210014 A1 | 8/2010 | Yamanaka | |
| 2010/0216236 A1 | 8/2010 | Yamanaka | |
| 2010/0221827 A1 | 9/2010 | Jaenisch | |
| 2010/0233804 A1 | 9/2010 | Zhou | |
| 2010/0240090 A1 | 9/2010 | Sakurada | |
| 2010/0267135 A1 | 10/2010 | Sakurada | |
| 2010/0279404 A1 | 11/2010 | Yamanaka | |
| 2011/0014164 A1 | 1/2011 | Huangfu et al. | |
| 2011/0039332 A1 | 2/2011 | Sakurada | |
| 2013/0059386 A1 | 3/2013 | Yamanaka et al. | |
| 2014/0057355 A1 * | 2/2014 | Thomson | C12N 5/0696 435/461 |
| 2014/0206083 A1 | 7/2014 | Sakurada et al. | |
| 2015/0072417 A1 | 3/2015 | Yamanaka et al. | |

FOREIGN PATENT DOCUMENTS

| | | |
|---|---|---|
| CN | 101550428 A | 10/2009 |
| EP | 1384775 A1 | 1/2004 |
| EP | 1403366 A1 | 3/2004 |
| EP | 1970446 A1 | 9/2008 |
| EP | 2096169 A1 | 9/2009 |
| EP | 2213727 A1 | 4/2010 |
| JP | 2-227075 | 9/1990 |
| JP | 2002-065261 A | 3/2002 |
| JP | 2002-511248 A | 4/2002 |
| JP | 2003-009854 A | 1/2003 |
| JP | 2004-161682 A | 6/2004 |
| JP | 2005-095027 A | 4/2005 |
| JP | 2005-198546 | 7/2005 |
| JP | 2005-359537 | 12/2005 |
| JP | 2006-526409 | 11/2006 |
| JP | 2008-515435 | 5/2008 |
| JP | 2008-283972 A | 11/2008 |
| WO | WO 95/10619 A2 | 4/1995 |
| WO | WO 95/10619 A3 | 7/1995 |
| WO | WO 97/05265 A1 | 2/1997 |
| WO | WO 98/02529 A1 | 1/1998 |
| WO | WO 99/55841 A2 | 11/1999 |
| WO | WO 99/64568 A1 | 12/1999 |
| WO | WO 00/18885 A1 | 4/2000 |
| WO | WO 00/23567 A2 | 4/2000 |
| WO | WO 00/27995 A1 | 5/2000 |
| WO | WO 00/23567 A3 | 7/2000 |
| WO | WO 01/21767 A2 | 3/2001 |
| WO | WO 01/34776 A1 | 5/2001 |
| WO | WO 01/51616 A2 | 7/2001 |
| WO | WO 01/21767 A3 | 8/2001 |
| WO | WO 01/81549 A2 | 11/2001 |
| WO | WO 00/73423 A1 | 12/2001 |
| WO | WO 02/00871 A2 | 1/2002 |
| WO | WO 02/061033 A2 | 8/2002 |
| WO | WO 02/000871 A3 | 10/2002 |
| WO | WO 02/086129 A1 | 10/2002 |
| WO | WO 02/086134 A2 | 10/2002 |
| WO | WO 02/097090 A1 | 12/2002 |
| WO | WO 03/018780 A1 | 3/2003 |
| WO | WO 02/086134 A3 | 12/2003 |
| WO | WO 2004/081205 A1 | 9/2004 |
| WO | WO 2005/017149 | 2/2005 |
| WO | WO 2005/035741 A1 | 4/2005 |
| WO | WO 2005/080598 A1 | 9/2005 |
| WO | WO 2005/090557 A1 | 9/2005 |
| WO | WO 2006/035741 A1 | 4/2006 |
| WO | WO 2006/083331 | 8/2006 |
| WO | WO 2006/084229 A2 | 8/2006 |

(56) References Cited

FOREIGN PATENT DOCUMENTS

| | | |
|---|---|---|
| WO | WO 2006/088867 A2 | 8/2006 |
| WO | WO 2007/014162 | 2/2007 |
| WO | WO 2007/019398 A1 | 2/2007 |
| WO | WO 2007/026255 A2 | 3/2007 |
| WO | WO 2007/054720 A1 | 5/2007 |
| WO | WO 2007/069666 A1 | 6/2007 |
| WO | WO 2007/097494 A1 | 8/2007 |
| WO | WO 2008/030610 A2 | 3/2008 |
| WO | WO 2008/035110 A1 | 3/2008 |
| WO | WO 2008/038148 A2 | 4/2008 |
| WO | WO 2008/089351 A1 | 7/2008 |
| WO | WO 2008/105566 A1 | 9/2008 |
| WO | WO 2008/105630 A1 | 9/2008 |
| WO | WO 2008/116213 A1 | 9/2008 |
| WO | WO 2008/118820 A2 | 10/2008 |
| WO | WO 2008/124133 A1 | 10/2008 |
| WO | WO 2008/118820 A3 | 11/2008 |
| WO | WO 2008/150814 A2 | 12/2008 |
| WO | WO 2008/151058 A2 | 12/2008 |
| WO | WO 2008/151058 A3 | 1/2009 |
| WO | WO 2009/006930 A1 | 1/2009 |
| WO | WO 2009/006997 A1 | 1/2009 |
| WO | WO 2009/007852 A2 | 1/2009 |
| WO | WO 2008/150814 A3 | 2/2009 |
| WO | WO 2009/023161 A1 | 2/2009 |
| WO | WO 2009/032194 A1 | 3/2009 |
| WO | WO 2009/032456 A2 | 3/2009 |
| WO | WO 2009/032456 A3 | 4/2009 |
| WO | WO 2009/057831 A1 | 5/2009 |
| WO | WO 2009/061442 A1 | 5/2009 |
| WO | WO 2009/067563 A1 | 5/2009 |
| WO | WO 2009/007852 A3 | 8/2009 |
| WO | WO 2009/096614 A1 | 8/2009 |
| WO | WO 2009/102983 A2 | 8/2009 |
| WO | WO 2009/115295 A1 | 9/2009 |
| WO | WO 2009/133971 A1 | 11/2009 |
| WO | WO 2009/102983 A3 | 12/2009 |
| WO | WO 2009/144008 A1 | 12/2009 |
| WO | WO 2009/149233 A1 | 12/2009 |
| WO | WO 2010/013359 A1 | 2/2010 |
| WO | WO 2010/048567 A1 | 4/2010 |

OTHER PUBLICATIONS

Lee, Molecular and Cell. Biol., Oct. 2004, vol. 24, No. 19, p. 8428-8436.*
Klf1 description, Wikipedia, 2014.*
Klf2 description, Wikipedia, 2014.*
Okita (Nature, 2007, vol. 448, p. 313-317).*
$24 Million in New Stem Cell Research Funding Awarded to 25 California Institutions, California Institute for Regenerative Medicine, public release, Jun. 27, 2008, 4 pages.
A reprogramming rush, Editorial, Nature 452:388, Mar. 27, 2008. (Published online Mar. 26, 2008.).
Adachi, et al., Role of SOX2 in Maintaining Pluripotency of Human Embryonic Stem Cells, Genes Cells 15(5):455-70, May 2010.
Adhikary, et al., Transcriptional Regulation and Transformation by Myc Proteins, Nat. Rev. Mol. Cell Biol. 6(8):635-45, Aug. 2005.
Akimov, et al., Bypass of Senescence, Immortalization, and Transformation of Human Hematopoietic Progenitor Cells, Stem Cells 23:1423-33, 2005.
Alberts, et al., Molecular Biology of the Cell, Fourth Ed., Garland Science, 2002, p. 22.
Allergucci, et al., Differences Between Human Embryonic Stem Cell Lines, Hum. Reprod. Update 13(2):103-20, Mar.-Apr. 2007.
Altschul, et al., Gapped BLAST and PSI-BLAST: A New Generation of Protein Database Search Programs, Nucleic Acids Research 25(17): 3389-3402, 1997.
Amit, et al., Clonally Derived Human Embryonic Stem Cell Lines Maintain Pluripotency and Proliferative Potential for Prolonged Periods of Culture, Dev. Biol. 227:271-78, 2000.
Amsellem, et al., Ex Vivo Expansion of Human Hematopoietic Stem Cells by Direct Delivery of the HOXB4 Homeoprotein, Nat. Med. 9(11):1423-27, 2003.

Anderson, et al., Transgenic Enrichment of Cardiomyocytes From Human Embryonic Stem Cells, Mol. Ther. 15(11):2027-36, Nov. 2007.
Anisimov, et al., SAGE Identification of Gene Transcripts with Profiled Unique to Pluripotent Mouse R1 Embryonic Stem Cells, Genomics 79(2):69-176, Feb. 2002.
Aoi et al., Generation of Pluripotent Stem Cells from Adult Mouse Liver and Stomach Cells, Science, Feb. 14, 2008.
Asai, et al., Modulation of Tumor Immunogenicity of Rat Glioma Cells by s-Mys Expression: Eradication of Rat Gliomas in Vivo, Cell Growth & Differentiation 5(11):1153-1158, Nov. 1984.
Assady, et al., Insulin Production by Human Embryonic Stem Cells, Diabetes 50(8):1691-1697, Aug. 2001.
Assou, et al., A Meta-Analysis of Human Embryonic Stem Cells Transcriptome Integrated into a Web-Based Expression Atlas, Stem Cells 25(4):961-73, Apr. 2007.
Avilion, et al., Multipotent Cell Lineages in Early Mouse Development Depend on SOX2 Function, Genes Dev. 17:126-40, 2003.
Bader, et al., Leukemia Inhibitory Factor Modulates Cardiogenesis in Embryoid Bodies in Opposite Fashions, Circ. Res. 86(7):787-94, Apr. 14, 2000.
Bagutti, et al., Differentiation of Embryonal Stem Cells Into Keratinocytes: Comparison of Wild-Type and Beta 1 Integrin-Deficient Cells Dev. Biol. 179(1):184-96, Oct. 10, 1996.
Bambrink, et al., Sequential Expression of Pluripotency Markers During Direct Reprogramming of Mouse Somatic Cells, Cell Stem Cell 2(2)151-159, 2008.
Bang, et al., Deconstructing Pluripotency, Science 320:58-59, 2008.
Barrett, et al., Activation Domains of L-Myc and c-Myc Determine Their Transforming Potencies in Rat Embryo Cells, Mol. Cell. Biol. 12(7):3130-37, 1992.
Barrett, et al., NCBI GEO: Mining Tens of Millions of Expression Profiles-Database and Tools Update, Nucleic Acids Res. 35(Database issue):D760-S, Jan. 2007.
Bayani, et al., Multi-Color FISH techniques, Curr. Protoc. Cell Biol., Chapter 22, Unit 22.5, 2004.
Becker-Hapak, et al., Protein Transduction: Generation of Full-Length Transducible Proteins Using the TAT System, Curr. Protoc. Cell Biol., Chapter 20, Unit 20.2, May 2003.
Belmonte, et al., Induced Pluripotent Stem Cells and Reprogramming: Seeing the Science Through the Hype, Nat. Rev. Genet., 10(12):878-83, Dec. 2009 (Epub Oct. 27, 2009).
Bendall, et al., IGF and FGF Cooperatively Establish the Regulatory Stem Cell Niche of Pluripotent Human Cells in Vitro, Nature 448(7157):1015-21, Aug. 30, 2007.
Benetti, et al., A Mammalian microRNA Cluster Controls DNA Methylation and Telomere Recombination Via Rbl2-Dependent Regulation of DNA Methyltransferases, Nat. Struct. Mol. Biol. 15(3):268-79, published online Mar. 2, 2008.
Ben-Shushan, et al., Rex-1, A Gene Encoding a Transcription Factor Expressed in the Early Embryo, Is Regulated via Oct-3/4 and Oct-6 Binding to an Octomer Site and a Novel Protein, Rox-1, Binding to an Adjacent Site, Mol. Cell Biol. 18(4):1866-78, 1998.
Berg, et al., An argument Against a Role for Oct4 in Somatic Stem Cells, Cell Stem Cell 1(4):359-60, Oct. 11, 2007.
Bibel, et al., Differentiation of Mouse Embryonic Stem Cells Into a Defined Neuronal . Lineage, Nature Neuroscience 7:1003-1009, 2004.
Bigdeli, et al., Adaptation of Human Embryonic Stem Cells to Feeder-Free and Matrix-Free Culture Conditions Directly on Plastic Surfaces, J. Biotec. 133:146-153, 2008.
BioPorter™ Gene Therapy System, Inc., Wako Bio Window 40:7, 2002.
BioPorter™ Protein Delivery Reagent From www.biocarta.com, date unknown.
Birnbaum, et al., Slicing Across Kingdoms: Regeneration in Plants and Animals, Cell. 132(4):697-710, Feb. 22, 2008.
Birrer, et al., L-myc Cooperates With ras to Transform Primary Rat Embryo Fibroblasts, Mol. Cell. Biol. 8(6):2668-73, 1988.
Blackwood, et al., Max: A Helix-Loop-Helix Zipper Protein That Forms a Sequence-Specific DNA-Binding Complex With Myc, Science 251(499*):1211-17, 1991.

(56) References Cited

OTHER PUBLICATIONS

Blelloch, et al., Generation of Induced Pluripotent Stem Cells in the Absence of Drug Selection, Cell Stem Cell. 1(3):245-247, 2007.
Block, et al., Population Expansion, Clonal Growth, and Specific Differentiation Patterns in Primary Cultures of Hepatocytes Induced by HGF/SF, EGF and TGFα in a Chemically Defined (HGM) Medium, J. Cell Biol. 132(6):1133-49, 1996.
Blow, N., Stem Cells: In Search of Common Ground, Nature 451(7180):855-8, Feb. 14, 2008.
Bonetta, L., European Stem Cell Patents: Taking the Moral High Road? Cell 132(4):SI4-S16, Feb. 22, 2008.
Bongso, A., et al., Isolation and Culture of Inner Cell Mass Cells From Human Blastocysts, Human Reproduction 9(11):2110-2117, 1994.
Boquest, et al., Epigenetic Programming of Mesenchymal Stem Cells From Human Adipose Tissue, Stem Cell Rev. 2(4):319-29, 2006.
Bortvin, et al., Incomplete Reactivation of Oct4-Related Genes in Mouse Embryos Cloned From Somatic Nuclei, Development 130:1673-80, 2003.
Boyer, et al., Core Transcriptional Regulatory Circuitry in Human Embryonic Stem Cells, Cell. 122(6):947-956, 2005.
Brambrink, et al., Sequential Expression of Pluripotency Markers During Direct Reprogramming of Mouse Somatic Cells, Cell Stem Cell. 2:151-159, 2008.
Brena, et al., Quantitative Assessment of DNA Methylation: Potential Applications for Disease Diagnosis, Classification, and Prognosis in Clinical Settings, J. Mol. Med. 84(5):365-377, May 2006.
Brimble, et al., Karyotypic Stability, Genotyping, Differentiation, Feeder-Free Maintenance, and Gene Expression Sampling in Three Human Embryonic Stem Cell Lines Derived Prior to Aug. 9, 2001, Stem Cells Develop. 13:585-596, 2004.
Brough, et al., An Essential Domain of the c-Myc Protein Interacts With a Nuclear Factor That Is Also Required for E1A-Mediated Transformation, Mol. Cell. Biol. 15(3):1536-44, 1995.
Brüstle, et al., Embryonic Stem Cell-Derived Glial Precursors: A Source of Myelinating Transplants, Science. 285(5428):754-756, Jul. 30, 1999.
Burns, et al., Diabetes Mellitus: A Potential Target for Stem Cell Therapy, Curr. Stem Cell Res. Ther. 1(2):255-66, May 2006.
Buttery, et al., Differentiation of Osteoblasts and in Vitro Bone Formation From Murine Embryonic Stem Cells, Tissue Eng. 7(1):89-99, Feb. 2001.
Cai, et al., Directed Differentiation of Human Embryonic Stem Cells Into Functional Hepatic Cells, Hepatology. 45(5):1229-1239, May 2007.
Campbell, et al., Phosphonate Ester Synthesis Using a Modified Mitsunobu Condensation, J. Org. Chem.59:658-660, 1994.
Carey, et al., Reprogramming of Murine and Human Somatic Cells Using a Single Polycistronic Vector, Proc. Natl. Acad. Sci. USA 106(1):157-162, Jan. 6, 2009, Epub. Dec. 24, 2008; Erratum in: Proc. Natl. Acad. Sci. USA (13):5449, Mar. 31, 2009.
Carpenter, et al., Characterization and Differentiation of Human Embryonic Stem Cells, Cloning and Stem Cells 5(1) 169-176, Nov. 1, 2003.
Cartwright, et al., LIF/STAT3 Controls ES Cell Self-Renewal and Pluripotency by a Myc-Dependent Mechanism, Development. 132(5):885-896, Mar. 2005.
Catalog of ES Cell Culture Medium, Cosmo Bio News 49:5, 2005.
Cauffman, et al., Oct-4 mRNA and Protein Expression During Human Preimplantation Development, Molecular Human Reproduction 11(3) 173-180, Feb. 4, 2005.
Chadwick, et al., Cytokines and BMP-4 Promote Hematopoietic Differentiation of Human Embryonic Stem Cells, Blood 102(3):906-915, Aug. 1, 2003.
Chambers, et al., Functional Expression Cloning of Nanog, A Pluripotency Sustaining Factor in Embryonic Stem Cells, Cell 113:643-55, 2003.
Chang, et al., Embryonic Stem Cells/Induced Pluripotent Stem Cells, Stem Cells 27:1042-1049, 2009.
Chang, et al., The c-Myc Transactivation Domain is a Direct Modulator of Apoptotic Versus Proliferative Signals, Mol. Cell Biol. 20(12):4309-4319, Jun. 2000.
Check, E., Simple Recipe Gives Adult Cells Embryonic Powers, Nature 442:11, Jul. 6, 2006.
Chen, et al., Analogous Organic-Synthesis of Small-Compound Libraries—Validation of Combinatorial Chemistry in Small-Molecule Synthesis, Journal of the American Chemical Society. 116(6):2661-2662, 1994.
Chen, et al., From Stem Cells to Oligodendrocytes: Prospects for Brain Therapy, Stem Cell Rev. 3(4):280-288, Dec. 2007.
Cheng, et al., Mammalian Grb2 Regulates Multiple Steps in Embryonic Development and Malignant Transformation, Cell 95:793-803, 1998.
Chiba Medical Journal 84(1):1-7, Feb. 2006.
Childs, et al., Regression of Metastatic Renal-Cell Carcinoma After Nonmyeloablative Allogeneic Peripheral-Blood Stem-Cell Transplantation, N. Engl. J. Med. 343(11):750-758, Sep. 14, 2000.
Chin, et al., Induced Pluripotent Stem Cells and Embryonic Stem Cells are Distinguished by Gene Expression Signatures, Cell Stem Cell. 5(1):111-123, Jul. 2, 2009.
Cho, et al., An Unnatural Biopolymer, Science, 261(5126):1303-5, Sep. 3, 1993.
Cinalli, et al., Germ Cells Are Forever, Cell. 132(4):559-562, Feb. 22, 2008.
Clerc, et al., The B-cell-Specific Oct-2 Protein Contains POU box- and Homeo Box-Type Domains, Genes Dev. 2(12A):1570-1581, Dec. 1988.
Cline, et al., Randomize Gene Sequences with New PCR Mutagenesis Kit, Strategies Newsletter 13:157-161, 2000.
Cohen, et al., Ooplasmic Transfer in Mature Human Oocytes, Molecular Human Reproduction 4:269-280, 1998.
Correction printed in Nature 447:897, Jun. 21, 2007.
Coutts, et al., Stem Cells for the Treatment of Spinal Cord Injury, Exp. Neurol. 209(2):368-77, Feb. 2008.
Cowan, et al., Derivation of Embryonic Stem-Cell Lines From Human Blastocysts, N. Engl. J. Med. 350:1353-56, 2004.
Cowan, et al., Nuclear Reprogramming of Somatic Cells After Fusion with Human Embryonic Stem Cells, Science 309:1369-1374, 2005.
Cowling, et al., Mechanism of Transcriptional Activation by the Myc Oncoproteins, Semin. Cancer Biol. 16(4):242-252, Aug. 2006.
Crouch, D.H., et al., Multiple Phenotypes Associated With Myc-Induced Transformation of Chick Embryo Fibroblasts Can Be Dissociated by a Basic Region Mutation, Nucleic Acids Research 24(16):3216-3221, 1996.
Cyranoski, D., Stem Cells: 5 Things to Know Before Jumping on the iPS Bandwagon, Nature. 452(7186)406-408, 2008.
Cyranoski, et al., Simple Switch Turns Cells Embryonic, Nature 447:618-619, 2007.
Cyranoski, Japan Ramps Up Patent Effort to Keep iPS lead, Nature 453(7198):962-963, 2008.
Daley, et al., Broader Implications of Defining Standards for the Pluripotency of iPSCs, Cell Stem Cell. 4(3):200-201, Mar. 6, 2009; author reply p. 202.
Daley, et al., Prospects for Stem Cell Based Therapy, Cell 132(4):544-548, Feb. 22, 2008.
D'Amour, et al., Efficient Differentiation of Human Embryonic Stem Cells to Definitive Endoderm, Nat Biotechnol. 23(12):1534-1541, Dec. 2005.
D'Amour, et al., Production of Pancreatic Hormone-Expressing Endocrine Cells From Human Embryonic Stem Cells, Nat. Biotechnol. 24(11): 1392-1401, Nov. 2006.
Dang, et al., the Biology of the Mammalian Kruppel-Like Family of Transcription Factors, Int. J. Biochem. Cell Biol. 32:1103-21, 2000.
Dani, et al., Differentiation of Embryonic Stem Cells Into Adipocytes in Vitro, J. Cell Sci. 110(Pt 11):1279-1285, Jun. 1997.
Deb, et al., Embryonic Stem Cells: From Markers to Market 11(1):19-37, Feb. 2008.
Denker, H.W., Human Embryonic Stem Cells: The Real Challenge for Research as Well as for Bioethics is Still Ahead of Us, Cells Tissues Organs 187(4):250-256, 2008.

(56) References Cited

OTHER PUBLICATIONS

Dewitt, et al., Diversomers: An Approach to Nonpeptide, Nonoligomeric Chemical Diversity, Proc. Natl Acad. Sci. USA 90(15):6909-6913, Aug. 1, 1993.
Dimos, et al., Induced Pluripotent Stem Cells Generated From Patients With ALS Can be Differentiated Into Motor Neurons, Science 321(5893):1218-1221, Aug. 29, 2008.
D'Ippolito, et al., Marrow-Isolated Adult Multilineage Inducible (MIAMI) Cells, A Unique Population of Postnatal Young and Old Human Cells With Extensive Expansion and Differentiation Potential, J. Cell Sci. 117(Pt. 14):2971-2981, Jun. 15, 2004.
Do, et al., Nuclei of Embryonic Stem Cells Reprogram Somatic Cells, Stem Cells ' 22:941-949, 2004.
Doetschman, et al., Establishment of Hamster Blastocyst-Derived Embryonic Stem Cells Development 224:127, 1988.
Durcova-Hills, et al., Induced Reprogramming of Human Somatic Cells Into Pluripotency: A New Way How to Generate Pluripotent Stem Cells, Differentiation 76(4):323-325, Apr. 2008.
Ebert, et al., Induced Pluripotent Stem Cells from a Spinal Muscular Atrophy Patient, Nature 457(7227):277-280, Jan. 15, 2009.
Ebert, L., Yamanaka Scooped on iPS (Stem Cell) patent?! TMCNews, Jan. 4, 2009, available at http://ipbiz.blogspot.com/2009/01/yamanaka-scooped-on-ips-stemcell.html, accessed May 19, 2009.
Enrich, et al., Quantitative High-Throughput Analysis of DNA Methylation Patterns by Base-Specific Cleavage and Mass Spectrometry, Proc. Natl. Acad. Sci. USA.102(44):15785-15790, Nov. 1, 2005.
Eisen, et al., Cluster Analysis and Display of Genome-Wide Expression Patterns 95(25):14863-14868, Dec. 8, 1998.
Elefanty, A., Ed., In this Issue . . . , Stem Cell Research. 1:87, 2008.
Essentials of Stem Cell Biology, R. Lanza, et al., eds., Elsevier Academic Press. 2006.
Evans, et al., Establishment in Culture of Pluripotential Cells From Mouse Embryos, Nature 292:154-56, 1981.
Evans, et al., Krüppel-Like Factor 4 is Acetylated by p300 and Regulates Gene Transcription via Modulation of Histone Acetylation, J. Biol. Chem. 282(47):33994-4002, Nov. 23, 2007.
Examination Report dated Apr. 18, 2011, issued in connection with Australian Patent Application No. 2006325975.
Extended European Search Report dated Jun. 10, 2010, issued in connection with European Patent Application No. 10154819.6.
Extended European Search Report dated Jun. 10, 2010, issued in connection with European Patent Application No. EP 10154817.0.
Extended European Search Report dated Jun. 10, 2010, issued in connection with European Patent Application No. EP 10154821.2.
Extended European Search Report dated Mar. 11, 2009, issued in connection with European Patent Application No. EP 06834636.0.
Felgner, et al., Lipofection: A Highly Efficient, Lipid-Mediated DNA-Transfection Procedure. Proc. Natl. Acad. Sci. USA 84(21):7413-7417, Nov. 1987.
Feng, et al., Reprogramming of Fibroblasts Into Induced Pluripotent Stem Cells With Orphan Nuclear Receptor Esrrb, Nature Cell Biology 11:197-203, 2009.
Ferrer-Costa, et al., PMUT: A Web-Based Tool for the Annotation of Pathological Mutations on Proteins, Bioinformatics 21(14):3176-3178, Jul. 15, 2005.
Forsyth, et al., Human Embryonic Stem Cell Telomere Length Impacts Directly on Clonal Progenitor Isolation Frequency, Rejuvenation Research 11(1):5-17, Feb. 2008.
Furler, et al., Recombinant AAV Vectors Containing the Foot and Mouth Disease Virus 2A Sequence Confer Efficient Bicostronic Gene Expression in Cultured Cells and Rat Substantia Nigra Neurons, Gene Therapy 8:864-873, 2001.
Fusaki, N., et al., Efficient Induction of Transgene-Free Human Pluripotent Stem Cells Using a Vector Based on Sendai Virus, An RNA Virus That Does Not Integrate Into the Host Genome, Proc. Jpn. Acad. Ser. B Phys. Biol. Sci. 85:348-362, 2009.

Gallop, et al., Applications of Combinatorial Technologies to Drug Discovery. 1. Background and Peptide Combinatorial Libraries, J. Med. Chem. 37(9):1233-1251, Apr. 29, 1994.
Ghaleb, et al., Krüppel-Like Factors 4 and 5: The Yin and Yang Regulators of Cellular Proliferation, Cell Res. 15(2):92-96, Feb. 2005.
Gonzales, et al., Generation of Mouse Induced Pluripotent Stem Cells by Transient Expression of a Single Nonviral Polycistronic Vector, PNAS 106:8919-8922, 2009.
Goswami, et al., Embryonic Stem Cell Therapy, IDrugs 10(10):713-719, Oct. 2007.
Griffiths-Jones, et al., miRBase: Tools for microRNA Genomics, Nucleic Acids Research 36:D154-D158, published online Nov. 8, 2007.
Gu, et al., Opposite Regulation of Gene Transcription and Cell Proliferation by c-Myc and Max, Proc. Natl Acad. Sci. USA 90(7):2935-2939, Apr. 1, 1993.
Ha, et al., Cryopreservation of Human Embryonic Stem Cells Without the Use of a Programmable Freezer, Hum. Reprod. 20(7):1779-1785, Jul. 2005.
Hakelien, et al., Reprogramming Fibroblasts to Express T-Cell Functions Using Cell Extracts, Nature Biotechnology 20:460-466, May 2002.
Hanna, et al., Direct Reprogramming of Terminally Differentiated Mature B Lymphocytes to Plunpotency, Cell 133:250-264, Apr. 18, 2008; Erratum in Cell. 134(2):365, 2008.
Hanna, et al., Treatment of Sickle Cell Anemia Mouse Model With iPS Cells Generated From Autologous Skin, Science 318(5858):1920-1923, published online Dec. 6, 2007.
Hasegawa, et al., Efficient Multicistronic Expression of a Transgene in Human Embryonic Stem Cells, Stem Cells 25:1707-1712, 2007.
Hatfield, et al., Stem Cell Division is Regulated by the microRNA Pathway, Nature 435(7044):974-978, 2005.
Heng, et al., Incorporating Protein Transduction Domains (PTD) Within Intracellular Proteins Associated With the 'Stemness' Phenotype. Novel Use of Such Recombinant 'Fusion' Proteins to Overcome Current Limitations of Applying Autologous Adult Stem Cells in Regenerative Medicine? Med. Hypotheses 64(5):992-996, 2005.
Hermann, et al., Efficient Generation of Neural Stem Cell-Like Cells From Adult Human Bone Marrow Stromal Cells, J. Cell Sci. 117(Pt. 19):4411-4422, Sep. 1, 2004.
Herold, et al., Negative Regulation of the Mammalian UV Response by Myc Through Association with Miz-1, Mol. Cell 10(3):509-521, 2002.
Highfield, R., Dolly Creator Proflan Wilmut Shuns Cloning, available at http://www.telegraph.co.uk/earth/main.jhtml?xml=/earth/2007/11/16/scidolly116.xml. Accessed Nov. 12, 2008.
Hockemeyer, et al., A Drug-Inducible System for Direct Reprogramming of Human Somatic Cells to Pluripotency, Cell Stem Cell 3(3):346-353, Sep. 11, 2008.
Hoffman, L., and M. Carpenter, Characterization and Culture of Human Embryonic Stem Cells, Nature Biotechnology 23:699, 2005.
Holt, et al., Regulation of Telomerase Activity in Immortal Cell Lines, Molecular and Cellular Biology, Jun. 1996, pp. 2932-2939.
Hong, et al., Suppression of Induced Pluripotent Stem Cell Generation by the p53-p21 Pathway, Nature 460(7259):1132-1135, Aug. 27, 2009; epub Aug. 9, 2009.
Horikawa, et al., Differential Cis-Regulation of Human Versus Mouse TERT Gene Expression In Vivo: Identification of a Human-Specific Repressive Element, Proc. Natl. Acad. Sci. U.S.A. 102(51):18437-18442, 2005.
Houbaviy, et al., Embryonic Stem Cell-Specific MicroRNAs, Developmental Cell 5(2):351-58, 2003.
Hsiao, et al., Marking Embryonic Stem Cells With a 2A Self-Cleaving Peptide: A NKX2-5 Emerald GFP BAC Reporter, PLoS ONE 3(7):e2532, 2008.
Huangfu, et al., Efficient Induction of Pluripotent Stem Cells Using Small Molecule Compounds, companion manuscript to U.S. Appl. No. 61/029,287.

(56) References Cited

OTHER PUBLICATIONS

Huangfu, et al., Induction of Pluripotent Stem Cells by Defined Factors is Greatly Improved by Small-Molecule Compounds, Nature Biotechnology 26(7):795-797, 2008.

Huangfu, et al., Induction of Pluripotent Stem Cells From Primary Human Fibroblasts With Only Oct4 and Sox 2, Nature Biotechnology 26:1269-1275, 2008.

Humphries, C., Reprogrammed Stem Cells Work on Parkinson's: A Study in Rodents Suggests that Skin Cells Can Be Transformed into Neurons to Treat Neurodegeneration, Technology Review, Massachusetts Institute of Technology, Apr. 8, 2008, available at http://www.technologyreview.com/printer_friendly_article.aspx?id=20530.

Hwang, et al., Evidence of Pluripotent Human Embryonic Stem Cell Line Derived From a Cloned Blastocyst, Science 303:1669-1674, 2004.

Hwang, et al., Patient-Specific Embryonic Stem Cells Derived From Human SCNT Blastocysts, Science 308:1777-1783, 2005.

Hyun, et al., New Advances in iPS Cell Research Do Not Obviate the Need for Human Embryonic Stem Cells, Cell Stem Cell 1(4):367-368, Oct. 11, 2007.

Iannaccone, et al., Pluripotent Embryonic Stem Cells From the Rat Are Capable of Producing Chimeras, Developmental Biology 163(288), 1994.

Ingvarsson, et al., Structure and Expression of B-myc, A New Member of the myc Gene Family, Mol. Cell. Biol. 8(8):3168-3174, Aug. 1988.

Ingvarsson, The myc Gene Family Proteins and Their Role in Transformation and Differentiation, Seminars in Cancer Biology vol. 1:359-369, 1990.

International Search Report and Written Opinion dated Jul. 28, 2011, issued in connection with International Patent Application No. PCT/JP2011/051685.

International Search Report dated Dec. 15, 2008, issued in connection with International Patent Application No. PCT/EP2008/005047.

International Search Report dated Jan. 20, 2010, issued in connection with International Patent Application No. PCT/US2009/047291.

International Search Report dated Jul. 10, 2009, issued in connection with International Patent Application No. PCT/IB2008/002540.

International Search Report dated Jul. 7, 2009, issued in connection with International Patent Application No. PCT/JP2009/058873.

International Search Report dated May 20, 2008, issued in connection with International Patent Application No. PCT/EP2007/010019.

Itskovitz-Eldor, et al., Differentiation of Human Embryonic Stem Cells Into Embryoid Bodies Comprising the Three Embryonic Germ Layers, Mol. Med. 6(2):88-95, 2000.

Itsykson, et al., Derivation of Neural Precursors From Human Embryonic Stem Cells in the Presence of Noggin, Mol. Cell Neurosci. 30(1):24-36, Sep. 2005.

Jaenisch, et al., Stem Cells, The Molecular Circuitry of Pluripotency and Nuclear Reprogramming, Cell 132(4):567-582, Feb. 22, 2008.

Jahagirdar, et al., Multipotent Adult Progenitor Cell and Stem Cell Plasticity, Stem Cell Rev. 1(1):53-59, 2005.

Janssens, et al., Autologous Bone Marrow-Derived Stem-Cell Transfer in Patients With ST-Segment Elevation Myocardial Infarction: Double-Blind, Randomised Controlled Trial, Lancet, 367(9505):113-121, Jan. 14, 2006.

Jiang, et al., A Core Klf Circuitry Regulates Self-Renewal of Embryonic Stem Cells, Nat. Cell Biol. 10(3):353-360, Mar. 2008.

Jiang, et al., Pluripotency of Mesenchymal Stem Cells Derived From Adult Marrow, Nature 418(6893):41-49, Jul. 4, 2002.

Jikken Igaku (Experimental Medicine) 24:814-819, 2006, along with an English language translation thereof.

Johnston, et al., Minimum Requirements for Efficient Transduction of Dividing and Nondividing Cells by Feline Immunodeficiency Virus Vectors, J. Virol. 73(6):4991-5000, Jun. 1999.

Kaji, et al., Virus-Free Induction of Pluripotency and Subsequent Excision of Reprogramming Factors, Nature 458(7239):771-775, Mar. 1, 2009.

Kamachi, et al., Mechanism of Regulatory Target Selection by the SOX High-Mobility-Group Domain Proteins as Revealed by Comparison of SOX1/2/3 and SOX9, Mol. Cell Biol. 19(1):107-120, Jan. 1999.

Kanegae, et al., Efficient Gene Activation in Mammalian Cells by Using Recombinant Adenovirus Expressing Site-Specific Cre Recombinase, Nucleic Acids Res. 23(19):3816-3821, Oct. 11, 1995.

Kanellopoulou, et al., Dicer-Deficient Mouse Embryonic Stem Cells Are Defective in Differentiation and Centromeric Silencing, Genes & Development 19:489-501, 2005.

Kawasaki, et al., Induction of Midbrain Dopaminergic Neurons From ES cells by Stromal Cell-Derived Inducing Activity, Neuron. 28(1):31-40, Oct. 2000.

Kim et al., Pluripotent Stem Cells Induced From Adult Neural Stem Cells by Reprogramming with Two Factors, Nature 454:646-650, 2008.

Kim, et al., Ex Vivo Characteristics of Human Amniotic Membrane-Derived Stem Cells, Cloning Stem Cells 9(4):581-594, Winter 2007.

Kim, et al., Generation of Human Induced Pluripotent Stem Cells by Direct Delivery of eprogramming Proteins, Cell Stem Cell 4:472-476, 2009.

Kim, et al., Oct4-Induced Pluripotency in Adult Neural Stem Cells, Cell 136:411-419, 2009.

Kishi et al., Requirement of Sox2-Mediated Signaling for Differentiation of Early Xenopus Neuroectoderm, Development 127:791-800, 2000.

Kitamura, et al., Retrovirus-Mediated Gene Transfer and Expression Cloning: Powerful Tools in Functional Genomics, Exp. Hematol. 31(11):1007-1014, Nov. 2003.

Kitamura, T., New Experimental Approaches in Retrovirus-Mediated Expression Screening. Int. J. Hematol. 67(4):351-359, Jun. 1998.

Klingemann, H., Discarded Stem Cells With a Future? Expert Opin. Biol. Ther. 6(12):1251-1254, Dec. 2006.

Knoblich, J.A., Mechanisms of Asymmetric Stem Cell Division, Cell 132(4):583-597, Feb. 22, 2008.

Koch, et al., Transduction of Human Embryonic Stem Cells by Ecotropic Retroviral Vectors. Nucl. Acids Res. 34:e120, 2006.

Kohge, et al., Promotion of Antigen-Specific Antibody Production in Murine B Cells by a Moderate Increase in Histone Acetylation, Biochem. Pharmacol. 56(10):1359-1364, Nov. 15, 1998.

Kohlhase, et al., Cloning and Expression Analysis of Sall4, The Murine Homologue of the Gene Mutated in Okihiro Syndrome, Cytogenet. Genome Res. 98:274-277, 2002.

Kopsidas, et al., RNA Mutagenesis Yields Highly Diverse mRNA Libraries for In Vitro Protein Evolution, BMC Biotechnol. 7:18, Apr. 11, 2007.

Koyanagi, et al., Screening and Functional Analysis of microRNAs Which Involve in Reprogramming, of Murine Somatic Cells, The Journal of Biochemistry 79(11), Abstract, 1T-7-7 From the 80th Annual Meeting of the Japanese Biochemical Society, Nov. 25, 2007, along with an English language translation thereof.

Kozarsky, et al., A denovirus-Mediated Correction of the Genetic Defect in Hepatocytes from Patients with Familial Hypercholesterolemia Somatic Cell Molecular Genetics 19:449-458, 1993.

Kramer, et al., Embryonic Stem Cell-Derived Chondrogenic Differentiation In Vitro: Activation by BMP-2 and BMP-4, Mech. Dev. 92(2):193-205, Apr. 2000.

Krausz, E., High-Content siRNA Screening, Mol. Biosyst. 3(4):232-240, Apr. 2007.

Krosl, et al., In vitro Expansion of Hematopoietic Stem Cells by Recombinant TAT-HOXB4 Protein, Nat. Med 9(11):1428-32, 2003.

Kubicek, et al., Reversal of H3K9me2 by a Small-Molecule Inhibitor for the G9a Histone Methyltransferase, Molecular Cell 25:473-481, 2007.

(56) References Cited

OTHER PUBLICATIONS

Kunath, et al., FGF Stimulation of the Erk1/2 Signalling Cascade Triggers Transition of Pluripotent Embryonic Stem Cells From Self-Renewal to Lineage Commitment, Development. 134(16):2895-2902, Aug. 2007.
Kuroda, et al., Octamer and Sox Elements Are Required for Transcriptional cis Regulation of Nanog Gene Expression, Mol. Cell. Biol. 25(6):2475-2485, Mar. 2005.
Kyoto Shimbun, Col. 1-3, Apr. 16, 2008, along with a partial English language translation thereof.
LaFlamme, et al., Cardiomyocytes Derived From Human Embryonic Stem Cells in Pro-Survival Factors Enhance Function of Infarcted Rat Hearts, Nat. Biotechnol. 25(9):1015-1024, 2007.
Laird, et al., Stem Cell Trafficking in Tissue Development, Growth, and Disease, Cell 132(4):612-630, Feb. 22, 2008.
Lebkowski, et al., Human Embryonic Stem Cells: Culture, Differentiation, and Genetic Modification for Regenerative Medicine Applications, The Cancer Journal 7(S.2):S83-S94, 2001.
Lee, et al., Efficient Generation of Midbrain and Hindbrain Neurons From Mouse Embryonic Stem Cells, Nat. Biotechnol. 18(6):675-679, Jun. 2000.
Lemken, et al., Evidence for Intercellular Trafficking of VP22 in Living cells, Mol. Ther. 15(2):310-319, Feb. 2007.
Lengner, et al., The Pluripotency Regulator Oct4: A Role in Somatic Stem Cells? Cell Cycle 7(6):725-728, Mar. 2008.
Lewitzky, et al., Reprogramming Somatic Cells Towards Pluripotency by Defined Factors, Curr. Opin. Biotechnol. 18(5):467-473, Oct. 2007.
Li, et al., Leukaemia Disease Genes: Large-Scale Cloning and Pathway Predictions, Nat. Genet. 23(3):348-353, 1999.
Li, et al., Murine Embryonic Stem Cell Differentiation is Promoted by SOCS-3 and Inhibited by the Zinc Finger Transcription Factor Klf4, Blood 105(2):635-637, Jan. 15, 2005.
Li, H., et al., Pluripotent Stem Cells From the Adult Mouse Inner Ear, Nature Medicine 9(10):1293-1299, Oct. 2003.
Li, et al., Small dsRNAs Induce Transcriptional Activation in Human Cells, Proc. Natl. Acad. Sci. 2006; 103, 17337-17342.
Li, Y., et al., Transduction of Passaged Human Articular Chondrocytes with Adenoviral, Retroviral, and Lentiviral Vectors and the Effects of Enhanced Expression of Sox9, Tissue Eng. 10:575-584, 2004.
Li, Y., Expansion of Human Embryonic Stem Cells in Defined Serum-Free Medium Devoid of Animal-Derived Products, published online Jun. 21, 2005, in Wiley InterScience, www.interscience.wiley.com.
Liao, et al., Enhanced Efficiency of Generating Induced Pluripotent Stem (iPS) Cells From Human Somatic Cells by a Combination of Six Transcription Factors, Cell Research 18:600-603, published online Apr. 15, 2008.
Lieschke, et al., Development of Functional Macrophages From Embryonal Stem Cells In Vitro, Exp. Hematol. 23(4):328-334, Apr. 1995.
Lin, et al., Mir-302 Reprograms Human Skin Cancer Cells Into a Pluripotent ES-Cell-Like State, RNA 14:1-10, 2008.
Lin-Goerke, et al., PCR-Based Random Mutagenesis Using Manganese and Reduced dNTP Concentration, Biotechniques 23(3):409-412, Sep. 1997.
Link et al- Therapeutic Protein Transduction of Mammalian Cells and Mice by Nucleic ' Acid-Free Lentiviral Nanoparticles, Nucleic Acids Res. 34(2):e16, Jan. 2006.
Littlewood, et al., A Modified Oestrogen Receptor Ligand-Binding Domain as an Improved Switch for the Regulation of Heterologous Proteins, Nucleic Acids Res. 23(10):1686-1690, May 25, 1995.
Liu, S., iPS Cells: A More Critical Review, Stem Cells and Development 17(3):391-397, Jun. 2008.
Loh, et al., The Oct4 and Nanog Transcription Network Regulates Pluripotency in Mouse Embryonic Stem Cells, Nat. Genet. 38(4):431-440, Apr. 2006.

Loriot, et al., Five New Human Cancer-Germline Genes Identified Among 12 Genes Expressed in Spermatogonia, Int. J. Cancer 105:371-76, 2003.
Loudig, et al., Transcriptional Co-Operativity Between Distant Retinoic Acid Response Elements in Regulation of Cyp26A1 Inducibility, Biochem. J. 392(Pt. 1):241-248, Nov. 15, 2005.
Lowry, et al., Generation of Human Induced Pluripotent Stem Cells From Dermal Fibroblasts, Proc. Natl. Acad. Sci. USA 105(8):2883-2888, Feb. 26, 2008.
Ludwig, et al., Derivation of Human Embryonic Stem Cells in Defined Conditions, Nat. Biotechnol. 24(2):185-187, Feb. 2006.
Luke, G.A., 2012, Translating 2A Research into Practice, Innovations in Biotechnology, Agbo, E.C. (Ed.), InTech, available from: http://www.intechopen.com/booksinnovations-in-biotechnology/translating/translating-2a-research, 2012.
Lumelsky, et al., Differentiation of Embryonic Stem Cells to Insulin-Secreting Structures Similar to Pancreatic Islets, Science 292(5520):1389-1394, May 18, 2001.
Lunde, et al., Zebrafish pou5fl/pou2, Homolog of Mammalian Oct4, Functions in the Endoderm Specification Cascade, Curr. Biol. 14(1):48-55, Jan. 6, 2004.
Summaries of Review for Applications to RFA 07-05, California Institute for Regenerative Medicine Web site, 2007, available at: http://www.cirm.ca.gov/RFAlrfa_07-05/, accessed Jul. 1, 2008.
The Novel Pluripotent Cells Established by Professor Yamanaka of Kyoto University May Change Medical Care, Asahi Shimbun Weekly AERA, Dec. 24, 2007, pp. 72-73, along with a partial English language translation thereof.
Lungwitz, et al., Polyethylenimine-Based Non-Viral Gene Delivery Systems, Eur. J. Pharm. Biopharm. 60(2):247-266, Jul. 2005.
Maherali, et al., A high-Efficiency System for the Generation and Study of Human Induced Pluripotent Stem Cells, Cell Stem Cell 3(3):340-345, Sep. 11, 2008.
Maherali, et al., Directly Reprogrammed Fibroblasts Show Global Epigenetic Remodeling and Widespread Tissue Contribution, Cell Stem Cell 1(1):55-70, Jun. 7, 2007.
Mali, et al., Improved Efficiency and Pace of Generating Induced Pluripotent Stem Cells From Human Adult and Fetal Fibroblasts, Stem Cells 26(8):1998-2005, 2008.
Marchetto, et al., Transcriptional Signature and Memory Retention of Human-Induced Pluripotent Stem Cells, PLoS One 4(9):e7076, Sep. 18, 2009.
Marson, et al., Wnt Signaling Promotes Reprogramming of Somatic Cells to Pluripotency, Cell Stem Cell 3:132-35, 2008.
Martin, Isolation of a Pluripotent Cell Line From Early Mouse Embryos Cultured in Medium Conditioned by Teratocarcinoma Stem Cells, Proc. Natl. Acad. Sci. U.S.A. 78(12):7634-38, 1981.
Maruyama et al., Differential Roles for Sox15 and Sox2 in Transcriptional Control in Mouse Embryonic Stem Cells, J. Biol., Chem. 280(26):24371-79, 2005.
Maruyama, Functional Analysis of Sox15 and Sox2, Ph.D. Thesis, Nara Institute of Science and Technology, Jan. 31, 2005, 121 pages.
Masaki, et al., Heterogeneity of Pluripotent Marker Gene Expression in Colonies Generated in Human iPS Cell Induction Culture, Stem Cell Research 1:105-115, 2008.
Masaki, et al., Tendency of Pluripotential Marker Gene Expression in Colonies Derived From Human Neonatal Fibroblasts Induced by the Human iPS Cell Method, Stem Cell Research, 2008 (accepted manuscript).
Mathe, et al., Computational Approaches for Predicting the Biological Effect of p53 Missense Mutations: A Comparison of Three Sequence Analysis Based Methods, Nucleic Acids Res. 34(5):1317-1325, Mar. 6, 2006.
Matsuda, et al., STAT3 Activation is Sufficient to Maintain an Undifferentiated State of Mouse Embryonic Stem Cells, EMBO J.18(15):4261-4269, Aug. 2, 1999.
McMahon, et al., The Wnt-1 (int-1) Proto-Oncogene Is Required for Development of a Large Region of the Mouse Brain, Cell 62:1073-1085, 1990.
Meiner, et al., Disruption of the Acyl-CoA: Cholesterol Acyltransferase Gene in Mice: Evidence Suggesting Multiple Cholesterol Esterification Enzymes in Mammals, Proc. Natl. Acad. Sci. U.S.A. 93:14041-14046, 1996.

(56) References Cited

OTHER PUBLICATIONS

Meissner, et al., Direct Reprogramming of Genetically Unmodified Fibroblasts Into Pluripotent Stem Cells, Nat. Biotechnol. 25(10):1177-1181, published online Aug. 27, 2007.
microRNA Jikken Purotokoru (microRNA Experimental Protocol), Yodosha Co., Ltd., pp. 20-35.
Mikkelsen, et al., Dissecting Direct Reprogramming Through Integrative Genomic Analysis, Nature 454(7200):49-55, Jul. 3, 2008; Erratum in Nature 454(7205):794, 2008.
Mitsui, et al., The Homeoprotein Nanog Is Required for Maintenance of Pluripotency in Mouse Epiblast and ES Cells, Cell 113:631-42, 2003.
Miura, et al., Variation in the Safety of Induced Pluripotent Stem Cell Lines, Nat. Biotechnol. 27(8):743-745, Aug. 2009, Epub Jul. 9, 2009.
Miyagishi, et al., Strategies for Generation of an siRNA Expression Library Directed Against the Human Genome, Oligonucleotides 13(5):325-333, 2003.
Miyamoto, et al., Reprogramming Events of Mammalian Somatic Cells Induced by Xenopus Laevis Egg Extracts Molecular Reproduction and Development 74:1268-1277, 2007.
Miyoshi, et al., Development of a Self-Inactivation Lentivirus Vector, J. Virol. 72(10):8150-8157, Oct. 1998.
More California Dough—$23 Million—Rolls Out the Door for Stem Cell Research, California Stem Cell Report Web Site, 2005; available at http://californiastemcellreport.blogspot.com/2008/06/more-dough-25-million-rolls-out-door-in.html; accessed Jul. 1, 2008.
Morgenstern, et al., Advanced Mammalian Gene Transfer: High Titre Retroviral Vectors With Multiple Drug Selection Markers and a Complementary Helper-Free Packaging Cell Line, Nucleic Acids Res. 18(12):3587-3596, Jun. 25, 1990.
Morita, et al., Plat-E: An Efficient and Stable System for Transient Packaging of Retroviruses, Gene Ther. 7:1063-1066, 2000.
Morizane, et al., From Bench to Bed: The Potential of Stem Cells for the Treatment of Parkinson's Disease, Cell Tissue Res. 331(1):323-336, Jan. 2008.
Morling, et al., Enhanced Transduction Efficiency of Retroviral Vectors Coprecipitated With Calcium Phosphate, Gene Ther. 2(7):504-548, Sep. 1995.
Morrison, S.J., Stem Cells and Niches: Mechanisms That Promote Stem Cell Maintenance Throughout Life, Cell. 132(4):598-611, Feb. 22, 2008.
Mummery, et al., Differentiation of Human Embryonic Stem Cells to Cardiomyocytes: Role of Coculture With Visceral Endoderm-Like Cells, Circulation 107(21):2733-2740, Jun. 3, 2003.
Murry, et al., Differentiation of Embryonic Stem Cells to Clinically Relevant Populations: Lessons From Embryonic Development, Cell 132(4):661-680, Feb. 22, 2008.
Nagano, et al., Large-Scale Identification of Proteins Expressed in Mouse Embryonic Stem Cells, Proteomics 5:1346-1361, 2005.
Nagy, et al., Embryonic Stem Cells Alone Are Able to Support Fetal Development in the Mouse, Development 110(3):815-821, Nov. 1990.
Nakagawa et al., Promotion of Direct Reprogramming by Transformation-Deficient Myc. Proc. Natl. Acad. Sci. USA. 107(32):14152-14157, Aug. 10, 2010; Epub Jul. 26, 2010.
Nakagawa, et al., Generation of Induced Pluripotent Stem Cells Without Myc From Mouse and Human Fibroblasts, Nat. Biotechnol. 26(1):101-06, published online Nov. 30, 2007.
Nakatake, et al., Klf4 Cooperates With Oct3/4 and Sox2 to Activate the Lefty1 Core Promoter in Embryonic Stem Cells, Mol. Cell Biol. 26(20):7772-7782, Oct. 2006.
Naldini, et al., In Vivo Gene Delivery and Stable Transduction of Nondividing Cells by a Lentiviral Vector, Science 272(5259):263-267, Apr. 12, 1996.
Needleman, et al., A General Method Applicable to the Search for Similarities in the Amino Acid Sequence of Two Proteins, J. Mol. Biol. 48(3):443-453, Mar. 1970.
Nègre, et al., Lentiviral Vectors Derived From Simian Immunodeficiency Virus, Curr. Top Microbiol. Immunol. 261:53-74, 2002.
Newton, Attracting World's Attention. Pluripotent Cells Are Generated From Human Skin. What is the 'iPS Cell' That Can Be Used Not Only in the Regeneration Therapy but Also in the Tailor-Made Therapy, pp. 70-75, Feb. 2008, along with a partial English translation thereof.
Ng, et al., Predicting the Effects of Amino Acid Substitutions on Protein Function, Annu. Rev. Genomics, Hum. Genet. 7:61-80, 2006.
Nichols, et al., Formation of Pluripotent Stem Cells in the Mammalian Embryo Depends on the POU Transcription Factor Oct4, Cell 95:379-391, 1998.
Nienhuis, et al., Genotoxicity of Retroviral Integration in Hematopoietic Cells, Mol. Ther. 13(6):1031-1049, 2006.
Niwa, et al., Self-Renewal of Pluripotent Embryonic Stem Cells is Mediated Via Activation of STAT3, Genes Dev. 12(13):2048-2060, Jul. 1, 1998.
Niwa, et al., Phenotypic Complementation Establishes Requirements for Specific POU Domain and Generic Transactivation Function of Oct-3/4 in Embryonic Stem Cells, Molecular and Cellular Biology, 22:1526-1536, 2002.
Niwa, et al., Efficient Selection for High-Expression Transfectants With a Novel Eukaryotic Vector, Gene 108(2):193-199,1991.
Nolta, et al., Transduction of Pluripotent Human Hematopoietic Stem Cells Demonstrated by Clonal Analysis After Engraftment in Immune-Deficient Mice, Proc. Natl. Acad. Sci. USA 93(6):2414-2419, 1996.
Obinata, Conditionally Immortalized Cell Lines With Differentiated Functions Established From Temperature-Sensitive T-Antigen Transgenic Mice, Genes to Cells 2:235-244, 1997.
Office Action dated Oct. 4, 2010, issued in connection with U.S. Appl. No. 12/157,967.
Office Action dated Jun. 20, 2007, issued in connection with U.S. Appl. No. 10/861,040.
Office Action dated Feb. 10, 2012, issued in connection with Canadian Patent Application No. 2,632,142.
Office Action dated Sep. 9, 2010, issued in connection with Chinese Patent Application No. 200680048227.7.
Office Action dated Apr. 30, 2010, issued in connection with European Patent Application No. EP 06834636.0.
Office Action dated Oct. 25, 2010, issued in connection with European Patent Application No. EP 06834636.0.
Office Action dated Aug. 19, 2010, issued in connection with Israeli Patent Application No. 191903.
Office Action dated Jun. 2, 2009, issued in connection with Japanese Patent Application No. JP 2009-056747.
Office Action dated Jun. 2, 2009, issued in connection with Japanese Patent Application No. JP 2009-056748.
Office Action dated Jun. 4, 2009, issued in connection with Japanese Patent Application No. JP 2009-056749.
Office Action dated Jun. 2, 2009, issued in connection with Japanese Patent Application No. JP 2009-056750.
Office Action dated Apr. 20, 2010, issued in connection with New Zealand Patent Application No. 569530.
Office Action dated Apr. 13, 2010, issued in connection with Singapore Patent Application No. 200804231-9.
Office Action dated Jan. 22, 2010, issued in connection with Singapore Patent Application No. 200901803-7.
Official Action dated Nov. 9, 2009, issued in connection with Eurasian Patent Application No. 200870046.
Official Action dated Jul. 14, 2010, issued in connection with Eurasian Patent Application No. 201000858.
Official Action dated Nov. 4, 2009, issued in connection with Japanese Patent Application No. JP 2009-056748.
Official Rejection dated Feb. 23, 2010, issued in connection with Japanese Patent Application No. JP 2009-056748.
Official Rejection dated Nov. 4, 2009, issued in connection with Japanese Patent Application No. JP 2009-056749.
Ohnuki, et al., Generation and Characterization of Human Induced Pluripotent Stem Cells, Curr. Protoc Stem Cell Biol., Chapter 4:Unit 4A.2, Jun. 2009.

(56) References Cited

OTHER PUBLICATIONS

Okabe, et al., 'Green Mice' as a Source of Ubiquitous Green Cells, FEBS Letters 407:313-319, 1997.
Okamoto, et al., A Novel Octamer Binding Transportation Factor is Differentially Expressed in Mouse Embryonic Cells, Cell 60:461-72, 1990.
Okita, et al., Generation of Germline-Competent Induced Pluripotent Stem Cells, Nature 448(7151)313-317, Jul. 19, 2007.
Okita, et al., Intracellular Signaling Pathways Regulating Pluripotency of Embryonic Stem Cells, Current Stem Cell Research & Therapy 1:103-111, 2006.
Okita et al., Generation of Mouse-Induced Pluripotent Stem Cells With Plasmid Vectors, Nat. Protoc. 5(3):418-428, 2010; Epub Feb. 11, 2010.
Okita et al., Induction of Pluripotency by Defined Factors, Exp. Cell Res. 316(16):2565-2570, Oct. 1, 2010; Epub Apr. 24, 2010.
Okita, et al., Generation of Mouse Induced Pluripotent Stem Cells Without Viral Vectors, Science 322(5903):949-953, published online Oct. 9, 2008.
Okuda, et al., UTF1, A Novel Transcriptional Coactivator Expressed in Pluripotent Embryonic Stem Cells and Extra-Embryonic Cells, EMBO J. 17(7):2019-2032, 1998.
Okumura-Nakanishi, et al., Oct-3/4 and Sox2 Regulate Oct-3/4 Gene in Embryonic Stem Cells, The Journal of Biological Chemistry 280(7):5307-5317, Feb. 18, 2006.
Onishi, et al., Applications of Retrovirus-Mediated Expression Cloning, Exp. Hematol. 24(2):324-329, Feb. 1996.
Orkin, et al., Hematopoiesis: An Evolving Paradigm for Stem Cell Biology, Cell 32(4):631-644, Feb. 22, 2008.
Osuna, et al., Protein Evolution by Codon-Based Random Deletions, Nucleic Acids Res. 32(17):e136, Sep. 30, 2004.
Padmanabhan, et al., Visualization of Telomerase Reverse Transcriptase (hTERT) Promoter Activity Using a Trimodality Fusion Reporter Construct, J. Nucl. Med. 47(2):270-277, Feb. 2006.
Park, et al., Disease-Specific Induced Pluripotent Stem Cells, Cell 134(5):877-886, Sep. 5, 2008.
Park, et al., Reprogramming of Human Somatic Cells to Pluripotency With Defined Factors, Nature 451:141-146, published online Dec. 23, 2007.
Park, A., Stem-cell Research: The Quest Resumes, Time Magazine, Feb. 9, 2009; available at http://www.time.com/time/health/article/0,8599,1874717,00.html; accessed Jun. 3, 2009.
Parson, A.B., Stem Cell Biotech: Seeking a Piece of the Action, Cell 132(4):511-513, Feb. 22, 2008.
Pear, et al., Production of High-Titer Helper-Free Retroviruses by Transient Transfection, Proc. Natl. Acad. Sci. USA 90:8392-8396, 1993.
Pearson, et al., Improved Tools for Biological Sequence Comparison, Proc. Natl. Acad. Sci. USA 85(8):2444-2448, Apr. 1988.
Pearson, W.R., Rapid and Sensitive Sequence Comparison With FASTP and FASTA Methods Enzymol. 183:63-98, 1990.
Peister, et al., Stable Transfection of MSCs by Electroporation, Gene Ther. 11(2):224-228, Jan. 2004.
Pera, M.F., On the Road to Reprogramming, Stem Cell Research 1:103-104, 2008.
Pomp, et al., Generation of Peripheral Sensory and Sympathetic Neurons and Neural Crest Cells From Human Embryonic Stem Cells, Stem Cells 23(7):923-930, Aug. 2005.
Postic, et al., Dual Roles for Glucokinase in Glucose Homeostasis as Determined by Liver and Pancreatic β Cell-Specific Gene Knock-Outs Using Cre Recombinase, J. Biol. Chem. 274(1):305-315, 1999.
Pralong, et al., Cell Fusion for Reprogramming Pluripotency: Toward Elimination of the Pluripotent Genome, Stem Cell Rev. 2(4):331-340, 2006.
Prelle, et al., Overexpression of Insulin-Like Growth Factor-II in Mouse Embryonic Stem Cells Promotes Myogenic Differentiation, Biochem. Biophys. Res. Commun. 277(3):631-638, Nov. 2, 2000.
Qin, et al., Direct Generation of ES-Like Cells From Unmodified Mouse Embryonic Fibroblasts by Oct4/Sox2/Myc/Klf4, Cell Res. 17(11):959-962, 2007.
Quenneville, et al., Nucleofection of Muscle-Derived Stem Cells and Myoblasts with phiC31 Integrase: Stable Expression of a Full-Length-Dystrophin Fusion Gene by Human Myoblasts, Mol. Ther. 10(4):679-687, Oct. 2004.
Rambhatla, et al., Generation of Hepatocyte-Like Cells From Human Embryonic Stem Cells, Cell Transplant. 12(1):1-11, 2003.
Rao, M., Conserved and Divergent Paths That Regulate Self-Renewal in Mouse and Human Embryonic Stem Cells, Dev. Biol. 275(2):269-286, Nov. 15, 2004.
Ratajczak, et al., Bone-Marrow-Derived Stem Cells—Our Key to Longevity? J. Appl. Genet. 48(4):307-319, 2007.
Reubinoff, et al., Neural Progenitors from Human Embryonic Stem Cells, Nat. Biotechnol. 19(12):1134-1140, Dec. 2001.
Riviére, et al., Effects of Retroviral Vector Design on Expression of Human Adenosine Deaminase in Murine Bone Marrow Transplant Recipients Engrafted With Genetically Modified Cells, Proc. Natl. Acad. Sci. USA. 92(15):6733-6737, Jul. 18, 1995.
Rodda, et al., Transcriptional Regulation of Nanog by OCT4 and SOX2, J. Biol. Chem. 280(26):24731-24737, Jul. 1, 2005.
Rodriguez, et al., Manipulation of OCT4 Levels in Human Embryonic Stem Cells Results in Induction of Differential Cell Types, Exp. Biol. Med (Maywood) 232(10):1368-1380, Nov. 2007.
Root, et al., Genome-Scale Loss-of-Function Screening with a Lentiviral RNAi Library, Nat. Methods 3(9):715-719, Sep. 2006.
Rosenfeld, et al., Adenovirus-Mediated Transfer of a Recombinant Alpha 1-Antitrypsin Gene to the Lung Epithelium In Vivo, Science 252(5004):431-434, Apr. 19, 1991.
Rossant, J., Stem Cell and Early Lineage Development, Cell 132(4):527-531, Feb. 22, 2008.
Rossant, J., Stem Cells: The Magic Brew, Nature 448:260-262, Jul. 19, 2007.
Rossi, et al., Stem Cells and the Pathways to Aging and Cancer, Cell 132(4):681-696, Feb. 22, 2008.
Rubin, L., Stem Cell and Drug Discovery: The Beginning of a New Era? Cell 132(4):549-552, Feb. 22, 2008.
Ryan, et al., POU Domain Family Values: Flexibility, Partnerships, and Developmental Codes, Genes Dev. 11:1207-25, 1997.
Rybkin, et al., Journal of Biological Chemistry 278:15927-15934, 2003.
Rybouchkin, A., et al., Role of Histone Acetylation in Reprogramming of Somatic Nuclei Following Nuclear Transfer, Biology of Reproduction 74:1083-1089, 2006.
Sadowski, et al., GAL4-VP16 is an Unusually Potent Transcriptional Activator, Nature 335(6190):563-564, Oct. 6, 1998.
Sakai, et al., A Transgenic Mouse Line That Retains Cre Recombinase Activity in Mature Oocytes Irrespective of the cre Transgene Transmission, Biochem. Biophys. Res. Commun. 237(2):318-324, 1997.
Saldanha, et al., Assessment of Telomere Length and Factors That Contribute to its Stability, Eur. J. Biochem. 270(3):389-403, Feb. 2003.
Salmon, et al., Reversible Immortalization of Human Primary Cells by Lentivector-Mediated Transfer of Specific Genes, Mol. Ther. 2(4):404-414, 2000.
Sarid, J., et al., Evolutionary Conserved Regions of the Human c-Myc Protein Can Be Uncoupled From Transforming Activity, Proc. Natl. Acad. Sci. USA 84(1):170-173, 1987.
Sato, et al., Maintenance of Pluripotency in Human and Mouse Embryonic Stem Cells Through Activation of Wnt Signaling by a Pharmacological GSK-3-Specific Inhibitor, Nat. Med. 10(1):55-63, 2004.
Schepers, et al., Twenty Pairs of Sox: Extent, Homology, and Nomenclature of the Mouse and Human Sox Transcription Factor Gene Families, Dev. Cell 3:167-170, 2002.
Scherr, et al., Gene Silencing by Small Regulatory RNAs in Mammalian Cells, Cell Cycle 6(4):444-449, Feb. 1, 2007.
Schöler, et al., A Family of Octamer-Specific Proteins Present During Mouse Embryogenesis: Evidence for Germline-Specific Expression of an Oct Factor, EMBO J. 8(9):2543-2550, Sep. 1989.
Schuldiner, et al., Induced Neuronal Differentiation of Human Embryonic Stem Cells, Brain Res. 913(2):201-205, Sep. 21, 2001.

(56) References Cited

OTHER PUBLICATIONS

Schwenk, et al., Hybrid Embryonic Stem Cell-Derived Tetraploid Mice Show Apparently Normal Morphological, Physiological, and Neurological Characteristics, Mol Cell Biol. 23(11):3982-3989, Jun. 2003.

Science Magazine Names Top 10 Breakthroughs of 2008; available at http://arstechnica.com/old/content/2008/12/isciencei-names-top-10-scientific-breakthroughs-of-2008.ars; accessed May 19, 2009.

Shah, R., Pharmacogenetics in Drug Regulation: Promise, Potential and Pitfalls, Philos. Trans. R. Soc. Lond. B. Biol. Sci. 360(1460):1617-1638, Aug. 29, 2005.

Shao, et al., Generation of iPS Cells Using Defined Factors Linked Via the Self-Cleaving 2A Sequences in a Single Open Reading Frame, Cell Res. 19(3):296-312, Mar. 2009.

Shi, et al., A Combined Chemical and Genetic Approach for the Generation of Induced Pluripotent Stem Cells, Cell Stem Cell 2:525-528, 2008.

Shi, et al., Induction of Pluripotent Stem Cells From Mouse Embryonic Fibroblasts by Oct4 and Klf4 With Small-Molecule Compounds, Cell Stem Cell 3:568-574, 2008.

Silva, et al., Capturing Pluripotericy, Cell. 132(4):532-536, Feb. 22, 2008.

Silva, et al., Profiling Essential Genes in Human Mammary Cells by Multiplex RNAi Screening, Science 319(5863):617-620, Feb. 1, 2008.

Silva, et al., Promotion of Reprogramming to Ground State Pluripotency by Signal Inhibition, PLoS Biology 6(10):2237-2247, 2008.

Sinkkonen, et al., MicroRNAs Control de novo DNA Methylation Through Regulation of Transcriptional Repressors in Mouse Embryonic Stem Cells, Nat. Struct. Mol. Biol. 15(3):259-267, published online Mar. 2, 2008.

Skottman, et al., Culture Conditions for Human Embryonic Stem Cells, Reproduction 132(5):691-698, Nov. 2006.

Soldner, et al., Parkinson's Disease Patient-Derived Induced Pluripotent Stem Cells Free of Viral Reprogramming Factors, Cell 136(5):964-977, Mar. 6, 2009.

Sottile, et al., In vitro Osteogenic Differentiation of Human ES Cells, Cloning Stem Cells 5(2):149-155, 2003.

Spencer, et al., E-Cadherin Inhibits Cell Surface Localization of the Pro-Migratory 5T4 Oncofetal Antigen in Mouse Embryonic Stem Cells, Mol. Biol. Cell 18:2838-2851, 2007.

Spivakov, et al., Epigenetic Signatures of Stem-Cell Identity, Nat. Rev. Genet. 8(4):263-271, 2007.

Stadler, et al., Small RNAs: Keeping Stem Cells in Line, Cell. 132(4):563-566, Feb. 22, 2008.

Stadtfeld, et al., Induced Pluripotency: History, Mechanisms, and Applications, Genes & Development 24:2239-2263, 2010.

Stadtfeld, et al., Induced Pluripotent Stem Cells Generated Without Viral Integration, Science 322(5903):945-949, published online Sep. 25, 2008.

Stadtfeld, M., Defining Molecular Cornerstones During Fibroblast to iPS Cell Reprogramming in Mouse, Cell Stem Cell 2(3):230-240, Mar. 6, 2008.

Stem Cells Made to Mimic Disease, BBC News, http://newsvote.bbc.co.uk/mpapps/pagetools/print/news.bbc.co.uk/2/hi/health/7334365.stm, Apr. 7, 2008.

Stewart, et al., Mechanisms of Self-Renewal in Human Embryonic Stem Cells, Eur. J. Cancer 42(9):1257-1272, Jun. 2006.

Stojkovic, et al., Derivation, Growth and Applications of Human Embryonic Stem Cells. Reproduction 128(3):259-267, Sep. 2004.

Stoykova, et al., Mini-Oct and Oct-2c: Two Novel, Functionally Diverse murine Oct-2 Gene Products are Differentially Expressed in the CNS, Neuron 8(3):541-58, Mar. 1992.

Strelchenko, et al., Embryonic Stem Cells from Morula. Methods in Enzymology 418:93-108, 2006.

Strelchenko, N., Bovine Pluripotent Stem Cells, Theriogenology 45:131, 1996.

Suh, et al., Human Embryonic Stem Cells Express a Unique Set of microRNAs, Developmental Biology 270:488-498, 2004.

Sumi, et al., Apoptosis and Differentiation of Human Embryonic Stem Cells Induced by Sustained Activation of c-Myc, Oncogene 26(38):5564-5576, Aug. 16, 2007.

Surani, et al., A New Route to Rejuvenation, Nature 443:284-285, Sep. 21, 2006.

Swift, et al., Rapid Production of Retroviruses for Efficient Gene Delivery to Mammalian Cells Using 293T Cell-Based System, Current Protocols in Immunology 31(Supp.):10.17.14-10.17.29, 1999.

Szymczak, A., et al., Correction of Multi-Gene Deficiency in vivo Using a Single 'Self-Cleaving' 2A Peptide-Based Retroviral Vector, Nature Biotechnology 22:589-594, 2002.

Tada, et al., Nuclear Reprogramming of Somatic Cells by in vitro Hybridization With ES Cells, Current Biology 11(19):1553-58, 2001.

Takahashi, et al., Induction of Pluripotent Stem Cells From Adult Human Fibroblasts by Defined Factors, Cell. 131(5):861-72, published online Nov. 20, 2007.

Takahashi, et al., Induction of Pluripotent Stem Cells From Fibroblast Cultures, Nat. Protoc. 2(12):3081-3089, published online Nov. 29, 2007.

Takahashi, et al., Induction of Pluripotent Stem Cells From Mouse Embryonic and Adult Fibroblasts by Defined Factors, Cell 126(4):663-676, published online Aug. 10, 2006.

Takahashi, et al., Induced Pluripotent Stem Cells, Jikken Igaku (Experimental Medicine) 26(5):35-40, 2008.

Takahashi, et al., Role of ERas in Promoting Tumour-Like Properties in Mouse Embryonic Stem Cells, Nature 423:541-45, 2003.

Takahashi, K., et al., Human Induced Pluripotent Stem Cells on Autologous Feeders, PLoS One 4(12):e8067, Dec. 2, 2009.

Takeda, et al., Characterization of Dental Pulp Stem Cells of Human Tooth Germs, Journal of Dental Research 87:676-681, 2008.

Takeda, et al., Human Oct3 Gene Family: cDNA Sequences, Alternative Splicing, Gene Organization, Chromosomal Location, and Expression at Low Levels in Adult Tissues, Nucleic Acids Research 20(17):4613-4620, 1992.

Tan, et al., Changing Viral Tropism Using Immunoliposomes Alters the Stability of Gene Expression: Implications for Viral Vector Design, Mol. Med. 13(3-4):216-226, Mar.-Apr. 2007.

Tantin, et al., High-Throughput Biochemical Analysis of in vivo Location Data Reveals Novel Distinct Classes of POU5FI(Oct4)/DNA Complexes, Genome Res. 18(4):631-639, Apr. 2008.

Taranger, et al., Induction of Dedifferentiation, Genomewide Transcriptional Programming, and Epigenetic Reprogramming by Extracts of Carcinoma and Embryonic Stem Cells, Mol. Biol. Cell 16:5719-5735, 2005.

Tateno, et al., Heterogeneity of Growth Potential of Adult Rat Hepatocytes in vitro, Hepatology 31(1):65-74, 2000.

Bayer Team Makes Stem Cells From Skin, The Japan Times, Apr. 12, 2008. Available at http://search.japantimes.co.jp/cgi-bin/nn20080412a5.html. Accessed May 19, 2009.

Thomson, et al., Embryonic Stem Cell Lines Derived From Human Blastocysts, Science 282(5391):1145-1147, Erratum in: Science 282(5395):1827, Dec. 4, 1998.

Thomson, et al., Isolation of a Primate Embryonic Stem Cell Line, Proc. Natl. Acad. Sci. 92:7844,1995.

The Top 10 Everything of 2008—1. First Neurons Created from ALS Patients, Time, Available at http://www.time.com/time/specials/2008/top10/article/0,30583,1855948_1863993,00.html. Accessed Dec. 15, 2008.

Tokusumi, T., et al., Recombinant Sendai Viruses Expressing Different Levels of a Foreign Reporter Gene, Virus Research 86:33-38, 2002.

Tokuzawa, et al., Utilization of Digital Differential Display to Identify Novel Targets of Oct3/4. In: Turksen, K., ed., Embryonic Stem Cell Protocols: vol. I: Isolation and Characterization. Humana Press; 2nd ed., Feb. 15, 2006, pp. 223-231.

Tokuzawa, et al., Fbx15 Is a Novel Target of Oct3/4 but is Dispensible for Embryonic Stem Cell Self-Renewal and Mouse Development, Mol. Cell Biol. 23(8):2699-2718, 2003.

Trompeter, et al., Rapid and Highly Efficient Gene Transfer into Natural Killer Cells by Nucleofection, J. Immunol. Methods 274(1-2):245-256, Mar. 1, 2003.

(56) References Cited

OTHER PUBLICATIONS

Troyanskaya, et al., Nonparametric Methods for Identifying Differentially Expressed Genes in Microarray Data, Bioinformatics 18(11):1454-1461, 2002.
Tsai, et al., In vivo Immunological Function of Mast Cells Derived From Embryonic Stem Cells: An Approach for the Rapid Analysis of Even Embryonic Lethal Mutations in Adult Mice in vivo, Proc. Natl. Acad. Sci. USA 97(16):9186-9190, Aug. 1, 2000.
Tsubooka, et al., Roles of Sall4 in the Generation of Pluripotent Stem Cells From Blastocysts and Fibroblasts, Genes Cells 4(6):683-694, Jun. 2009; Epub May 19, 2009.
Tsunoda, Y., et al., The Recent Progress on Nuclear Transfer in Mammals, Zoological Science 17:1177-1184, 2000.
Tzukerman, et al., Identification of a Novel Transcription factor Binding Element Involved in the Regulation by Differentiation of the Human Telomerase (hTERT) Promoter, Mol. Biol. Cell. 11(12):4381-4391, Dec. 2000.
Ulloa-Montoya, et al., Comparative Transcriptome Analysis of Embryonic and Adult Stem Cells With Extended and Limited Differentiation Capacity, Genome Biol. 8(8):R163, 2007.
Vallier, et al., Activin/Nodal and FGF Pathways Cooperate to Maintain Pluripotency of Human Embryonic Stem Cells, J. Cell Sci. 118(Pt 19):4495-4509, Oct. 1, 2005.
van Viet, et al., Human KLF17 is a New Member of the Sp/KLF Family of Transcription Factors, Genomics 87(4):474-482, Apr. 2006; Epub Feb. 7, 2006.
Vennstrom, et al., Isolation and Characterization of c-myc, a Cellular Homolog of the Oncogene (v-myc) of Avian Myelocytomatosis Virus Strain 29, J. of Virol. 42(3):773-779, Jun. 1982.
Vermeesch, et al., Guidelines for Molecular Karyotyping in Constitutional Genetic Diagnosis, Eur. J. Hum. Genet. 15(11):1105-1114, Nov. 2007.
Verrey, et al., CATs and HATs: The SLC7 Family of Amino Acid Transporters, Pflugers Archive-European Journal of Physiology, DOI 10.1007/s00424-003-1086-Z, pp. 1-23, published online Jun. 11, 2003.
Vintersten, et al., Mouse in Red: Red Fluorescent Protein Expression in Mouse ES Cells, Embryos, and Adult Animals, Genesis 40:241-46, 2004.
Viswanathan, et al., Selective Blockade of MicroRNA Processing by Lin28, Science 320:97-100, 2008.
Vogel, G., Breakthrough of the Year. Reprogramming Cells, Science 322(5909):1766-1767, Dec. 19, 2008.
Wadia, et al., Protein Transduction Technology, Curr. Opin. Biotechnol. 13:52-56, 2002.
Wagner, et al., Mesenchymal Stem Cell Preparations—Comparing Apples and Oranges, Stem Cell Rev. 3(4):239-248, Dec. 2007.
Wakao, et al., Multilineage-Differentiating Stress-Enduring (Muse) Cells are a Primary Source of Induced Pluripotent Stem Cells in Human Fibroblasts, Available at www.pnas.org/cgi/content/short/1100816108.
Wakayama, et al., Differentiation of Embryonic Stem Cell Lines Generated From Adult Somatic Cells by Nuclear Transfer, Science 292:740-43, 2001.
Wakayama, et al., Full-Term Development of Mice From Enucleated Oocytes Injected With Cumulus Cell Nuclei, Nature 394:369-374, 1998.
Wang, et al., Inhibition of Caspase-Mediated Anoikis is Critical for bFGF-Sustained Culture of Human Pluripotent Stem Cells, J. Biol. Chem. 284(49):34054-34064, Dec. 4, 2009; Epub Oct. 13, 2009.
Wang et al., A Protein Interaction Network for Pluripotency of Embryonic Stem Cells, Nature 444:364-368, 2006.
Watson, et al., Identifying Genes Regulated in a Myc-Dependent Manner, J. Biol. Chem. 277(40):36921-36930, Oct. 4, 2002.
Werbowetski-Ogilvie, et al., Characterization of Human Embryonic Stem Cells With Features of Neoplastic Progression, Nat. Biotechnol. 27(1):91-97, Jan. 2009.
Wernig, et al., c-Myc is Dispensable for Direct Reprogramming of Mouse Fibroblasts, Cell Stem Cell 2(1):10-12, published online Dec. 13, 2007.
Wernig, et al. In vitro Reprogramming of Fibroblasts into a Pluripotent ES-Cell-Like State, Nature 448:318-324, Jul. 19, 2007.
Wernig, et al., Neurons Derived From Reprogrammed Fibroblasts Functionally Integrate Into the Fetal Brain and Improve Symptoms of Rats With Parkinson's Disease, Proc. Natl. Acad. Sci. USA 105(15):5856-5861, Apr. 15, 2008.
What are adult stem Cells? Stem Cell Information. The National Institutes of Health Resource for Stem Cell Research, available at: http://stemcells.nih.gov/info/basics/basics4.asp, accessed Jun. 4, 2007.
Wilmut, et al., Viable Offspring Derived From Fetal and Adult Mammalian Cells, Nature 385:810-813, 1997.
Woltjen, et al., PiggyBac Transposition Reprograms Fibroblasts to Induced Pluripotent Stem Cells, Nature 458(7239):766-770, Mar. 1, 2009.
Wu, et al. Origins and Fates of Cardiovascular Progenitor Cells, Cell 132(4):537-543, Feb. 22, 2008.
Wu, et al., Sall4 Interacts With Nanog and Co-Occupies Nanog Genomic Sites in Embryonic Stem Cells, J. Biol., Chem., 281(34):24090-24094, 2000.
Xu, et al., BMP4 Initiates Human Embryonic Stem Cell Differentiation to Trophoblast, Nature Biotechnol. 20(12):1261-1264, Dec. 2002.
Xu, et al Random Mutagenesis Libraries: Optimization and Simplification by PCR, Biotechniques 27(6):1102, 1104, 1106, 1108, Dec. 1999.
Xu, et al., FGF and Suppression of BMP Signaling Sustain Undifferentiated Proliferation of Human ES Cells, Nat. Methods 2(3):185-190, 2005.
Yamanaka, et al., Nuclear Reprogramming to a Pluripotent State by Three Approaches Nature 465(7299):704-712, Jun. 10, 2010.
Yamanaka, et al., Mouse Sen'iga Saibo Kara Yudo Tansosei Kansaibo o Tsukuru (Induction of Pluripotent Stem Cells From Mouse Fibroblast Cultures) Tanpakushitsu Kakusan Koso (Protein, Nucleic Acid and Enzyme) 51(15):2346-51, 2006.
Yamanaka, S., An interview with . . . Shinya Yamanaka. Interview by Mary Muers. Nat. Rev. Genet. 11(6):390, Jun. 2010.
Yamanaka, S., Patient-Specific Pluripotent Stem Cells Become Even More Accessible Cell Stem Cell 7(1):1-2, Jul. 2, 2010.
Yamanaka, S., Pluripotency and Nuclear Reprogramming, Philos. Trans. R. Soc. Lond. B. Biol. Sci. 363(1500):2079-2087, Jun. 27, 2008.
Yamanaka, S., Symposium: Nuclear Reprogramming and the Control of Differentiation in Mammalian Embryos, Introduction, Reprod. Biomed Online 16(1):11-12, Jan. 2008.
Yamanaka, Pluripotency of Differentiation and miRNA, The Journal of Biochemistry 79(11):Abstract 3BT17, from the 80th Annual Meeting of the Japanese Biochemical Society, Nov. 25, 2007, along with an English language translation thereof.
Yamanaka, S., Induction of Pluripotent Stem Cells from Mouse Fibroblasts by Four Transcription Factors, Cell Prolif. 41(Suppl. 1):51-56, 2008.
Yamanaka, S., Strategies and New Developments in the Generation of Patient-Specific Pluripotent Stem Cells, Cell Stem Cell 1(1):39-49, Jun. 7, 2007.
Yamanaka, S., A Fresh Look at iPS Cells, Cell 137(1):13-17, Apr. 3, 2009.
Yamanaka, S., Ekiden to iPS Cells. Nat. Med. 15(10):1145-1148, Oct. 2009.
Yamanaka, S., Elite and Stochastic Models for Induced Pluripotent Stem Cell Generation, Nature 460(7251):49-52, Jul. 2, 2009.
Yamanaka, S., Induction of Pluripotency by Defined Factors—The History of iPS Cells, Gardner Award acceptance speech, presented on or about Oct. 29, 2009.
Yamanaka, S., Induction of Pluripotency by Defined Factors, lecture presented on or about Oct. 29, 2009.
Yamanaka, S., Induction of Pluripotent Stem Cells From Mouse Fibroblasts by Four Transcription Factors, Cell Proliferation 41(Suppl. 1):51-56, 2008.

(56) References Cited

OTHER PUBLICATIONS

Yamane, et al., Derivation of Melanocytes From Embryonic Stem Cells in Culture, Dev. Dyn. 216:450-458, 1999.
Yamashita, et al., Flk1-Positive Cells Derived From Embryonic Stem Cells Serve as Vascular Progenitors, Nature 408(6808):92-96, Nov. 2, 2000.
Yang, et al., Nuclear Reprogramming of Cloned Embryos and Its Implications for Therapeutic Cloning, Nat. Genet. 39(3):295-302, 2007.
Yee, et al. Generation of High-Titer Pseudotyped Retroviral Vectors With Very Broad Host Range, Methods Cell Biol. 43(Pt. A):99-112, 1994.
Ying, et al., BMP Induction of ID Proteins Suppresses Differentiation and Sustains Embryonic Stem Cell Self-Renewal in Collaboration With STAT3, Cell 115:281-292, 2003.
Ying, et al., The MicroRNA: Overview of the RNA Gene That Modulates Gene Functions, Methods in Molecular Biology, MicroRNA Protocols 342:1-18, 2006.
Yoshida, et al. Hypoxia Enhances the Generation of Induced Pluripotent Stem Cells, Cell Stem Cell 5(3):237-241, Sep. 4, 2009; Epub Aug. 27, 2009.
Yoshida, et al., Recent Stem Cell Advances: Induced Pluripotent Stem Cells for Disease Modeling and Stem Cell-Based Regeneration, Circulation 122(1):80-87, Jul. 6, 2010.
Yu, et al., Induced Pluripotent Stem Cell Lines Derived From Human Somatic Cells, Science 318(5858):1917-1920, published online Nov. 20, 2007.
Yu, et al., Human Induced Pluripotent Stem Cells Free of Vector and Transgene Sequences, Science 324:797-801, Mar. 2009.
Yuasa, et al. Transient Inhibition of BMP Signaling by Noggin Induces Cardiomyocyte Differentiation of Mouse Embryonic Stem Cells, Nat. Biotechnol. 23(5):607-611, May 2005.
Zhan, et al., Conservation and Variation of Gene Regulation in Embryonic Stem Cells Assessed by Comparative Genomics, Cell Biochem. Biophys. 43(3):379-405, 2005.
Zhang, et al. In vitro Differentiation of Transplantable Neural Precursors From Human Embryonic Stem Cells, Nat. Biotechnol. 19:1129-1133, Dec. 2001.
Zhang, et al., MicroRNA: A New Player in Stem Cells, J. Cell. Phys. 209:266-269, 2006.
Zhao, et al. Mechanisms and Functional Implications of Adult Neurogenesis, Cell 132(4):645-660, Feb. 22, 2008.
Zhao, et al., Two Supporting Factors Greatly Improve the Efficiency of Human iPSC Generation Cell Stem Cell 3:475-479, 2008.
Zhou, et al., Generation of Induced Pluripotent Stem Cells Using Recombinant Proteins, Cell Stem Cell 4:381-384, 2009.
Ziegler, et al., The Cationic Cell-Penetrating Peptide CPP$^{TAT}$ Derived From the HIV-1 Protein TAT is Rapidly Transported into Living Fibroblasts: Optical, Biophysical, and Metabolic Evidence, Biochemistry 44:138-148, published online Dec. 14, 2004.
Extended European Search Report for European Patent Application No. 09738908.4, dated Jan. 28, 2013.
Wei et al., "Sumoylation of Oct4 Enhances Its Stability, DNA Binding, and Transactivation," *Journal of Biological Chemistry*, vol. 282(29), pp. 21551-21560 (2007).
Office Action issued in Japanese Patent Application No. 2010-506477, on Apr. 9, 2013.
Tomioka et al., "Identification of Sox-2 regulatory region which is under the control of Oct-3/4-Sox-2 complex," *Nucleic Acids Research*, vol. 30(14), pp. 3202-3213 (2002).
Zhu et al., "Three-Color Flow Cytometry Analysis of Tricistronic Expression of eBFP, eGFP, and eYFP Using EMCV-IRES Linkages," *Cytometry*, vol. 37, pp. 51-59 (1999).
Extended European Search Report mailed on Feb. 21, 2012 in corresponding European patent app. No. 09763772.2 in 6 pages.
Notification of the Second Office Action dated Feb. 24, 2012, issued in connection with Chinese Patent Application No. 200880000834.5, 9 pages.
Notice of Opposition dated May 3, 2012, issued in connection with European Patent Application No. 06834636.0, 32 pages.
Examination Report dated Sep. 28, 2011, issued in connection with European Patent Application No. 07856194.1.
European Office Action for Application No. 07856194.1 dated May 9, 2012.
Examination report dated Dec. 11, 2012 and issued to related European application No. 10154817.0.
Examination Report dated Oct. 23, 2012, issued in connection with European Patent Application No. 10154819.6.
Office Action issued in connection with European Patent Application No. EP 10154819.6, Nov. 8, 2013.
Examination Report dated Oct. 15, 2012, issued in connection with European Patent Application No. 10154821.2.
Office Action issued in GB0922013.8, dated Aug. 4, 2011.
Office Action mailed on Mar. 13, 2012, issued in connection with Japanese Patent Application No. 2007-550210.
Examination Report dated Feb. 9, 2012, issued in connection with New Zealand Patent Application No. 582018.
Adewumi, et al., Characterization of Human Embryonic Stem Cell Lines by the International Stem Cell Initiative, Nat. Biotechnol. 25(7):803-16, 2007.
Aoi, T., et al., Generation of Pluripotent Stem Cells From Adult Mouse Liver and Stomach Cells, Science, vol. 321, pp. 699-702, Corrected Aug. 1, 2008.
BioPorterTM Protein Delivery Reagent From www.biocarta.com [2002].
Bosman et al., Progress Toward the Clinical Application of Autologous Induced Pluripotent Stem Cells and Gene Repair Therapy for Treatment of Familial Hypercholesterolemia. The International Liver Congress 2011, 2011, abstract.
Cosmo Bio News 49:5, 2005 (catalog of ES cell culture medium).
Cowan et al., Nuclear Reprogramming of Somatic Cells After Fusion With Human Embryonic Stem Cells, Science 309:1369-73, 2005.
Cyranoski et al., Simple Switch Turns Cells Embryonic (Correction), Nature, Jun. 21, 2007, vol. 447, pp. 897.
Hotta et al., "Retroviral Vector Silencing During iPS Cell Induction: An Epigenetic Beacon that Signals Distinct Pluripotent States," Journal of Cellular Biochemistry, vol. 105, pp. 940-948 (2008).
Jiang, et al., In vitro Derivation of Functional Insulin-Producing Cells From Human Embryonic Stem Cells, Cell Res. 17(4):333-344, Apr. 2007.
Kehat et al. Human embryonic stem cells can differentiate into myocytes with structural and functional properties of cardiomyocytes. J Clin Invest. Aug. 2001; 108(3):407-14.
Lanza et al. (Eds.) Essentials of Stem Cell Biology. Elsevier Academic Press. 2006. (Table of Contents only).
Mimeault et al. Concise Review: Recent Advances on the Significance of Stem Cells in Tissue Regeneration and Cancer Therapies. Stem Cells, 2006, vol. 24, pp. 2319-2345.
Oshima et al., "Mechanosensitive Hair Cell-like Cells from Embryonic and Induced Pluripotent Stem Cells," Cell, vol. 141, pp. 704-716 (May 14, 2010).
Park, In-Hyun, et al., "Reprogramming of Human Somatic Cells to Pluripotency With Defined Factors," Nature 451:141-146, 2008.
Perkins et al. Anemia and perinatal death result from loss of the murine ecotropic retrovirus receptor mCAT-1.Genes & Development, 1997, vol. 11, pp. 914-925.
The Japan Times. Bayer team makes stem cells from skin. Apr. 12, 2008. Available at http://search.japantimes.co.jp/cgi-bin/nn20080412a5.html. Accessed May 19, 2009.
Ulloa-Montoya et al., "Culture Systems for Pluripotent Stem Cells," Journal of Bioscience and Bioengineering, vol. 100(1), pp. 12-27 (2005).
Vector (in biotechnology), IUPAC Compendium of Chemical Terminology, 2nd Edition (1997).
Watanabe, et al., A Rock Inhibitor Permits Survival of Dissociated Human Embryonic Stem Cells, Nat. Biotechnol. 25:681-686, 2007.
Yamanaka, et al. "Kekkan," Japanese Journal of Circulation Research, vol. 28(2), pp. 33-38 (2005).
Ying, microRNA, Jikken Purotokoru (microRNA Experimental Protocol), Yodosha Col. Ltd. 2008 pp. 2035.
Zhao et al., "A human peripheral blood monocyte-derived subset acts as pluripotent stem cells," PNAS, vol. 100(5), pp. 2426-2431 (Mar. 4, 2003).
Zhou et al., "Adenoviral Gene Delivery Can Reprogram Human Fibroblasts to Induced Pluripotent Stem Cells," Stem Cells, vol. 27, pp. 2667-2674 (2009).

\* cited by examiner

Fig. 13

| Regions | sequences |
|---|---|
| G3PDH | ACC ACA GTC CAT GCC ATC AC |
| | TCC ACC ACC CTG TTG CTG TA |
| Nanog | AGG GTC TGC TAC TGA GAT GCT |
| | CAA CAC CTG GTT TTT CTG CCA CCG |
| Rex1 | ACGAGTGGCAGTTTCTTCTTGGGA |
| | TATGACTCACTTCCAGGGGGCACT |
| ECAT1 | TGT GGG GCC CTG AAA GGC GAG CTG AGA T |
| | ATG GGC CGC CAT ACG ACG ACG CTC AAC T |
| ERas | ACT GCC CCT CAT CAG ACT GCT ACT |
| | CAC TGC CTT GTA CTC GGG TAG CTG |
| Fbx15 | GTT GGA ATC TGC TTC TAC AG |
| | CTT CAC CAA GAT TTC CGA TG |
| Esg1 | GAA GTC TGG TTC CTT GGC AGG ATG |
| | ACT CGA TAC ACT GGC CTA GC |
| Oct3/4 | CTG AGG GCC AGG CAG GAG CAC GAG |
| | CTG TAG GGA GGG CTT CGG GCA CTT |
| Sox2 | GGT TAC CTC TTC CTC CCA CTC CAG |
| | TCA CAT GTG CGA CAG GGG CAG |
| Klf4 | CAC CAT GGA CCC GGG CGT GGC TGC AGA AAA |
| | TTA GGC TGT TCT TTT CCG GGG CCA CGA |
| c-Myc | CAG AGG AGG AAC GAG CTG AAG CGC |
| | TTA TGC ACC AGA GTT TCG AAG CTG TTC G |
| O-1 | CGG AAT TCA AGG AGC TAG AAC AGT TTG CC |
| | CTG AAG GTT CTC ATT GTT GTC G |
| O-2 | GAT CAC TCA CAT CGC CAA TC |
| | CTG GGA AAG GTG TCC TGT AGC C |
| K | GCG GGA AGG GAG AAG ACA CTG CGT C |
| | TAG GAG GGC CGG GTT GTT ACT GCT |
| K-S | CCT TAC ACA TGA AGA GGC ACT TT |
| | CAG CTC CGT CTC CAT CAT GTT AT |
| M | ACA CTC CCC CAA CAC CAG GAC GTT T |
| | GCT CGC CCA AAT CCT GTA CCT CGT CCG AT |
| | GAG ATG AGC CCG ACT CCG ACC TCT T |
| 1 | AGG TGC AGG CTG CCT ATC |
| | TTA GCC AGA AGT CAG ATG CTC |
| 2 | TGG CGT AAT CAT GGT CAT AG |
| | GCA ACG CAA TTA ATG TGA GTT AG |
| 3 | CTG GAT CCG CTG CAT TAA TGA |
| | CCG AGC GCA GCG AGT CA |

Fig. 14

| Regions | Sequences |
|---|---|
| 4 | GCC TTA TCC GGT AAC TAT CGT |
| | GCA CCG CCT ACA TAC CTC |
| 5 | AGT TGC CTG ACT CCC CGT CGT G |
| | GGA GCC GGT GAG CGT GGG TC |
| 6 | CCG ATC GTT GTC AGA AGT AAG TTG |
| | TCA CAG AAA AGC ATC TTA CGG A |
| 7 | GAA AAG TGC CAC CTG GTC GAC ATT |
| | GGG CCA TTT ACC GTA AGT TAT GTA |
| 8 | TAT CAT ATG CCA AGT ACG C |
| | TAG ATG TAC TGC AAG TAG GAA |
| 9 | TCT GAC TGA CCG CGT TAC T |
| | AGA AAA GAA ACG AGC CGT CAT T |
| 10 | GGG GGC TGC GAG GGG AAC AAA |
| | GCC GGG CCG TGC TCA GCA ACT |
| 11 | GCG AGC CGC AGC CAT TGC CTT TTA |
| | CCC AGA TTT CGG CTC CGC CAG AT |
| Nanog-reporter | TGG GAT CCC TAT GCT ACT CCG TCG AAG TTC |
| | CTA GGC AAA CTG TGG GGA CCA GGA AGA C |
| Fbx15-reporter | TGG TCC AAC ATC TTA TAC ACA GTA ATG A |
| | GTG GAA CTC CCT TCT AGC CCT CTA TCC C |
| | AAT GGG CTG ACC GCT TCC TCG TGC TT |

# METHOD OF MAKING INDUCED PLURIPOTENT STEM CELLS

CROSS-REFERENCE TO RELATED APPLICATIONS

This application is a divisional of U.S. patent application Ser. No. 12/733,118, filed May 3, 2010, which is a U.S. National Phase of International Patent Application No. PCT/JP2009/058873, filed May 1, 2009, which claims the benefit of U.S. Provisional Patent Application No. 61/071,508, filed May 2, 2008; U.S. Provisional Patent Application No. 61/136,246, filed Aug. 21, 2008; U.S. Provisional Patent Application No. 61/136,615, filed Sep. 19, 2008; and U.S. Provisional Patent Application No. 61/193,363, filed Nov. 21, 2008. The entire contents of these prior related applications are hereby incorporated by reference.

TECHNICAL FIELD

The present invention relates to a method of reprogramming a somatic cell and producing an induced pluripotent stem cell.

BACKGROUND ART

Established from human or mouse early embryos, embryonic stem cells (ES cells) are capable of being cultured for a long time while maintaining their potential for differentiating into all types of cells found in a living organism. With this feature, human ES cells are expected to serve for cell transplantation therapies for many diseases, including Parkinson's disease, juvenile diabetes, and leukemia. However, ES cell transplantation poses the problem of causing rejections as with organ transplantation. Additionally, not a few people oppose the use of ES cells established with the destruction of a human embryo, from an ethical viewpoint.

If the dedifferentiation of a patient's somatic cells is induced to establish cells possessing pluripotency and proliferating capability similar to those of an ES cell (herein these cells are referred to as "induced pluripotent stem cells" (iPS cells), and sometimes referred to as "embryonic stem cell-like cells" or "ES-like cells"), the established cells will be useful as ideal pluripotent cells that do not pose the problems of rejections and ethical issues. In recent years, it has been reported that iPS cells can be produced from mouse and human differentiated cells, arousing great attention (International Patent Application Publication No. WO2007/69666; Cell, 126, pp. 663-676, 2006; Cell, 131, pp. 861-872, 2007; Science, 318, pp. 1917-1920, 2007; Nature, 451, pp. 141-146, 2008).

All these methods comprise the step of introducing a plurality of particular nuclear reprogramming factors (e.g., in Cell, 126, pp. 1-14, 2006, 4 factors are used: Oct3/4, Sox2, Klf4, and c-Myc) into a somatic cell to achieve reprogramming, which step involves the use of a retrovirus or a lentivirus for the purpose of introducing the genes that encode the nuclear reprogramming factors into a somatic cell efficiently. However, since gene delivery using a viral vector involves safety issues, there is a demand for developing a method of producing iPS cells without using a viral vector.

SUMMARY OF THE INVENTION

Technical Problem

It is an object of the present invention to provide a method of producing an iPS cell by reprogramming a somatic cell without using a viral vector such as a retrovirus.

Solution to Problem

The present inventors extensively investigated to solve the problems described above, and found that an iPS cell can be produced by introducing genes that encode reprogramming factors into a somatic cell by means of a non-viral expression vector such as a plasmid vector, and that a safe iPS cell can be obtained from a somatic cell by the method. The present invention has been developed on the basis of these findings.

Accordingly, the present invention provides a method of producing an induced pluripotent stem cell, comprising the step of introducing at least one kind of non-viral expression vector incorporating at least one gene that encodes a reprogramming factor into a somatic cell.

In a preferred embodiment, the present invention provides the above-described method wherein the vectors are non-viral expression vectors autonomously replicable outside a chromosome; and the above-described method wherein the vector is a plasmid vector.

In another preferred embodiment, the present invention provides the above-described method wherein the gene that encodes a reprogramming factor is one of genes selected by a method of screening for nuclear reprogramming factors described in WO 2005/80598 or a combination of a plurality of such genes; and the above-described method wherein the gene that encodes a reprogramming factor is one or more kinds of genes selected from the group consisting of an Oct family gene, a Klf family gene, a Sox family gene, a Myc family gene, a Lin family gene, and the Nanog gene, preferably a combination of two kinds of genes, more preferably a combination of three kinds of genes, particularly preferably a combination of four or more kinds of genes.

More preferable combinations are (a) a combination of two kinds of genes consisting of an Oct family gene and a Sox family gene; (b) a combination of three kinds of genes consisting of an Oct family gene, a Klf family gene, and a Sox family gene; (c) a combination of four kinds of genes consisting of an Oct family gene, a Klf family gene, a Sox family gene, and a Myc family gene; (d) a combination of four kinds of genes consisting of an Oct family gene, a Sox family gene, a Lin family gene, and the Nanog gene; (e) a combination of six kinds of genes consisting of an Oct family gene, a Klf family gene, a Sox family gene, a Myc family gene, a Lin family gene, and the Nanog gene; and the like. Furthermore, it is also preferable to include the TERT gene and/or the SV40 Large T antigen gene in the combination. As the case may be, it is preferable to exclude Klf family genes.

Particularly preferred combinations thereof are a combination of two kinds of genes consisting of Oct3/4 and Sox2; a combination of three kinds of genes consisting of Oct3/4, Klf4, and Sox2; a combination of four kinds of genes consisting of Oct3/4, Klf4, Sox2, and c-Myc; a combination of four kinds of genes consisting of Oct3/4, Sox2, Lin28, and Nanog; and a combination of six kinds of genes consisting of Oct3/4, Klf4, Sox2, c-Myc, Lin28, and Nanog. It is also preferable to include the TERT gene and/or the SV40

Large T antigen gene in these combinations. As the case may be, it is preferable to exclude Klf4.

In another preferred embodiment, the present invention provides the above-described method wherein the number of kinds of non-viral expression vectors introduced into a somatic cell is 1, 2, 3, or 4; the above-described method wherein the genes that encode reprogramming factors are a combination of three kinds of genes consisting of an Oct family gene, a Klf family gene, and a Sox family gene, and these genes are incorporated in one kind of non-viral expression vector; the above-described method wherein the genes that encode nuclear reprogramming factors are a combination of four kinds of genes consisting of an Oct family gene, a Klf family gene, a Sox family gene, and a Myc family gene, and the Oct family gene, the Klf family gene, and the Sox family gene are incorporated in one kind of non-viral expression vector; the above-described method wherein the Oct family gene, the Klf family gene, and the Sox family gene are incorporated in one kind of non-viral expression vector in this order in the orientation from the 5' to 3' end; and the above-described method wherein the Oct family gene, the Klf family gene, and the Sox family gene are incorporated in one kind of non-viral expression vector with an intervening sequence enabling polycistronic expression.

In another preferred embodiment, the present invention provides the above-described method wherein two or more kinds of the above-described non-viral expression vectors are concurrently introduced into a somatic cell; the above-described method wherein the genes that encode reprogramming factors are a combination of four kinds of genes consisting of an Oct family gene, a Klf family gene, a Sox family gene, and a Myc family gene, and a first non-viral expression vector incorporating three or less kinds of genes selected from among the four kinds of genes, and a second non-viral expression vector incorporating the remaining gene(s) out of the four kinds of genes are concurrently introduced into a somatic cell; the above-described method wherein the three or less kinds of genes are an Oct family gene, a Klf family gene, and a Sox family gene, and the remaining gene is a Myc family gene; the above-described method wherein the three or less kinds of genes are Oct3/4, Klf4, and Sox2, and the remaining gene is c-Myc; and the above-described method wherein introduction of the non-viral expression vector into a somatic cell is repeatedly performed twice or more.

In a particularly preferred embodiment, the present invention provides the above-described method wherein a first non-viral expression vector harboring Oct3/4, Klf4, and Sox2, and a second non-viral expression vector harboring c-Myc are introduced into a somatic cell; the above-described method wherein a first non-viral expression vector harboring Oct3/4, Klf4, and Sox2 in this order in the orientation from the 5' to 3' end, and a second non-viral expression vector harboring c-Myc are introduced into a somatic cell; the above-described method wherein Oct3/4, Klf4, and Sox2 are ligated in this order in the orientation from the 5' to 3' end with an intervening sequence enabling polycistronic expression and inserted into the first non-viral expression vector; the above-described method wherein the first non-viral expression vector and the second non-viral expression vector are concurrently introduced into a somatic cell; and the above-described method wherein the introduction is repeatedly performed twice or more. Also provided is the above-described method wherein whole or prat of the at least one non-viral expression vector introduced is substantially not integrated in the chromosome.

In another preferred embodiment, the present invention provides the above-described method wherein the somatic cell is a somatic cell of a mammal, including a human, preferably a human or mouse somatic cell, particularly preferably a human somatic cell; the above-described method wherein the somatic cell is a fetal human cell or a somatic cell derived from an adult human; and the above-described method wherein the somatic cell is a somatic cell collected from a patient.

In another aspect, the present invention provides an induced pluripotent stem cell that can be obtained by the above-described method. In a preferred embodiment, the present invention also provides an induced pluripotent stem cell wherein all or some of the at least one non-viral expression vector introduced is substantially not integrated in the chromosome.

Also provided are the above-described induced pluripotent stem cell wherein the somatic cell is a somatic cell of a mammal, including a human, preferably a human or mouse somatic cell, particularly preferably a human somatic cell; the above-described induced pluripotent stem cell wherein the somatic cell is a fetal human cell or a somatic cell derived from an adult human; and the above-described induced pluripotent stem cell wherein the somatic cell is a somatic cell collected from a patient.

A non-viral expression vector, preferably a plasmid vector, for use in the above-described method of producing an induced pluripotent stem cell, incorporating at least one gene that encodes a reprogramming factor, is also provided by the present invention.

A somatic cell induced and differentiated from the above-described induced pluripotent stem cell is also provided by the present invention.

The present invention also provides a stem cell therapy comprising the step of transplanting to a patient a somatic cell obtained by differentiation induction of an induced pluripotent stem cell obtained by the above-described method using a somatic cell separated from the patient.

The present invention further provides a method of evaluating the physiological activities and toxicities of compounds, drugs, poisonous substances and the like using various cells obtained by differentiation induction of an induced pluripotent stem cell obtained by the above-described method.

Advantageous Effects of Invention

Produced without using a vector to be integrated into a chromosome, such as a retrovirus, the induced pluripotent stem cell provided by the present invention is advantageous in that tumorigenesis and other problems do not arise in the somatic cells and tissues obtained by differentiating the induced pluripotent stem cell. In a preferred embodiment of the present invention, in the induced pluripotent stem cell produced by the method of the present invention, all or some of the at least one non-viral expression vector introduced is episomally present, substantially not integrated in the chromosome. Therefore, the method of the present invention makes it possible to prepare a highly safe induced pluripotent stem cell from, for example, a patient's somatic cell, and the cells obtained by differentiating this cell (e.g., myocardial cells, insulin-producing cells, or nerve cells and the like) can be safely used for stem cell transplantation therapies for a broad range of diseases, including heart failure, insulin-dependent diabetes, Parkinson's disease and spinal injury.

BRIEF DESCRIPTION OF DRAWINGS

In FIG. 1, the Phase columns show phase-contrast images, and the GFP columns show GFP-positive colonies.

FIGS. 13 and 14 show the primers used for PCR in Examples 1 to 3.

DESCRIPTION OF EMBODIMENTS

Figure 1:
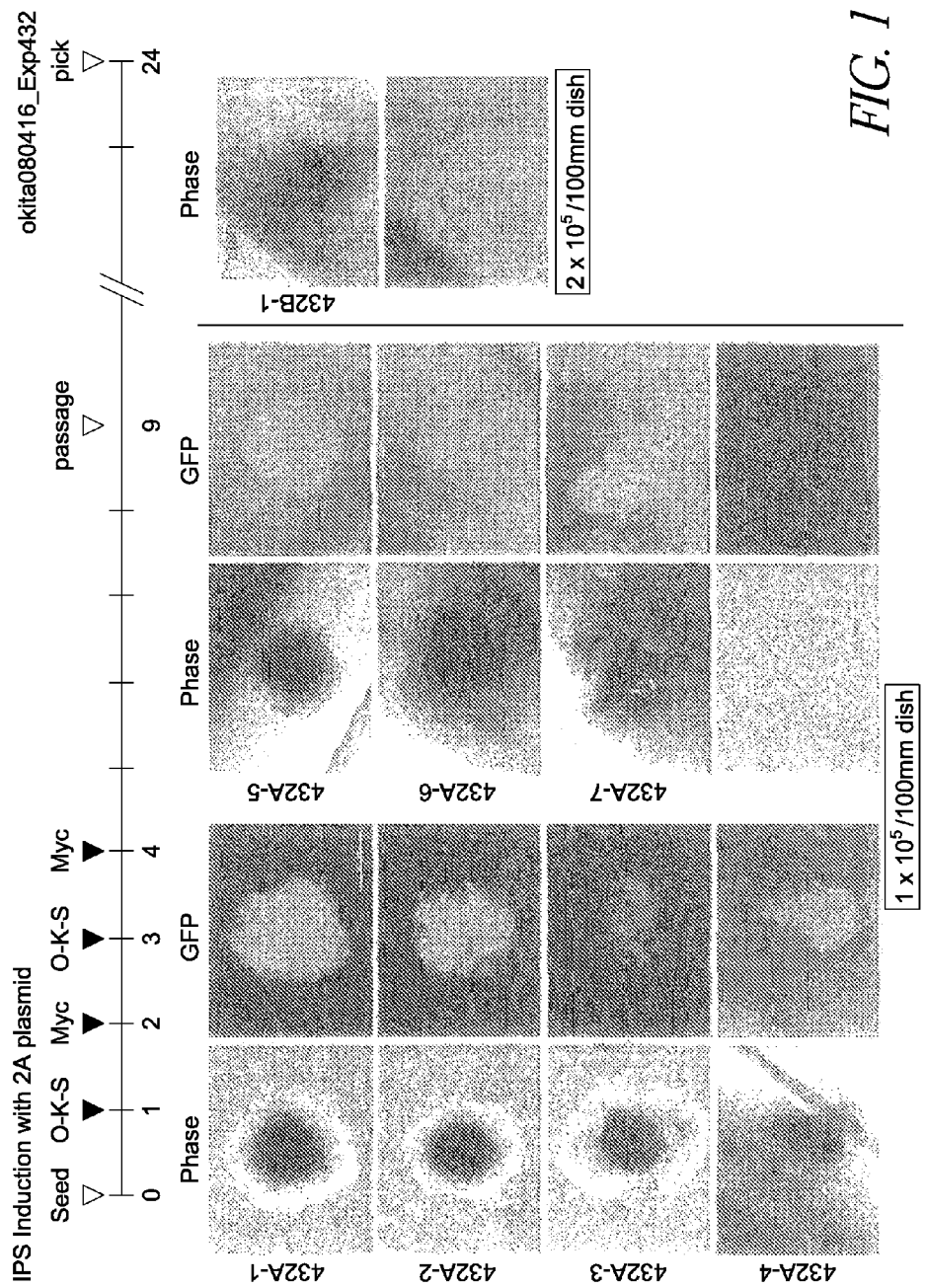
FIG. 1 shows a time course protocol for transfecting a somatic cell (MEF) with Oct3/4, Klf4, Sox2, and c-Myc using plasmids according to the method of the present invention, results of seven independent tests (left photographs, 432A-1 to 432A-7: cell density $1\times10^6$ cells/100 mm dish) and results of another test (right photographs, 432B-1: cell density $2\times10^5$ cells/100 mm dish). The lowermost panels in the center show control results (no transfection).

The method of the present invention is intended to produce an induced pluripotent stem cell, comprising the step of introducing at least one kind of non-viral expression vector incorporating at least one gene that encodes a reprogramming factor into a somatic cell. The non-viral expression vector is preferably an expression vector autonomously replicable outside a chromosome, more preferably a plasmid expression vector.

As an example of a means for identifying a nuclear reprogramming factor, a nuclear reprogramming factor screening method described in WO 2005/80598 can be utilized. All disclosures therein are incorporated herein by reference. Those skilled in the art are able to screen for nuclear reprogramming factors, and to utilize them for the method of the present invention, by referring to the aforementioned publication. It is also possible to identify nuclear reprogramming factors using a method modified or altered from the above-described screening method.

Some examples of combinations of genes that encode reprogramming factors are disclosed in WO2007/69666. All disclosures therein are incorporated herein by reference. Those skilled in the art are able to choose genes that can suitably be used in the method of the present invention as appropriate by referring to the aforementioned publication. Other examples of combinations of genes that encode reprogramming factors are given in Science, 318, pp. 1917-1920, 2007, WO2008/118820 and the like. Therefore, those skilled in the art are able to understand the diversity of combinations of genes that encode nuclear reprogramming factors; by utilizing a nuclear reprogramming factor screening method described in WO 2005/80598, appropriate combinations of genes other than the combinations described in WO2007/69666 and Science, 2007 (supra) can be utilized in the method of the present invention.

Preferable genes that encode reprogramming factors include one or more kind of genes selected from the group consisting of an Oct family gene, a Klf family gene, a Sox family gene, a Myc family gene, a Lin family gene, and the Nanog gene, preferably a combination of two kinds of genes, more preferably of three kinds of genes, and particularly preferably of four kinds of genes.

Examples of Oct family genes, Klf family genes, Sox family genes, and Myc family genes are given in WO2007/69666. Likewise, for Lin family genes, those skilled in the art are likewise able to extract a family gene. For example, as examples of Lin family genes, Lin28 and Lin28B may be included.

The nuclear reprogramming factor provided by the present invention comprises at least a combination of gene products of an Oct family gene, a Klf family gene, and a Myc family gene, for example, a combination of gene products of Oct3/4, Klf4, and c-Myc. Examples of the Oct family gene include, for example, Oct3/4, Oct 1A, Oct6, and the like. Oct3/4 is a transcription factor belonging to the POU family, and is reported as a marker of undifferentiated cells (K. Okamoto et al., Cell, 60, pp 461-72, 1990). Oct3/4 is also reported to participate in the maintenance of pluripotency (J. Nichols et al., Cell, 95, pp 379-91, 1998). Examples of the Klf family gene include Klf1, Klf2, Klf4, Klf5 and the like. Klf4 (Kruppel like factor-4) is reported as a tumor repressing factor (A. M. Ghaleb et al., Cell Res., 15, pp 92-6, 2005). Examples of the Myc family gene include c-Myc, N-Myc, L-Myc and the like. c-Myc is a transcription control factor involved in differentiation and proliferation of cells (S. Adhikary, M. Eilers, Nat. Rev. Mol. Cell Biol., 6, pp. 635-45, 2005), and is also reported to be involved in the maintenance of pluripotency (P. Cartwright et al., Development, 132, pp. 885-96, 2005). The NCBI accession numbers of the genes of the families other than Oct3/4, Klf4 and c-Myc are as follows:

TABLE 1

|  |  | Mouse | Human |
|---|---|---|---|
| Klf1 | Kruppel-like factor 1 (erythroid) | NM_010635 | NM_006563 |
| Klf2 | Kruppel-like factor 2 (lung) | NM_008452 | NM_016270 |
| Klf5 | Kruppel-like factor 5 | NM_009769 | NM_001730 |
| c-Myc | myelocytomatosis oncogene | NM_010849 | NM_002467 |

TABLE 1-continued

|  |  | Mouse | Human |
|---|---|---|---|
| N-Myc | v-Myc myelocytomatosis viral related oncogene, neuroblastoma derived (avian) | NM_008709 | NM_005378 |
| L-Myc | v-Myc myelocytomatosis viral oncogene homolog 1, lung carcinoma derived (avian) | NM_008506 | NM_005376 |
| Oct1A | POU domain, class 2, transcription factor 1 | NM_198934 | NM_002697 |
| Oct6 | POU domain, class 3, transcription factor 1 | NM_011141 | NM_002699 |

The nuclear reprogramming factor of the present invention may comprise a gene product other than the aforementioned three kinds of gene products. An example of such gene product includes a gene product of a Sox family gene. Examples of the Sox family gene include, for example, Sox1, Sox3, Sox7, Sox15, Sox17 and Sox18, and a preferred example includes Sox2. A nuclear reprogramming factor comprising at least a combination of the gene products of four kinds of genes, an Oct family gene (for example, Oct3/4), a Klf family gene (for example, Klf4), a Myc family gene (for example, c-Myc), and a Sox family gene (for example, Sox2) is a preferred embodiment of the present invention from a viewpoint of reprogramming efficiency, and in particular, a combination of a gene product of a Sox family gene is sometimes preferred to obtain pluripotency. Sox2, expressed in an early development process, is a gene encoding a transcription factor (A. A. Avilion et al., Genes Dev., 17, pp. 126-40, 2003). The NCBI accession numbers of Sox family genes other than Sox2 are as follows.

TABLE 2

|  |  | Mouse | Human |
|---|---|---|---|
| Sox1 | SRY-box containing gene 1 | NM_009233 | NM_005986 |
| Sox3 | SRY-box containing gene 3 | NM_009237 | NM_005634 |
| Sox7 | SRY-box containing gene 7 | NM_011446 | NM_031439 |
| Sox15 | SRY-box containing gene 15 | NM_009235 | NM_006942 |
| Sox17 | SRY-box containing gene 17 | NM_011441 | NM_022454 |
| Sox18 | SRY-box containing gene 18 | NM_009236 | NM_018419 |

More preferable combinations include, but are not limited to, (a) a combination of two kinds of genes consisting of an Oct family gene and a Sox family gene;
(b) a combination of three kinds of genes consisting of an Oct family gene, a Klf family gene, and a Sox family gene;
(c) a combination of four kinds of genes consisting of an Oct family gene, a Klf family gene, a Sox family gene, and a Myc family gene;
(d) a combination of four kinds of genes consisting of an Oct family gene, a Sox family gene, a Lin family gene, and the Nanog gene;
(e) a combination of six kinds of genes consisting of an Oct family gene, a Sox family gene, a Klf family gene, a Myc family gene, a Lin family gene, and the Nanog gene; and the like.

All these genes are present in common in mammals, including humans. Genes derived from optionally chosen mammals (e.g., humans, mice, rats, bovines, sheep, horses, monkeys) can be used in the present invention. In addition to wild-type gene, mutant genes whose translation products have several (e.g., 1 to 10, preferably 1 to 6, more preferably 1 to 4, more preferably 1 to 3, particularly preferably 1 or 2) amino acids substituted, inserted, and/or deleted, and possess a function similar to that of the wild type gene product, can also be utilized. For example, as c-Myc genes, the wild type, a gene encoding stable type mutant (T58A) and the like may be used. The same applies to other gene products.

In addition to the aforementioned genes, a gene that encodes a factor that induces cell immortalization may further be combined. As disclosed in WO2007/69666, for example, the TERT gene, and one or more kind of genes selected from the group consisting of the following genes: SV40 Large T antigen, HPV16 E6, HPV16 E7, and Bmi1, can be used singly, or in combination as appropriate.

Examples of preferable combinations include:
(f) a combination of five kinds of genes consisting of an Oct family gene, a Klf family gene, a Sox family gene, a Myc family gene, and the TERT gene;
(g) a combination of five kinds of genes consisting of an Oct family gene, a Klf family gene, a Sox family gene, a Myc family gene, and the SV40 Large T antigen gene;
(h) a combination of six kinds of genes consisting of an Oct family gene, a Klf family gene, a Sox family gene, a Myc family gene, the TERT gene, and the SV40 Large T antigen gene; and
(i) a combination of seven kinds of genes consisting of an Oct family gene, a Klf family gene, a Sox family gene, a Myc family gene, a Lin family gene, the Nanog gene, and the TERT gene or the SV40 Large T antigen gene.

As required, the Klf family gene may be excluded from the aforementioned combinations.

Furthermore, in addition to the aforementioned genes, one or more kind of genes selected from the group consisting of Fbx15, ERas, ECAT15-2, Tcl1, and β-catenin may be combined, and/or one or more kind of genes selected from the group consisting of ECAT1, Esg1, Dnmt3L, ECAT8, Gdf3, Sox15, ECAT15-1, Fthl17, Sal14, Rex1, UTF1, Stella, Stat3, and Grb2 may also be combined. These combinations are specifically described in WO2007/69666.

If one or more kind of these genes are already expressed in the somatic cell to be reprogrammed, the gene(s) can be excluded from the genes to be introduced. When one or more kind of these genes are introduced into a somatic cell to be reprogrammed using a vector to be integrated into a chromosome, such as a retrovirus, the remaining one or more genes can be introduced using a non-viral expression vector according to the method of the present invention. Alternatively, when one or more kind of the gene products of these genes are introduced into a nucleus by means of fused protein or nuclear microinjection, the remaining one or more genes can be introduced using a non-viral expression vector according to the method of the present invention.

Particularly preferable combinations of genes are,
(1) a combination of two kinds of genes consisting of Oct3/4 and Sox2;
(2) a combination of three kinds of genes consisting of Oct3/4, Klf4, and Sox2;
(3) a combination of four kinds of genes consisting of Oct3/4, Klf4, Sox2, and c-Myc;
(4) a combination of four kinds of genes consisting of Oct3/4, Sox2, Lin28, and Nanog;
(5) a combination of five kinds of genes consisting of Oct3/4, Sox2, c-Myc, TERT, and SV40 Large T antigen;
(6) a combination of six kinds of genes consisting of Oct3/4, Klf4, Sox2, c-Myc, TERT, and SV40 Large T antigen;
(7) a combination of six kinds of genes consisting of Oct3/4, Klf4, c-Myc, Sox2, Lin28, and Nanog;
(8) a combination of seven kinds of genes consisting of Oct3/4, Klf4, c-Myc, Sox2, Lin28, Nanog, and TERT or SV40 Large T antigen, and the like.

In addition to the aforementioned genes, a gene that encodes a factor that induces cell immortalization may further be combined. As disclosed in WO2007/69666, for example, one kind or more of genes selected from the group consisting of the TERT gene, and the following genes: HPV16 E6, HPV16 E7, and Bmi1, can be used singly, or in combination as appropriate.

When reprogramming is performed using nerve stem cells endogenously expressing Sox2 and c-Myc, or the like as a somatic cell source, a combination of two kinds of genes consisting of Oct3/4 and Klf4, or a combination of two kinds of genes consisting of Oct3/4 and c-Myc (see Nature, Published online, 29 Jun. 2008, p 1-5 (doi:10.1038/nature07061)) can also be mentioned.

In the combinations (3), (5), (6), and (7) above, L-Myc can be used in place of c-Myc.

It should be noted that combinations of genes are not limited thereto. Additionally, the scope of the present invention includes a method wherein one or more genes selected from among the above-described genes are introduced into a somatic cell using a non-viral expression vector, and the remaining gene or gene product is introduced into the somatic cell by another means. For example, it is also possible to introduce one or more genes selected from among the above-described genes into a somatic cell using a non-viral expression vector, and to introduce the remaining gene into the somatic cell using a viral vector such as retroviral vector, lentiviral vector, adenoviral vector, adeno-associated viral vector, Sendai viral vector.

When two or more kinds of genes that encode reprogramming factors are introduced into a somatic cell using non-viral expression vectors, some of the two or more kinds of genes to be introduced can be introduced into a somatic cell at a time different from that for other genes, or all kinds of genes to be introduced can be concurrently introduced into a somatic cell; however, it is preferable that all genes to be introduced be concurrently introduced into a somatic cell. When two or more kinds of different non-viral expression vectors are used to introduce two or more kinds of genes, all kinds of non-viral expression vectors can be concurrently introduced into a somatic cell; this represents a preferred embodiment of the present invention.

In the method of the present invention, as genes that encode reprogramming factors, for example, a combination of four kinds of genes consisting of an Oct family gene, a Klf family gene, a Sox family gene, and a Myc family gene can be used. A combination of three kinds of genes consisting of an Oct family gene, a Klf family gene, and a Sox family gene, or a combination of two kinds of genes selected from among the aforementioned three kinds of genes can also be used.

In the method of the present invention, it is preferable that the above-described four kinds, three kinds, or two kinds of genes be concurrently introduced into a somatic cell. To introduce the above-described four kinds, three kinds, or two kinds of genes, one kind of non-viral expression vector incorporating all these genes may be used. Alternatively, several kinds of non-viral expression vectors may be used in combination as appropriate, so as to cover all the combinations of these genes. When several kinds of non-viral expression vectors are used, it is preferable that preferably two or three kinds, more preferably two kinds of non-viral expression vectors be used. It is preferable that these non-viral expression vectors be concurrently introduced into a somatic cell.

If the number of genes introduced exceeds four kinds, several kinds of non-viral expression vectors may be combined as appropriate, so as to cover all the combinations of these genes. When several kinds of non-viral expression vectors are used, it is preferable that preferably two to five kinds, more preferably two to four kinds, more preferably three or four of non-viral expression vectors be used. These non-viral expression vectors are preferably concurrently introduced into a somatic cell.

An example of a preferable method is a method wherein one non-viral expression vector harboring an Oct family gene, a Klf family gene, and a Sox family gene, and one non-viral expression vector harboring a Myc family gene are introduced into a somatic cell concurrently or at different times; in this method, it is preferable that the two kinds of non-viral expression vectors be concurrently introduced into the somatic cell. In another preferred embodiment, it is also possible to use a method wherein one non-viral expression vector harboring an Oct family gene, a Klf family gene, a Sox family gene, and a Myc family gene is introduced into a somatic cell.

In a preferred embodiment of the present invention, in a combination of four kinds of genes consisting of an Oct3/4, Klf4, Sox2, and c-Myc, or an optionally chosen combination of three kinds or two kinds selected from among these four kinds of genes, preferably the combination or three kinds or two kinds of genes, wherein said combination does not contain c-Myc, can be used. This preferred embodiment is hereinafter described specifically, to which the scope of the present invention is never limited.

(a1) A method wherein one kind of non-viral expression vector, more preferably a plasmid vector, harboring Oct3/4, Klf4, Sox2 and c-Myc, is introduced into a somatic cell.

(b1) A method wherein a first non-viral expression vector, more preferably a plasmid vector, harboring two kinds of genes selected from among Oct3/4, Klf4, Sox2 and c-Myc, and a second non-viral expression vector, more preferably a plasmid vector, harboring the remaining two kinds of genes selected from among Oct3/4, Klf4, Sox2 and c-Myc, are introduced into a somatic cell. Preferably, the first non-viral expression vector and the second non-viral expression vector can be concurrently introduced into a somatic cell.

(c1) A method wherein a first non-viral expression vector, more preferably a plasmid vector, harboring three kinds of genes selected from among Oct3/4, Klf4, Sox2 and c-Myc, and a second non-viral expression vector, more a preferably a plasmid vector, harboring the remaining one kind of gene selected from among Oct3/4, Klf4, Sox2 and c-Myc, are introduced into a somatic cell. Preferably, the first non-viral expression vector and the second non-viral expression vector can be concurrently introduced into a somatic cell.

(d1) A method wherein a first non-viral expression vector, more preferably a plasmid vector, harboring two kinds of genes selected from among Oct3/4, Klf4 and Sox2, and a second non-viral expression vector, more preferably a plasmid vector, harboring the remaining one kind of gene selected from among Oct3/4, Klf4 and Sox2, and c-Myc, are introduced into a somatic cell. Preferably, the first non-viral expression vector and the second non-viral expression vector can be concurrently introduced into a somatic cell.

(e1) A method wherein a first non-viral expression vector, more preferably a plasmid vector, harboring Oct3/4, Klf4 and Sox2, and a second non-viral expression vector, more preferably a plasmid vector, harboring c-Myc, are introduced into a somatic cell. Preferably, the first non-viral expression vector and the second non-viral expression vector can be concurrently introduced into a somatic cell.

(f1) A method wherein a first non-viral expression vector, more preferably a plasmid vector, harboring two kinds of genes selected from among Oct3/4, Klf4 and Sox2 in this order in the orientation from the 5' to 3' end, and a second non-viral expression vector, more preferably a plasmid vector, harboring c-Myc and any one gene out of Oct3/4, Klf4 and Sox2 not contained in the first non-viral expression vector, are introduced into a somatic cell. More specifically, a first non-viral expression vector, preferably a plasmid vector, harboring (i) Oct3/4 and Klf4, (ii) Klf4 and Sox2, or (iii) Oct3/4 and Sox2 in this order in the orientation from the 5' to 3' end can be used; the first non-viral expression vector and the second non-viral expression vector can be concurrently introduced into a somatic cell.

(g1) A method wherein a first non-viral expression vector, more preferably a plasmid vector, harboring Oct3/4, Klf4 and Sox2 in this order in the orientation from the 5' to 3' end, and a second non-viral expression vector, more preferably a plasmid vector, harboring c-Myc are introduced into a somatic cell. Preferably, the first non-viral expression vector and the second non-viral expression vector can be concurrently introduced into a somatic cell.

The method of (f1) or (g1) can be preferably used when the somatic cell is derived from mouse.

In (b1) to (f2) above, for either one of the first non-viral expression vector and the second non-viral expression vector, a viral vector (e.g., retroviral vector, lentiviral vector, adenoviral vector, adeno-associated viral vector, Sendai viral vector or the like) can be used in place of the non-viral expression vector.

In another preferred embodiment of the present invention, in (a1) to (f2) above, L-Myc can be used in place of c-Myc.

In still another preferred embodiment, a combination of three kinds of genes consisting of Oct3/4, Klf4 and Sox2 can be used. This preferred embodiment is hereinafter described specifically, to which the scope of the present invention is never limited.

(a2) A method wherein one kind of non-viral expression vector, more preferably a plasmid vector, harboring Oct3/4, Klf4 and Sox2, is introduced into a somatic cell.

(b2) A method wherein one kind of non-viral expression vector, more preferably a plasmid vector, harboring Oct3/4, Klf4 and Sox2 in this order in the orientation from the 5' to 3' end are introduced into a somatic cell.

(c2) A method wherein a first non-viral expression vector, more preferably a plasmid vector, harboring two kinds of genes selected from among Oct3/4, Klf4 and Sox2, and a second non-viral expression vector, more preferably a plasmid vector, harboring the remaining one kind of gene selected from among Oct3/4, Klf4 and Sox2, are introduced into a somatic cell. Preferably, the first non-viral expression vector and the second non-viral expression vector can be concurrently introduced into a somatic cell.

(d2) A method wherein a first non-viral expression vector; more preferably a plasmid vector, harboring two kinds of genes selected from among Oct3/4, Klf4 and Sox2 in this order in the orientation from the 5' to 3' end, and a second non-viral expression vector, more preferably a plasmid vector, harboring any one gene out of Oct3/4, Klf4 and Sox2 not contained in the first non-viral expression vector are introduced into a somatic cell. More specifically, a first non-viral expression vector, preferably a plasmid vector, harboring (i) Oct3/4 and Klf4, (ii) Klf4 and Sox2, or (iii) Oct3/4 and Sox2 in this order in the orientation from the 5' to 3' end can be used, and the first non-viral expression vector and the second non-viral expression vector can be concurrently introduced into a somatic cell.

The method of (b2) or (d2) can be preferably used when the somatic cell is derived from mouse.

In (c2) or (d2) above, for either one of the first non-viral expression vector and the second non-viral expression vector, a viral vector (e.g., retroviral vector, lentiviral vector, adenoviral vector, adeno-associated viral vector, Sendai viral vector or the like) can also be used in place of the non-viral vector.

In still another preferred embodiment of the present invention, a combination of two kinds of genes selected from among Oct3/4, Klf4 and Sox2 can be used. This preferred embodiment is hereinafter described specifically, to which the scope of the present invention is never limited.

(a3) A method wherein one kind of non-viral expression vector, more preferably a plasmid vector, harboring two kinds of genes selected from among Oct3/4, Klf4 and Sox2, is introduced into a somatic cell.

(b3) A method wherein one kind of non-viral expression vector, more preferably a plasmid vector, harboring (i) Oct3/4 and Klf4, (ii) Klf4 and Sox2, or (iii) Oct3/4 and Sox2 in this order in the orientation from the 5' to 3' end, is introduced into a somatic cell.

(c3) A method wherein a first non-viral expression vector, more preferably a plasmid vector, harboring one kind of gene selected from among Oct3/4, Klf4 and Sox2, and a second non-viral expression vector, more preferably a plasmid vector, harboring any one gene out of Oct3/4, Klf4 and Sox2 not contained in the first non-viral expression vector, are introduced into a somatic cell. Preferably, the first non-viral expression vector and the second non-viral expression vector can be concurrently introduced into a somatic cell.

The method of (b3) can be preferably used when the somatic cell is derived from mouse.

In (c3) above, for either one of the first non-viral expression vector and the second non-viral expression vector, a viral vector (e.g., retroviral vector, lentiviral vector, adenoviral vector, adeno-associated viral vector, Sendai viral vector or the like) can be used in place of the non-viral vector.

In still another preferred embodiment of the present invention, a combination of six kinds of genes selected from among Oct3/4, Klf4, Sox2, c-Myc, Lin28 and Nanog can be used. This preferred embodiment is hereinafter described specifically, to which the scope of the present invention is never limited.

(a4) A method wherein a first non-viral expression vector, more preferably a plasmid vector, harboring two kinds of genes selected from among Oct3/4, Klf4 and Sox2, a second non-viral expression vector, more preferably a plasmid vector, harboring the remaining one kind of gene selected from among Oct3/4, Klf4 and Sox2, and a third non-viral expression vector, more preferably a plasmid vector, harboring c-Myc, Lin28 and Nanog genes are introduced into a somatic cell. Preferably, the first, second and third non-viral expression vectors can be concurrently introduced into a somatic cell.

(b4) A method wherein a first non-viral expression vector, more preferably a plasmid vector, harboring (i) Oct3/4 and Klf4, (ii) Klf4 and Sox2, (iii) Oct3/4 and Sox2 or (iv) Sox2 and Klf4 in this order in the orientation from the 5' to 3' end, a second non-viral expression vector, more preferably a plasmid vector, harboring the remaining one kind of gene selected from among Oct3/4, Klf4 and Sox2, and a third non-viral expression vector, more preferably a plasmid vector, harboring c-Myc, Lin28 and Nanog genes in this order in the orientation from the 5' to 3' end are introduced into a somatic cell.

When a gene encoding a factor that induces cell immortalization, such as TERT, SV40 large T antigen, HPV16 E6, HPV16 E7 or Bmi1, is further combined with the two, three, four or six genes mentioned above, it can be preferably incorporated into another non-viral expression vector.

In the context above, when a plurality of genes (e.g. Oct family gene, Klf family gene, and Sox family gene) are incorporated in one kind of non-viral expression vector, these genes can preferably be inserted into the non-viral expression vector with an intervening sequence enabling polycistronic expression. By using an intervening sequence enabling polycistronic expression, it is possible to more efficiently express a plurality of genes incorporated in one kind of non-viral expression vector. Useful sequences enabling polycistronic expression include, for example, the 2A sequence of foot-and-mouth disease virus (SEQ ID NO:61, sometimes referred to as FMDV 2A-self-processing sequence) (PLoS ONE 3, e2532, 2008; Stem Cells 25, 1707, 2007), IRES sequence and the like, preferably the 2A sequence. More specifically, when a non-viral expression vector harboring (i) Oct3/4, Klf4 and Sox2, (ii) Oct3/4 and Klf4, (iii) Klf4 and Sox2, (iv) Oct3/4 and Sox2, (v) Sox2 and Klf4 or (vi) c-Myc, Lin28 and Nanog in this order in the orientation from the 5' to 3' end is constructed, it is preferable to insert the 2A sequence between these genes. Accordingly, the present invention also provides a use of the 2A sequence for preparing a non-viral expression vector for iPS cell induction, harboring two or more kinds of reprogramming factors.

The number of repeats of the manipulation to introduce a non-viral expression vector into a somatic cell is not particularly limited, as far as the effect of the present invention of reprogramming a somatic cell to produce an induced pluripotent stem cell can be accomplished, the transfection can be performed once or more optionally chosen times (e.g., once to 10 times, once to 5 times or the like). When two or more kinds of non-viral expression vectors are introduced into a somatic cell, it is preferable that these all kinds of non-viral expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

When the transfection is repeated twice or more, the time interval is exemplified by, but not limited to, 12 hours to 1 week, preferably 12 hours to 4 days, for example, 1 day to 3 days.

As used herein, the term "induced pluripotent stem cell (iPS cell)" refers to a cell possessing properties similar to that of ES cells, more specifically including undifferentiated cells reprogrammed from somatic cells possessing pluripotency and proliferating (self-renewal) capability. It should be noted, however, that this term must not be construed as limiting in any sense, and must be construed in the broadest sense. A method of preparing an induced pluripotent stem cell by means of hypothetical nuclear reprogramming factors is described in WO2005/80598 (in this publication, the term ES-like cell is used), and a method of isolating an induced pluripotent stem cell is also described specifically. WO2007/69666 discloses specific examples of reprogramming factors and methods of somatic cell reprogramming using the same. Therefore, it is desirable that in embodying the present invention, those skilled in the art refer to these publications.

In addition to the gene that encodes a reprogramming factor, a regulatory sequence required for transcription (e.g., promoter, enhancer, and/or terminator and the like) is preferably operably linked to the gene in the non-viral expression vector.

As the promoter, a DNA sequence exhibiting transcription activity in somatic cells can be used, and the promoter can be chosen as appropriate according to animal species and kind of somatic cell. Examples of useful promoters that can be expressed in mammalian cells include a promoter of the IE (immediate early) gene of cytomegalovirus (human CMV), initial promoter of SV40, promoter of retrovirus, metallothionein promoter, heat shock promoter, SRα promoter and the like. An enhancer of the IE gene of human CMV may be used along with a promoter. A useful promoter is the CAG promoter (comprising cytomegalovirus enhancer, chicken β-actin promoter and β-globin gene polyA signal site).

The non-viral expression vector may incorporate a DNA sequence that allows the autonomous replication of the expression vector in a mammalian somatic cell. An example of the DNA sequence is the SV40 replication origin.

The non-viral expression vector is preferably an expression vector autonomously replicable outside the chromosome, and the non-viral expression vector is preferably one that is not integrated in the chromosome. More preferable examples include plasmid vectors. Examples of the plasmid vector include, but are not limited to, *Escherichia coli*-derived plasmids (ColE-series plasmids such as pBR322, pUC18, pUC19, pUC118, pUC119, and pBluescript, and the like), *Actinomyces*-derived plasmids (pIJ486 and the like), *Bacillus subtilis*-derived plasmids (e.g., pUB110, pSH19 and others), yeast-derived plasmids (YEp13, YEp 24, Ycp50 and the like) and the like, as well as artificial plasmid vectors and the like.

Examples of easily available non-viral expression vectors include, but are not limited to, pCMV6-XL3 (OriGene Technologies Inc.), EGFP-C1 (Clontech), pGBT-9 (Clontech), pcDNAI (FUNAKOSHI), pcDM8 (FUNAKOSHI), pAGE107 (Cytotechnology, 3, 133, 1990), pCDM8 (Nature, 329, 840, 1987), pcDNAI/AmP (Invitrogen), pREP4 (Invitrogen), pAGE103 (J. Blochem., 101, 1307, 1987), pAGE210 and the like.

The non-viral expression vector may incorporate a selectable marker as required. Examples of the selectable marker include genes that are deficient in the host cell, such as the dihydrofolate reductase (DHFR) gene or the *Schizosaccaromyces pombe* TPI gene, and genes for resistance to drugs such as ampicillin, kanamycin, tetracycline, chloramphenicol, neomycin, or hygromycin.

While a non-viral expression vector such as plasmid vector introduced into a somatic cell is typically not integrated into the genome of the cell, under selection pressure for iPS cell induction, increased integration efficiency of non-viral expression vector may be observed due to the necessity of stable expression of reprogramming factors. Accordingly, when the iPS cells of interest are intended to use for regenerative medicine and the like, the non-viral expression vector can preferably contain a sequence enabling the excision of transgenes, such as loxP sequence (Chang et al., STEM CELLS Published Online: 12 Feb. 2009 (doi: 10.1002/stem.39)), piggyback transposon (Kaji et al., Nature advance online publication 1 Mar. 2009 (doi: 10.1038/nature07864); Woltjen et al., Nature advance online publication 1 Mar. 2009 (doi:10.1038/nature07863)) and tetracycline responsive element in promoter region (Tet-OnR & Tet-Off R Gene Expression Systems, Clontech).

A method of ligating a gene that encodes a reprogramming factor, a promoter, an enhancer, and/or a terminator and the like, used in the present invention, in an appropriate order to construct a non-viral expression vector capable of expressing the reprogramming factor in the somatic cell, is obvious to those skilled in the art.

When two or more kinds of genes that encode reprogramming factors are used, the genes may be incorporated in one non-viral expression vector. Alternatively, two or more kinds of non-viral expression vectors incorporating different genes may be used. In the latter case, one non-viral expression vector incorporating two or more kinds of genes and a non-viral expression vector incorporating one or more kind genes different therefrom can be combined as appropriate.

Any method of expression vector introduction into an animal cell available to those skilled in the art can be used to introduce a non-viral expression vector into a somatic cell. Examples of useful methods include the use of a transfection reagent such as the FuGENE 6 transfection reagent (Roche), the use of a microporator, the electroporation method, the calcium phosphate method, the lipofection method, the DEAE-dextran-mediated transfection method, the transfection method, the microinjection method, the cationic lipid-mediated transfection method, and the like. Nucleofection can also be used to introduce a gene. These methods may be used in combination.

In introducing a non-viral expression vector into a somatic cell, the expression vector may be introduced into the somatic cell being cultured on feeder cells, and may be introduced only into the somatic cell. To increase expression vector introduction efficiency, the latter method is sometimes suitable. The feeder cells used may be those for cultivation of embryonic stem cells; for example, primary culture fibroblasts from a 14- to 15-day mouse embryo, STO (fibroblast-derived cell line) and the like, treated with a chemical agent such as mitomycin C or exposed to radiation, and the like can be used.

By culturing a somatic cell incorporating a non-viral expression vector under appropriate conditions, it is possible to allow nuclear reprogramming to progress autonomically, and to produce an induced pluripotent stem cell from the somatic cell. The step of culturing a somatic cell incorporating a non-viral expression vector to obtain an induced pluripotent stem cell can be performed in the same manner as a conventional method using a retrovirus; for example, this can be achieved as described in publications such as Cell, 126, pp. 1-14, 2006; Cell, 131, pp. 1-12, 2007; and Science, 318, pp. 1917-1920, 2007. In producing a human induced pluripotent stem cell, it is sometimes desirable that the cell culture density after expression vector introduction be set at a level lower than that for ordinary animal cell culture. For example, it is preferable to continue the cultivation at a cell density of 10,000 to 100,000 cells, preferably about 50,000 cells per cell culture dish. Any medium can be used for the cultivation, chosen as appropriate by those skilled in the art; for example, in producing a human induced pluripotent stem cell, it is sometimes preferable to use a medium suitable of human ES cell culture. Regarding the choice of medium and culturing conditions, the aforementioned publications serve for references.

The resulting induced pluripotent stem cells can be identified using various markers characteristic of undifferentiated cells; means for this identification are also described in the aforementioned publications specifically and in detail.

Various media allowing the maintenance of undifferentiated state and pluripotency of ES cells or media not allowing the maintenance of these properties are known in the art; by using appropriate media in combination, an induced pluripotent stem cell can be isolated efficiently. The differentiation potential and proliferation potential of the isolated induced pluripotent stem cells are easily confirmable for those skilled in the art by utilizing a method of identification in common use for ES cells. When the resulting induced pluripotent stem cell is proliferated under appropriate conditions, a colony of induced pluripotent stem cells is obtained; it is possible to identify the presence of an induced pluripotent stem cell on the basis of the shape of the colony. For example, it is known that mouse induced pluripotent stem cells form raised colonies, whereas human induced pluripotent stem cells form flat colonies, and the shapes of these colonies are extremely similar to those of mouse ES cell and human ES cell colonies, respectively; therefore, it is possible for those skilled in the art to identify the resulting induced pluripotent stem cell on the basis of the shape of the colony. When reprogramming is performed using a somatic cell having a gene incorporating a marker gene such as GFP downstream of a promoter of gene specifically expressing in ES cells, it is possible to identify an induced pluripotent stem cell if the cell becomes positive for the marker (GFP).

"Somatic cells" to be reprogrammed by the method of the present invention refers to any cells except totipotent and pluripotent cells such as early embryos and ES cells, and the choice thereof is not limited. For example, as well as somatic cells in the fetal stage, neonatal somatic cells and mature somatic cells may be used. Preferably, somatic cells derived from mammals, including humans, are used; more preferably human- or mouse-derived somatic cells are used. Specifically, (1) tissue stem cells (somatic stem cells) such as nerve stem cells, hematopoietic stem cells, mesenchymal stem cells, and dental pulp stem cells, (2) tissue progenitor cells, or (3) differentiated cells such as lymphocytes, epithelial cells, muscle cells, fibroblasts (dermal cells and the like), hair cells, liver cells, and gastromucosal cells can be mentioned. When an induced pluripotent stem cell is used to treat a disease, it is desirable to use somatic cells separated from a patient to be treated or from another person sharing the same type of HLA as that of the patient; for example, somatic cells involved in disease and somatic cells involved in disease treatment and the like can be used.

In the present invention, to increase the efficiency of induced pluripotent stem cell establishment, in addition to the introduction of a non-viral expression vector of the present invention, various establishment efficiency improvers may be introduced or added. Examples of iPS cell establishment efficiency improvers include, but are not limited to, histone deacetylase (HDAC) inhibitors [e.g., valproic acid (VPA) (Nat. Biotechnol., 26(7): 795-797 (2008)), low-molecular inhibitors such as trichostatin A, sodium butyrate, MC 1293, and M344, nucleic acid-based expression inhibitors such as siRNA and shRNA against HDAC (e.g., HDAC1 siRNA Smartpool® (Millipore), HuSH 29mer shRNA Constructs against HDAC1 (OriGene) and the like), and the like], G9a histone methyltransferase inhibitors [e.g., low-molecular inhibitors such as BIX-01294 (Cell Stem Cell, 2: 525-528 (2008)), nucleic acid-based expression inhibitors such as siRNA and shRNA against G9a (e.g., G9a siRNA (human) (Santa Cruz Biotechnology) and the like) and the like], L-channel calcium agonist (e.g., Bayk8644) (Cell Stem Cell, 3, 568-574 (2008)), UTF1 (Cell Stem Cell, 3, 475-479 (2008)), Wnt Signaling (e.g., soluble Wnt3a) (Cell Stem Cell, 3, 132-135 (2008)), 2i/LIF (2i is an inhibitor of mitogen-activated protein kinase signaling and glycogen synthase kinase-3; PloS Biology, 6(10), 2237-2247 (2008)), p53 inhibitors (e.g., siRNA and shRNA against p53 (Cell Stem Cell, 3, 475-479 (2008)) and the like. The nucleic acid-based expression inhibitors may be in the form of expression vectors harboring a DNA that encodes siRNA or shRNA. In this case, the DNA that encodes siRNA or shRNA may be inserted into a non-viral expression vector of the present invention, together with reprogramming factors.

The induced pluripotent stem cell produced by the method of the present invention is not subject to limitations concerning the use thereof, and can be used for all types of studies and investigations with the use of ES cells and for the treatment of diseases using ES cells, in place of ES cells. For example, by treating an induced pluripotent stem cell obtained from a somatic cell collected from a patient by the method of the present invention with retinoic acid, a growth factor such as EGF, or glucocorticoid and the like, desired differentiated cells (e.g., nerve cells, myocardial cells, blood cells and the like) can be induced to form an appropriate tissue. By returning the differentiated cell or tissue thus obtained to the patient, stem cell therapy by autologous cell transplantation can be accomplished. It should be noted that the use of an induced pluripotent stem cell of the present invention is not limited to the above-described particular embodiment.

The present invention also provides a non-viral expression vector for use in the above-described method of producing an induced pluripotent stem cell, i.e., a non-viral expression vector (preferably a plasmid vector) incorporating at least one gene that encodes a reprogramming factor. The structure of the vector is as described in detail in the section of a method of producing an induced pluripotent stem cell of the present invention.

An example is a non-viral expression vector incorporating an Oct family gene, a Klf family gene, and a Sox family gene, preferably incorporated in this order in the orientation from the 5' to 3' end. A more preferable example is a non-viral expression vector incorporating these genes with an intervening sequence enabling polycistronic expression, particularly preferably a non-viral expression vector wherein OCT3/4, Klf4 and Sox 2 are incorporated with an intervening sequence enabling polycistronic expression, preferably FMDV 2A-self-processing sequence, in this order in the orientation from the 5' to 3' end.

Since a non-viral expression vector such as plasmid vector introduced into a somatic cell is typically not integrated into the genome of the cell, in a preferred embodiment, the present invention provides an induced pluripotent stem cell wherein transgenes are not integrated into the genome. Since such iPS cell reduces a risk causing tumorigenesis in tissues or organs differentiated therefrom and/or disturbance (e.g., disruption or activation) of an endogenous gene, it can preferably be used for regenerative medicine such as cell transplantation therapy.

However, under selection pressure for iPS cell induction, increased integration efficiency of non-viral expression vector can be observed due to the necessity of stable expression of reprogramming factors. Therefore, in another preferred embodiment, the present invention provides an induced pluripotent stem cell wherein transgenes are integrated into the genome in the form of plasmid. Such iPS cell can reduce a risk causing tumorigenesis in tissues or organs differentiated therefrom as compared to an iPS cell induced by retroviral infection. In addition, the transgenes can be excised from the genome as necessary using a Cre/loxP system (Chang et al., 2009 (supra)) or a piggyback transposon vector and piggyback transposon (Kaji et al., 2009 (supra); Woltjen et al., 2009 (supra)) or tetracycline dependent gene induction. A Cre recombinase or transposase for the excision can be introduced into and expressed in the iPS cell using a plasmid vector or adenoviral vector. In the case of using tetracycline dependent gene induction, Tet-repressor protein or mutated Tet-repressor protein is concomitantly expressed.

EXAMPLES

The present invention is hereinafter described in more detail by means of the following Examples, which, however, are not to be construed as limiting the scope of the invention.

Example 1

Mice having a Nanog reporter were used as an experimental system (Okita et al. Nature, Vol. 448, pp. 313-317, 2007). These mice were prepared by incorporating EGFP and a puromycin resistance gene into the Nanog gene locus of a BAC (bacterial artificial chromosome) purchased from BACPAC Resources. The mouse Nanog gene is expressed specifically in pluripotent cells such as ES cells and early embryos. Mouse iPS cells positive for this reporter have been shown to possess a differentiation potential nearly equivalent to that of ES cells. These Nanog reporter mice were mated with Fbx15 reporter mice (Tokuzawa et al. Mol Cell Biol, Vol. 23, 2699-2708 (2003)), whereby mutant mice having both the Nanog reporter and the Fbx15 reporter were generated.

Figure 2:
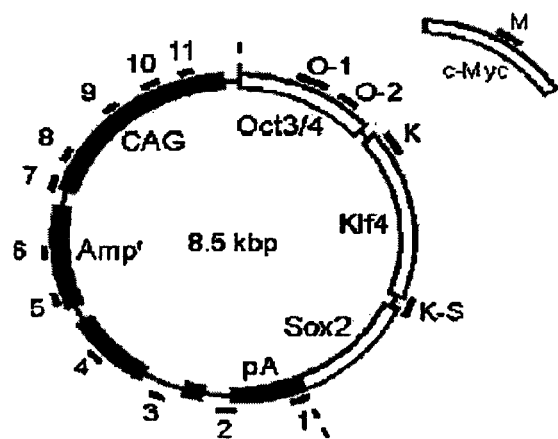
FIG. 2 shows an expression plasmid for iPS cell production. Three kinds of cDNAs that encode Oct3/4, Klf4, and Sox2 were ligated in this order with sequence encoding the 2A peptide as intervening sequence, and inserted into the pCX plasmid (pCX-2A-mOKS). Furthermore, a cDNA of c-Myc was inserted into pCX (pCX-c-Myc). The bald lines show the amplification regions used in the PCR analysis for detecting plasmid integration in the genome (FIG. 6).

The plasmid used for reprogramming was prepared by treating pCX-EGFP (a plasmid supplied by Dr. Masaru Okabe at Osaka University: FEBS Letters, 407, 313-319, 1997) with EcoRI, and inserting a construct wherein the coding regions of Oct3/4, Sox2, and Klf4 (all mouse-derived genes) are ligated via the 2A sequence of foot-and-mouth disease virus in the order of Oct3/4, Klf4, and Sox2, in place of EGFP (pCX-2A-mOKS; FIG. 2). Likewise, a plasmid with the coding region of c-Myc inserted thereinto was prepared (pCX-c-Myc; FIG. 2).

In preparing the construct of the 2A sequence and Oct3/4, Klf4, and Sox2 ligated together, first, sense and antisense oligonucleotides comprising the 2A sequence of foot-and-mouth disease virus (SEQ ID NO:61), upstream restriction endonuclease sites (XbaI and BglII), and downstream restriction endonuclease sites (BspHI, MfeI and PstI), were annealed and inserted into pBluescript II KS (−) vector digested with the XbaI and PstI (pBS-2A). Subsequently, a mouse cDNA that encodes Oct3/4 or Klf4 was amplified by PCR, the translation termination codon was replaced with a BamHI site, and each cDNA was cloned into pCR2.1. Subsequently, the cDNAs of Oct3/4 and Klf4 were ligated with pBS-2A using an appropriate restriction endonuclease to yield pBS-Oct3/4-2A and pBS-Klf4-2A. Subsequently, Klf4-2A was inserted into pBS-Oct3/4-2A in frame using an appropriate restriction endonuclease, whereby pBS-Oct3/4-2A-Klf4-2A was produced. Subsequently, the resulting Oct3/4-2A-Klf4-2A construct was ligated with a cDNA of Sox2 having a translation termination codon in frame, using an appropriate restriction endonuclease. Finally, the resulting Oct3/4-2A-Klf4-2A-Sox2-STOP construct, wherein the 2A sequences and Oct3/4, Klf4, and Sox2 were ligated together, was inserted into the EcoRI site of pCX-EGFP, whereby pCX-2A-mOKS was prepared.

Fibroblasts (MEF) were isolated from the aforementioned mutant mouse fetus (13.5 days after fertilization). Not expressing the Nanog gene, MEF does not express EGFP producing green fluorescence. As such, the MEFs were sown to a 6-well culture plate (Falcon), previously coated with 0.1% gelatin (Sigma), at $1.3 \times 10^5$ cells per well. The culture medium used being DMEM/10% FCS (DMEM (Nacalai Tesque) supplemented with 10% fetal calf serum), the MEFs were cultured at 37° C., 5% $CO_2$. The following day, 4.5 µL of the FuGene6 transfection reagent (Roche) was added in 100 µL of Opti-MEM I Reduced-Serum Medium (Invitrogen), and the medium was allowed to stand at room temperature for 5 minutes. Thereafter, 1.5 µg of an expression vector (pCX-2A-mOKS) was added, and the medium was allowed to stand at room temperature for 15 minutes, after which the medium was added to a MEF culture medium. The following day, the medium was removed, and 1.5 µg of another expression vector (pCX-c-Myc) was introduced with the FuGene6 transfection reagent as described above.

The following day, the culture medium was replaced with a fresh supply (DMEM/10% FCS) and an expression vector (pCX-2A-mOKS) was introduced as described above; the day after, the culture medium was replaced with an ES cell culture medium (DMEM (Nacalai Tesque) supplemented with 15% fetal calf serum, 2 mM L-glutamine (Invitrogen), 100 µM non-essential amino acids (Invitrogen), 100 µM 2-mercaptoethanol (Invitrogen), 50 U/mL penicillin (Invitrogen) and 50 mg/mL streptomycin (Invitrogen)), and an expression vector (pCX-c-Myc) was introduced using the FuGene6 transfection reagent as described above.

The following day, the medium was replaced with an ES cell culture medium. On day 9 after sowing, the MEF culture medium was removed, and the cells were washed by the addition of PBS 2 mL. After the PBS was removed, 0.25% Trypsin/1 mM EDTA (Invitrogen) was added, and the reaction was carried out at 37° C. for about 5 minutes. After cells rose, an ES cell culture medium was added, the cells were suspended, and $1 \times 10^6$ (Exp432A) or $2 \times 10^5$ (Exp432B) cells were sown onto a 100 mm dish with feeder cells sown thereto previously. The feeder cells used were SNL cells that had been treated with mitomycin C to terminate their cell division.

Subsequently, the ES cell culture medium was replaced with a fresh supply every two days until a visible colony emerged; colonization began around day 17, and complete colonization was observed around day 24 (FIG. 1). The time schedule above is summarized in Exp432 in FIGS. 1 and 3.

Figure 4:
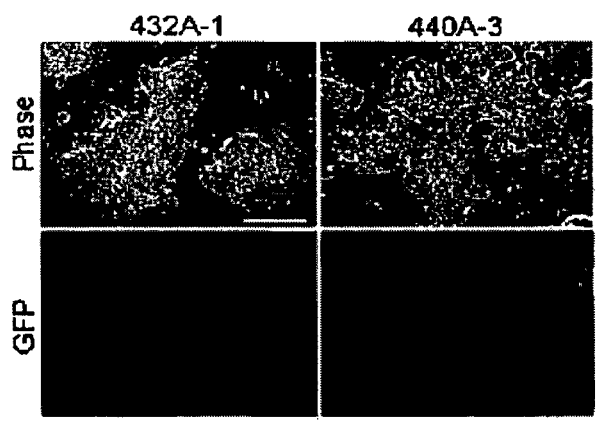
FIG. 4 shows the morphology of non-virus mediated iPS cells established. The upper panels show phase-contrast images, and the lower panels show GFP-positive colonies (scale bar=200 μm).
Figure 5:
FIG. 5 shows results of PCR analysis for the genetic expression of ES cell markers, obtained using total RNAs isolated from ES cells, iPS cells induced using retroviruses (clone 20D-17: Nature, 448, pp. 313-317, 2007), iPS cells induced using plasmids (clones 440A-3, 4, 7, 8, 10 and 11; clone 432A-1), and MEF cells.

The cells obtained became GFP-positive gradually, exhibited a morphology indistinguishable from that of mouse ES cells (432A-1 in FIG. 4), tested positive for various ES cell markers at similar levels as with ES cells (iPS-432A-1 in FIG. 5), and produced adult chimeric mice. Based on the colony shape characteristic of mouse iPS cells and GFP-positive results and results positive for other non-differentiation markers, it was concluded that by introducing the above-described expression vector into MEF cells, nuclear reprogramming was completely advanced to produce an iPS cell, and the iPS cell proliferated and formed the visible colony. Hence, these results showed that an iPS cell could be prepared without using a retrovirus or a lentivirus. PCR analysis detected the integration of the above-described expression vector into the host genome (iPS-432A-1 in FIG. 6).

Example 2

To avoid the integration of pCX-2A-mOKS and pCX-c-Myc into the host genome, the transfection protocol was modified.

Figure 3:
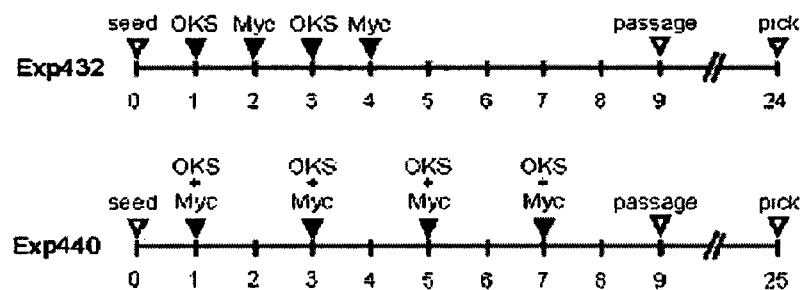
FIG. 3 shows the time schedules for iPS cell induction using plasmids. The solid arrows indicate the time points of transfection of the respective plasmids.
Figure 6:
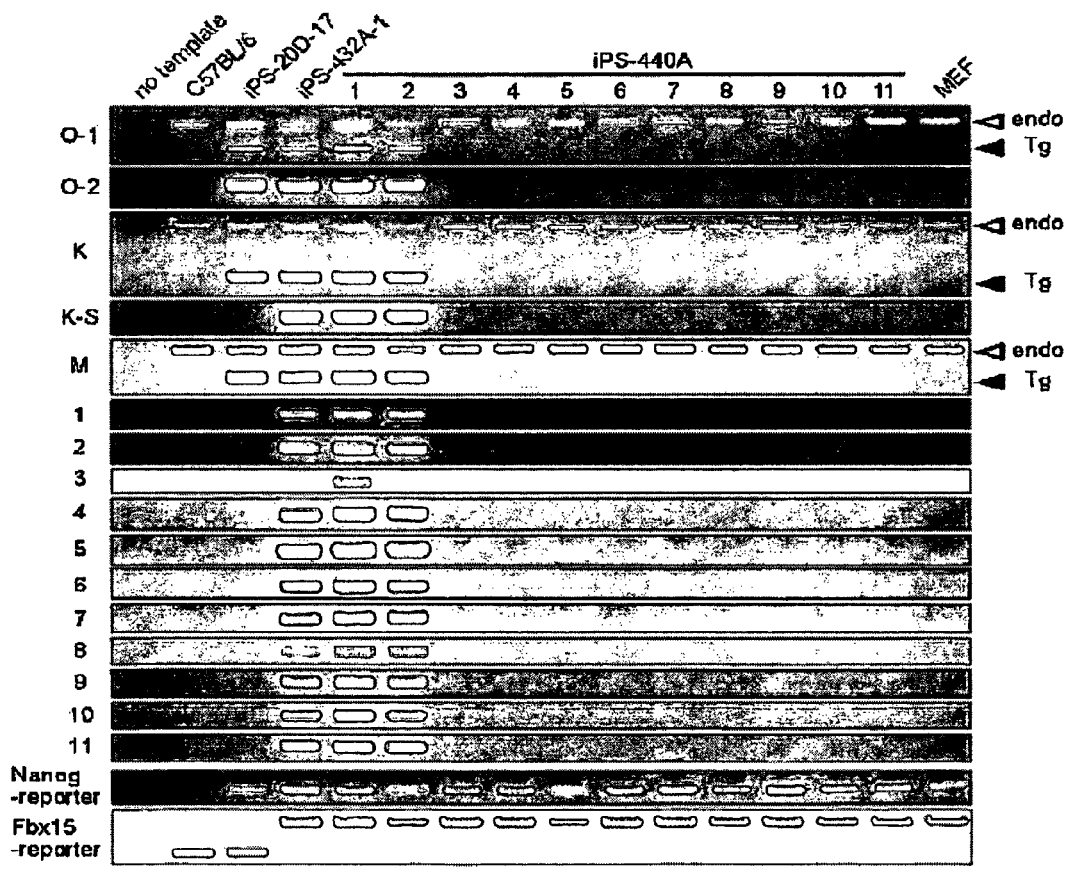
FIG. 6 shows the detection of plasmid integration by PCR. Genomic DNAs were extracted from a C57BL/6 mouse, iPS cell induced using retroviruses (clone 20D-17), iPS cells induced with plasmids (clone 432A-1; clones 440A-1 to 11) and MEF cells, and analyzed by PCR using the primers shown in FIGS. 2, 13 and 14. In the PCR for O-1, K and M, the bands derived from endogenous genes are indicated by the outlined arrowheads, and the bands derived from integrated plasmids are indicated by the solid arrowheads. For the Fbx15 reporter, the lower band indicates wild-type alleles, and the upper band indicates knocked-in alleles.
Figure 11:
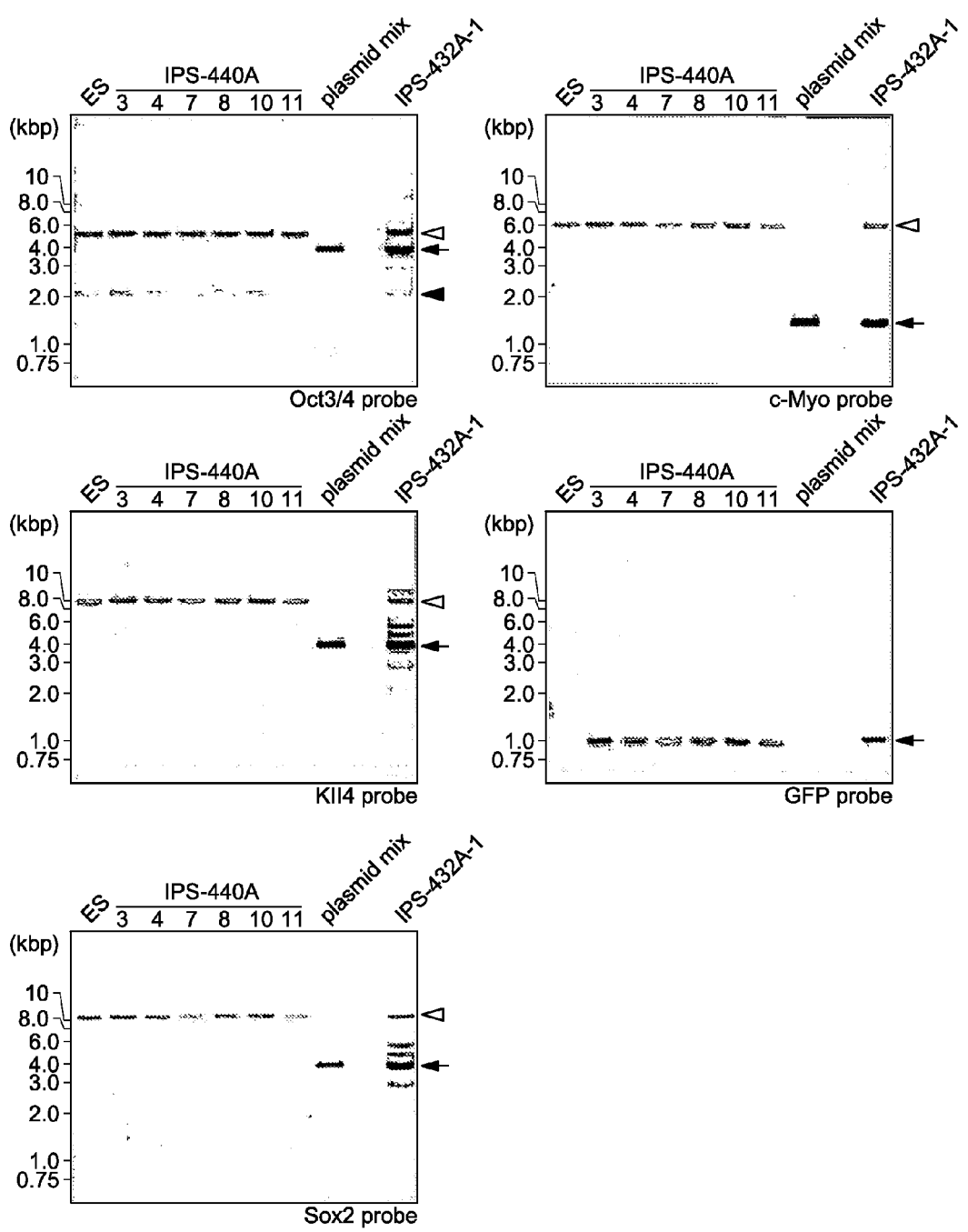
FIG. 11 shows results of Southern blot analysis. Genomic DNAs (6 μg) were extracted from RF8 ES cells and iPS cells (clones 440A-3, 4, 7, 8, 10, and 11; clone 432A-1), and cleaved with BamHI and EcoRI. A mixture of the pCX-2A-mOKS and pCX-c-Myc plasmids (each 20 pg) served for control. The outlined arrowheads indicate the bands derived from endogenous genes, and the solid arrowhead indicates the band derived from the Oct3/4 pseudogene (estimated size 2049 bp) on chromosome 3. The arrows indicate the bands derived from transgenes. Although the identities of the many bands observed in clone 432A-1 are unclear, this may suggest the integration of multiple transgenes. The GFP probe was used to detect Nanog reporter alleles.

On days 1, 3, 5, and 7 after the start of the experiment, pCX-2A-mOKS and pCX-c-Myc were transfected together (Exp440 in FIG. 3). As a result, many GFP-positive colonies were obtained, and cells morphologically indistinguishable from ES cells were produced (440A-3 in FIG. 4). The cells obtained expressed the ES cell markers at the same level as with ES cells (iPS-440A in FIG. 5). To examine for the integration of the plasmid DNA into the genome, 16 sets of PCR primers capable of amplifying each portion of the plasmid were designed (FIGS. 2, 13 and 14). In 9 of the 11 GFP-positive clones obtained by the modified protocol, no amplification of an exogenous DNA was observed (FIG. 6). Furthermore, in Southern blot analysis, no integration of an exogenous gene was detected in these clones (FIG. 11). Although the possible presence of a small plasmid fragment cannot be ruled out definitely, the above results showed that these iPS cells did not have the pCX-2A-mOKS and pCX-c-Myc plasmids integrated into the host genome.

Figure 12:
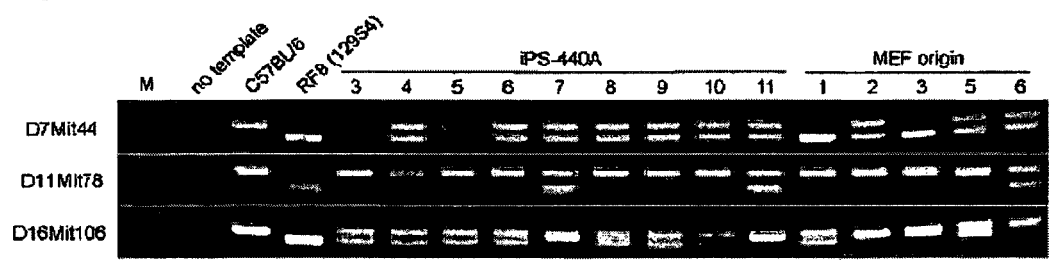
FIG. 12 shows results of SSLP analysis. On genomic DNAs (each 50 ng) from C57BL/6 mouse, RF8 ES cell, iPS cells without integration (clones 440A-3 to 11) and MEF cells, SSLP analysis was performed. These iPS cells derive from a mixture of five MEF cell clones (clones 1, 2, 3, 5, and 6).

To rule out the possibility that the iPS cells without integration are derived from possibly contaminating Nanog-GFP ES cells, SSLP analysis was performed. In Exp440 in FIG. 3, MEF cells from five fetuses were used. In the SSLP analysis, these five fetuses were distinguishable, and the derivations of the iPS cells without integration were identified (FIG. 12). This analysis also showed that the iPS cells without integration differed from the ES cells derived from the 129S4 strain (FIG. 12).

Example 3

Figure 7:
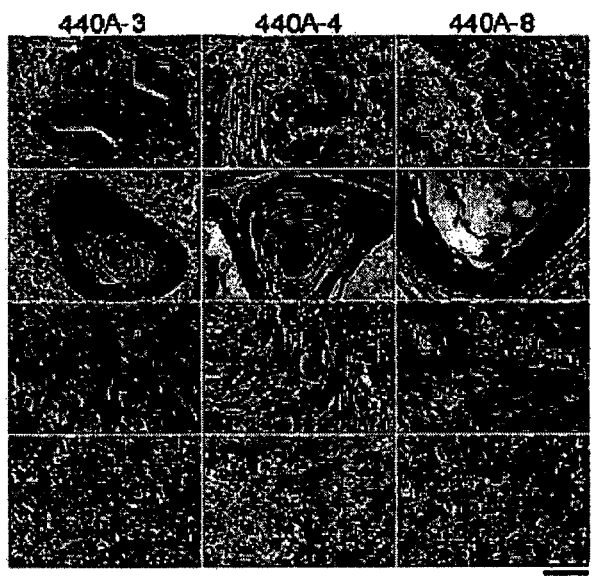
FIG. 7 shows results of teratoma formation. iPS cells without integration of plasmids (clones 440A-3, -4, and -8) were subcutaneously transplanted to nude mice. Four weeks later, tumors were resected and stained with hematoxylin and eosin. Shown from above are the results for gut-like epithelial tissue, epidermal tissue, striated muscles, and nerve tissue, respectively (scale bar=50 μm).
Figure 8:
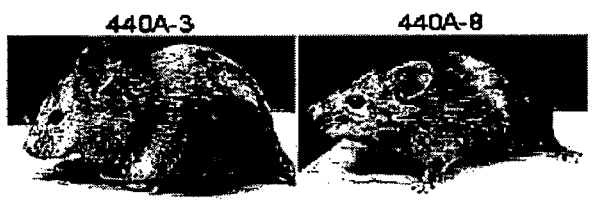
FIG. 8 shows chimeric mice derived from iPS cells without integration (clones 440A-3 and -8).
Figure 9:
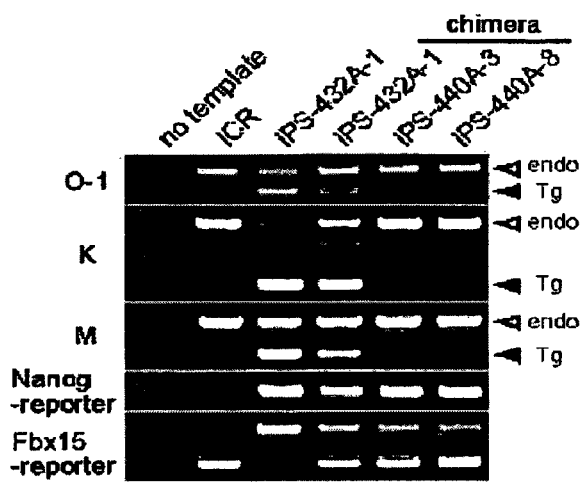
FIG. 9 shows the detection of integration of plasmids by PCR. Genomic DNAs were extracted from an ICR mouse, iPS cell (clone 432A-1), and chimeric mice derived from iPS cells induced using plasmids (clone 432A-1; clones 440A-3, 8), and the O-1, K and M regions shown in FIG. 2 were amplified by PCR. The bands derived from endogenous genes are indicated by the outlined arrowheads, and the bands derived from integrated plasmids are indicated by the solid arrowheads. The presence of the Nanog reporter and Fbx15 reporter was also detected by PCR.
Figure 10:
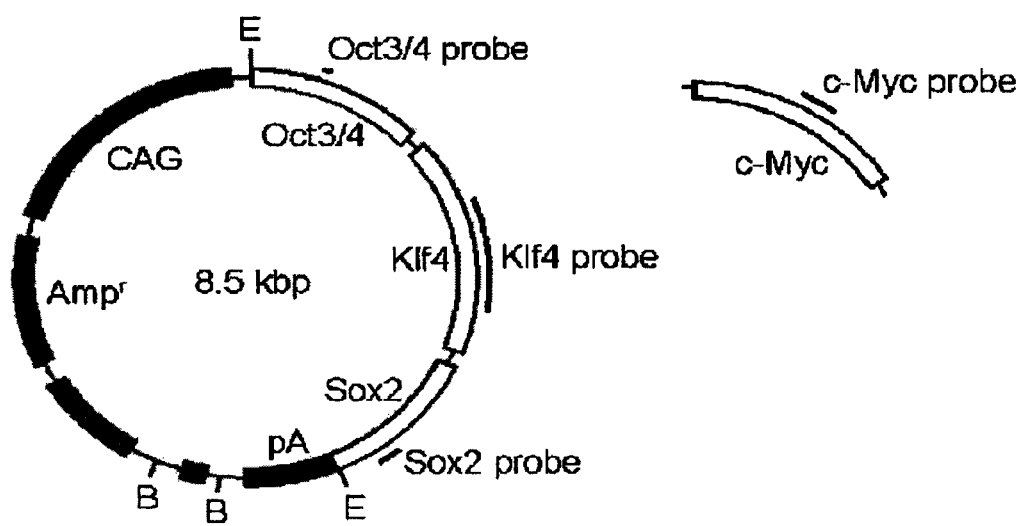
FIG. 10 shows the probes used in Southern blot analysis and the positions of the restriction endonuclease recognition sites. E indicates EcoRI, and B indicates BamHI.

To confirm the pluripotency of iPS cells without integration, iPS cells obtained as described in Example 2 were subcutaneously transplanted to nude mice. All clones tested (440A-3, -4, -8 and -10) produced tumors, which included a broad range of cell types, including cells derived from all the three germ layers (FIG. 7). Furthermore, iPS cells without integration were injected into ICR mouse blastocysts. Judging from the coat colors, adult chimeras were obtained from all clones injected (440A-3, -4, -6, -8, -9 and -10) (FIG. 8). In these chimeric mice, PCR analysis did not detect the integration of any of the transgenes (FIG. 9). The PCR analysis detected both the Nanog and Fbx15 reporters in the chimeras (FIG. 9). Combined with the fact that iPS cells without integration emerged from the double reporter mice, and that the inventor's laboratory does not keep double reporter ES cells, these results showed that the chimeras were derived from iPS cells without integration, rather than from contaminating ES cells. Hence, these results confirmed that the iPS cells without integration possessed pluripotency.

Long-term examination of 71 chimeric mice obtained and offspring thereof showed that in the chimeric mice derived from an iPS cell prepared by introducing 4 genes (Oct3/4, Klf4, Sox2, c-Myc) using a retrovirus, and offspring thereof, compared with normal mice, the mortality rate began to rise earlier, whereas the chimeric mice derived from an iPS cell without integration of the 4 genes and offspring thereof exhibited a survival curve similar to that of normal mice.

When chimeric mice obtained and wild mice were mated, F1 mice were obtained; therefore, it was confirmed that iPS cells without integration contributed to the germline (germline-transmission).

Example 4

Human dental pulp stem cells (clone name; DP31, PCT/JP2008/068320, J. Dent. Res., 87(7):676-681 (2008)) were used as an experimental system. The DP31 was allowed to express the mouse ecotropic virus receptor Slc7a1 gene using a lentivirus as described in Cell, 131, 861-872 (2007). These cells were cultured using the MSCGM bullet kit (Lonza).

The plasmids used for reprogramming were prepared from pCX-EGFP (supplied by Dr. Masaru Okabe at Osaka University, FEBS Letters, 407, 313-319, 1997) in the same manner as Example 1. Specifically, the pCX-EGFP was treated with EcoRI, and a construct with the coding regions of SOX2 and KLF4 ligated via the 2A sequence of foot-and-mouth disease virus therein was inserted in place of EGFP, whereby the plasmid pCX-hSK was prepared. Likewise, a plasmid with c-Myc, Lin28, and Nanog ligated via the 2A sequence (pCX-hMLN) therein, a plasmid with the OCT3/4 coding region inserted therein (pCX-hOCT3/4), and a plasmid with the SV40 Large T antigen inserted therein (pCX-SV40LT) were prepared.

Figure 15:
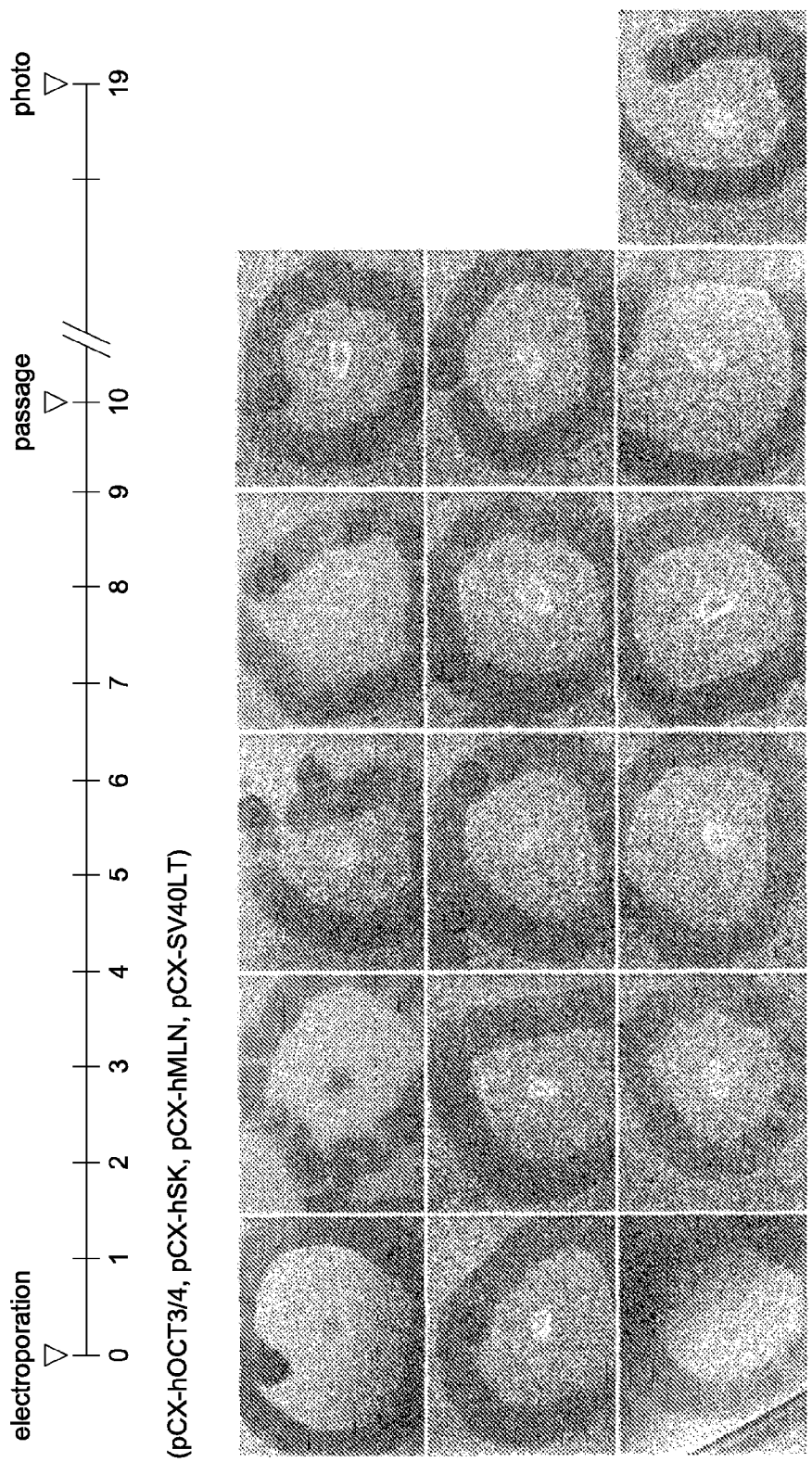
FIG. 15 shows a time course protocol for transfecting human dental pulp stem cells with Oct3/4, Klf4, Sox2, c-Myc, Lin28, Nanog and the SV40 Large T antigen using plasmids according to the method of the present invention, and 16 independent iFS cell colonies.

The DP31 cultured in a 100 mm dish was washed with PBS, 0.25% Trypsin/1 mM EDTA (Invitrogen) was added, and the reaction was carried out at 37° C. for about 5 minutes. After cells rose, MSCGM was added, the cells were suspended, and $6 \times 10^5$ cells were recovered in a 15 mL tube. The cells were centrifuged at 800 rpm for 5 minutes; after the supernatant was removed, and the expression plasmids were introduced using the Human Dermal Fibroblast Nucleofector Kit (Amaxa). The amounts of plasmids used were 0.5 μg for pCX-hOCT3/4, 1.0 μg for pCX-hSK, 1.5 μg for pCX-hMLN, and 0.5 μg for pCX-SV40LT. After the treatment, the cells were sown to a 6-well plate. After being cultured with MSCGM for 10 days, the cells were again washed with PBS, 0.25% Trypsin/1 mM EDTA (Invitrogen) was added, and the reaction was carried out at 37° C. for about 5 minutes. After cells rose, MSCGM was added, the cells were suspended, and $1 \times 10^6$ cells were sown onto a 100 mm dish with feeder cells sown thereto previously. The feeder cells used were SNL cells that had been treated with mitomycin C to terminate their cell division. Thereafter, until a colony began to be observed, the medium was replaced with a fresh supply every two days. The medium used was prepared by mixing equal volumes of a primate ES cell culture medium (ReproCELL) supplemented with MSCGM and bFGF (4 ng/mL), respectively. Colonization began around day 19, confirming the establishment of human iPS cell (FIG. 15).

Figure 16:
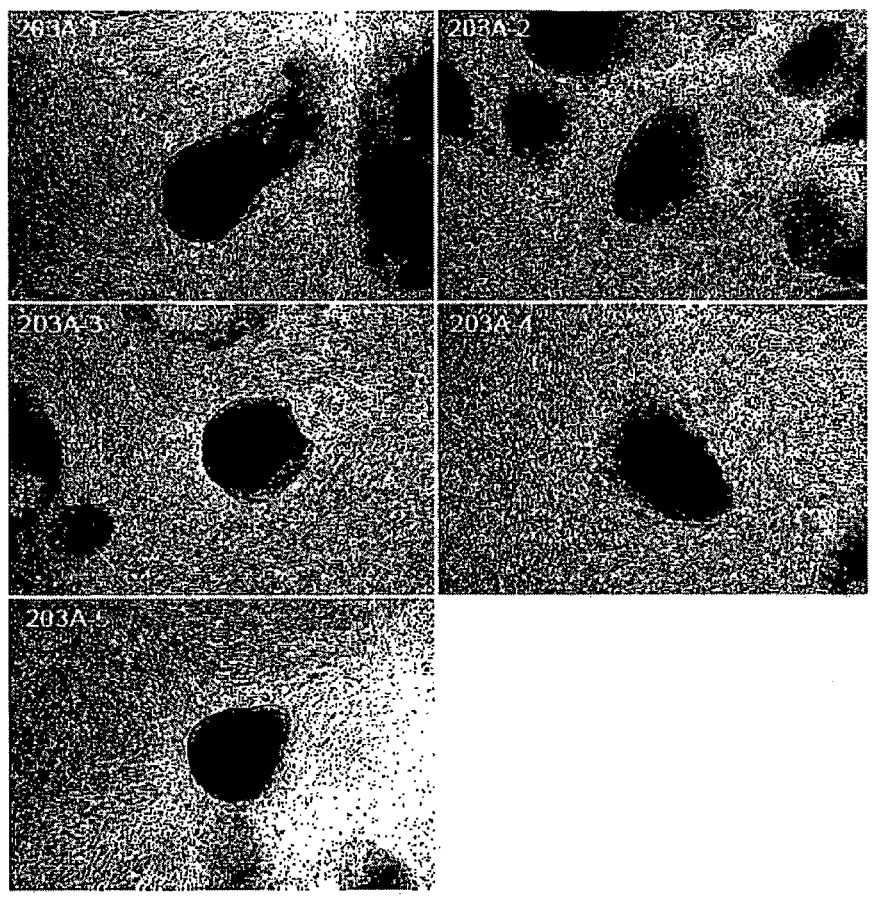
FIGS. 16 and 17 show photographs of iFS cells established from fetal HDF (5 clones: 203A-1 to 203A-5, of which 203A-4 was picked up as a negative control) on day 31 after transfection (FIG. 16) and in the 2nd subculture (FIG. 17).
Figure 17:
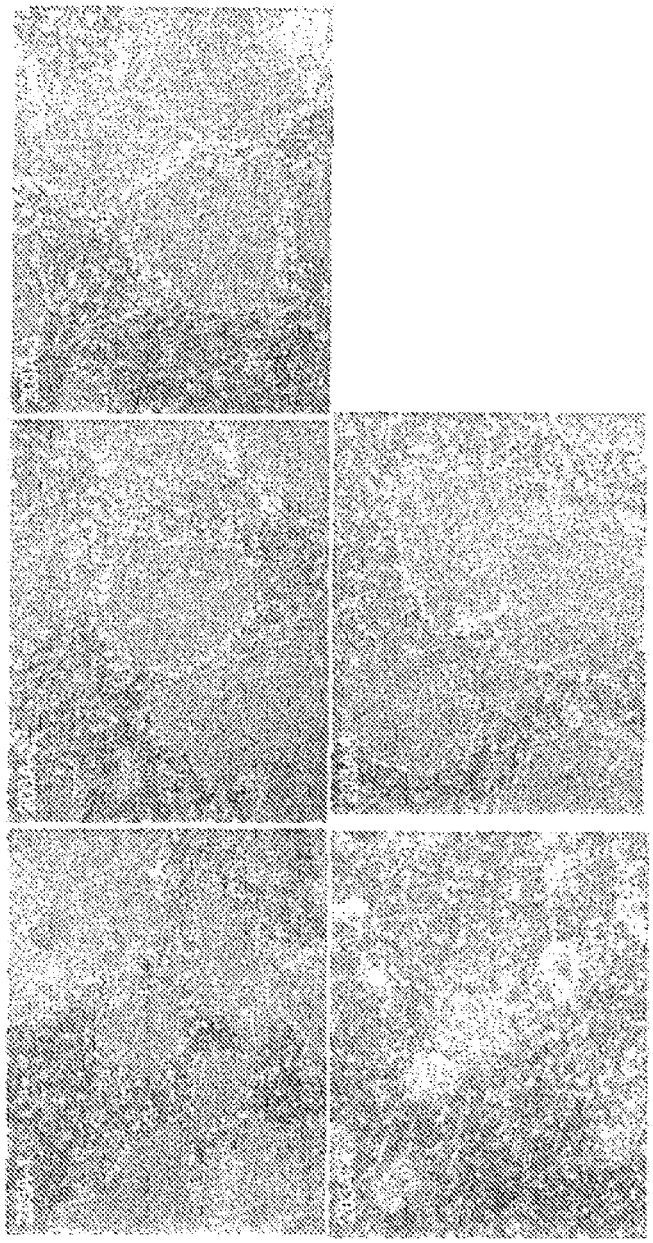

Next, fetal human HDF (Cell applications, INC) was transfected with the same seven kinds of genes as described above. After the transfection, the cells were cultured using a primate ES cell culture medium (ReproCELL) supplemented with 4 ng/ml recombinant human bFGF (WAKO). MSTO cells served as feeder cells. Photographs of cells on day 31 after transfection (5 clones: 203A-1 to 203A-5, of which 203A-4 was picked up as a negative control) are shown in FIG. 16, and photographs of cells in the 2nd subculture are shown in FIG. 17. The 203A-1 to 203A-3 and 203A-5 clones exhibited a typical ES cell-like morphology, confirming the establishment of human iPS cells.

Figure 18:
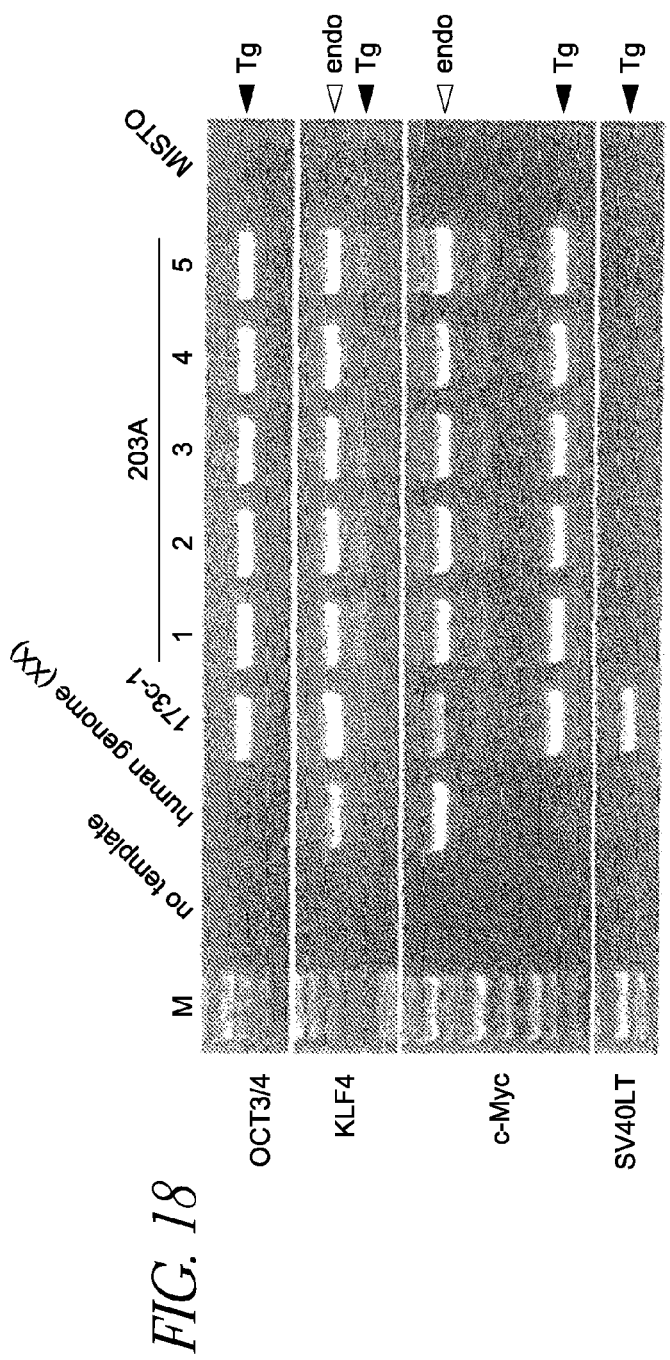
FIG. 18 shows the results of genomic-PCR analysis of 5 iFS cell clones (203A-1 to 203A-5).

These cells were subjected to genomic-PCR analysis, and examined for the integration of the transgenes into the genome. The results are shown in FIG. 18. In all clones, the integration of Oct3/4 (pCX-hOCT3/4) and c-Myc (pCX-hMLN) was detected. The integration of Klf4 (pCX-hSK) was detected in the clones other than 203A-4. The integration of SV40LT (pCX-SV40LT) was not detected in any of the clones.

Example 5

Dental pulp stem cells DP31, used in Example 4, were transfected with six kinds of genes, excluding the SV40

Figure 19:
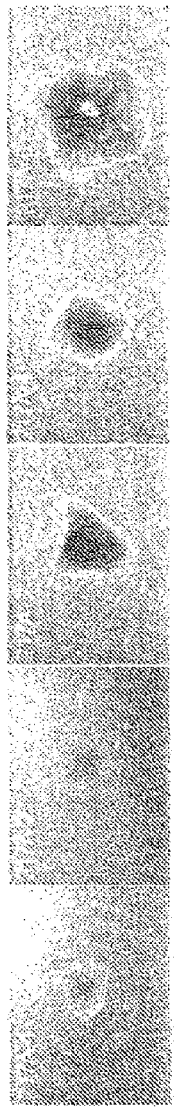
FIGS. 19 and 20 show photographs of iPS cells established from human dental pulp stem cells (5 clones: 217A-1 to -4 and -6) on day 35 after transfection (FIG. 19) and in the 2nd subculture (FIG. 20).
Figure 20:
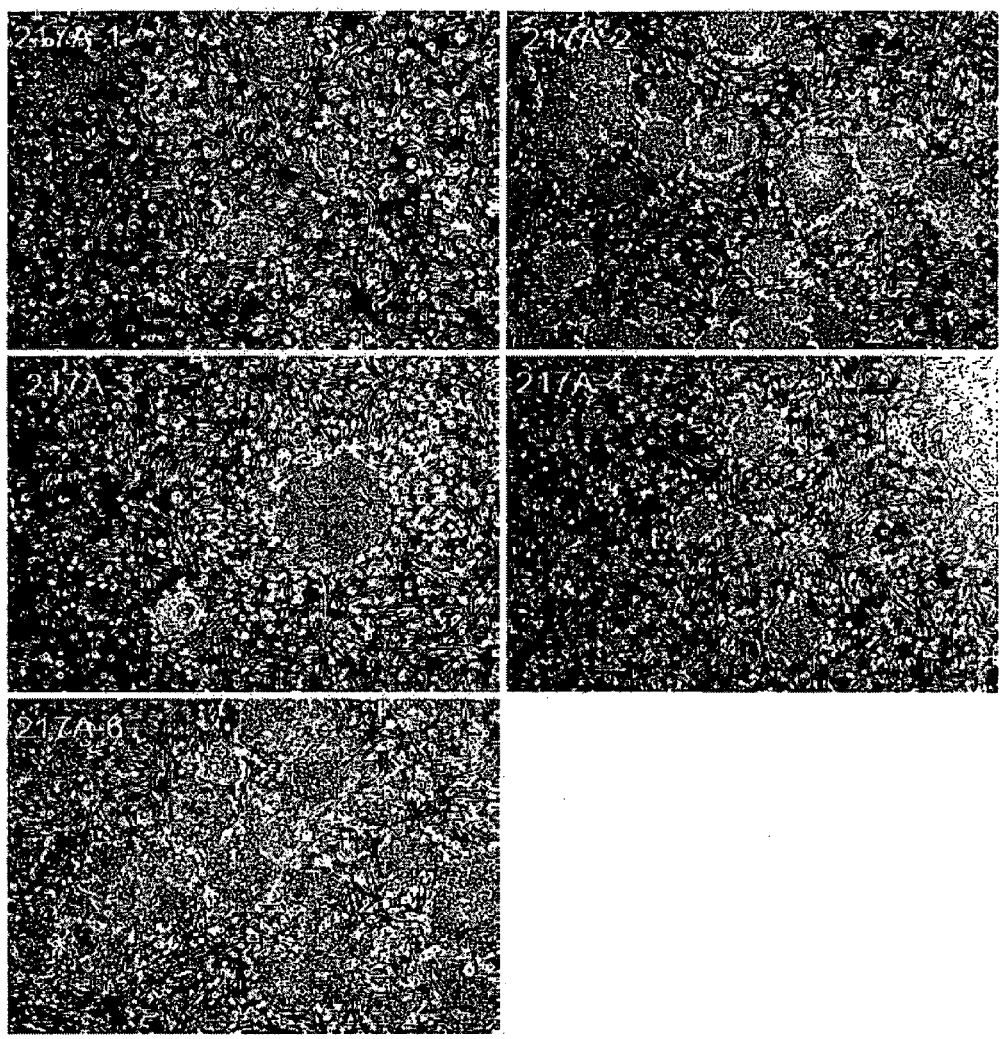

Large T antigen (pCX-hSK, pCX-hMLN, pCX-hOCT3/4), in the same manner as Example 4. Photographs of cells on day 35 after the transfection (5 clones: 217A-1 to -4 and -6) are shown in FIG. 19. Photographs of cells in the 2nd subculture are shown in FIG. 20. All clones exhibited a typical ES cell-like morphology, confirming the establishment of human iPS cells.

Figure 21:
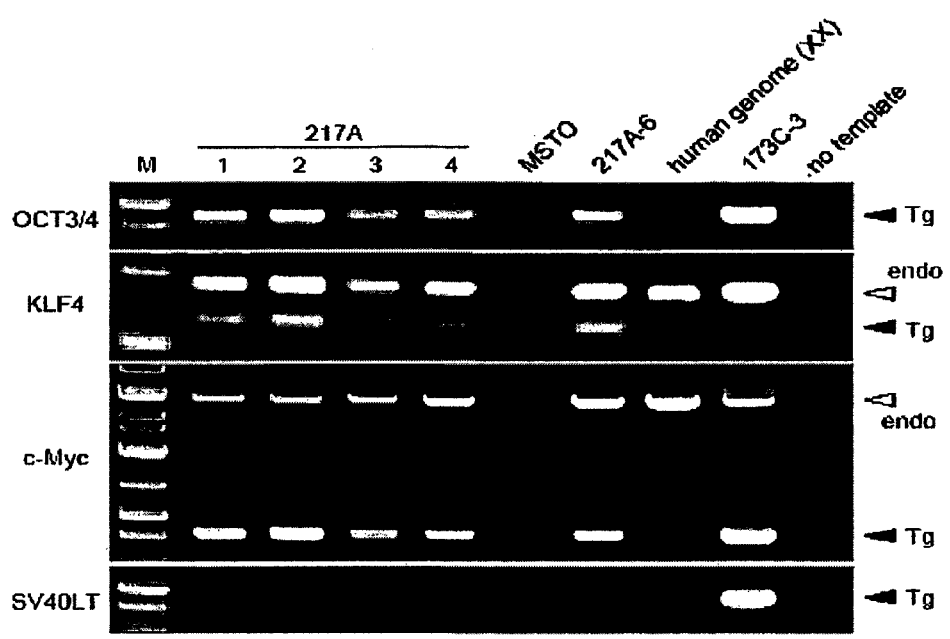
FIG. 21 shows the results of genomic-PCR analysis of 5 iPS cell clones (217A-1 to -4 and -6).

These human iPS cell clones established (217A-1 to 217A-4, 217A-6) were subjected to genomic-PCR analysis. The results are shown in FIG. 21. In all these clones, the integration of the transgenes was demonstrated.

Example 6

An HDF cell line derived from a 6-year-old Japanese female (HDF-120; JCRB) was allowed to express the Slc7a1 gene. The resulting cells (HDF-120-Slc) were transfected with the aforementioned six kinds of genes and an shRNA against p53 (shRNA2: SEQ ID NO:62) (vectors introduced: pCX-hOCT3/4, pCX-hSK, pCX-hMLN-shp53).

Figure 22:
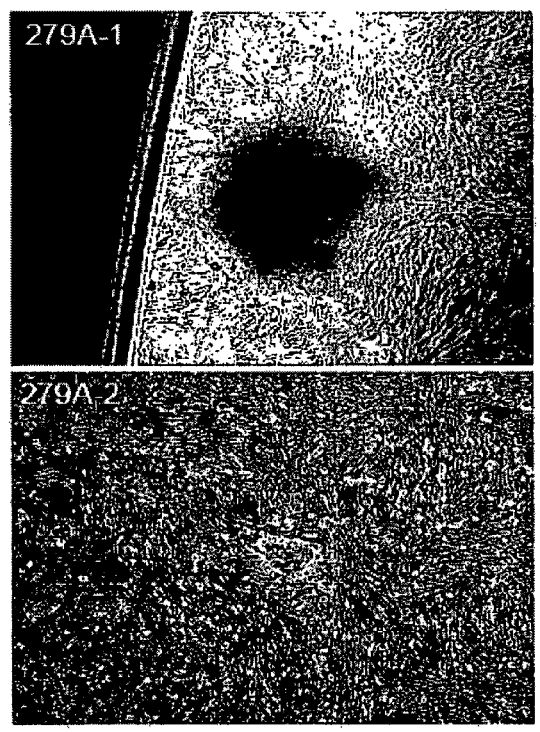
FIGS. 22 and 23 show photographs of iPS cells established from young female HDF (2 clones: 279A-1 and -2) on day 35 after the first electroporation (FIG. 22) and clone 279A-2 after passage culture (FIG. 23; the right panel is a closeup picture of the boxed area in the left panel).
Figure 23:
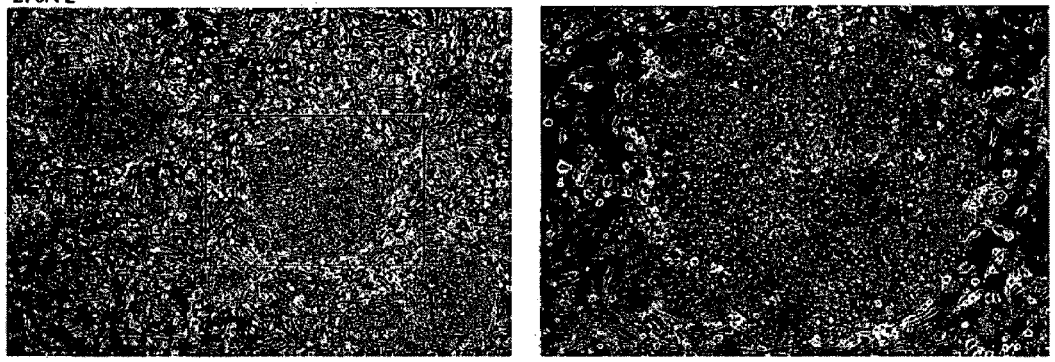
Figure 24:
FIG. 24 shows the results of genomic-PCR analysis of iPS cell clone 279A-2 demonstrating the integration of the transgenes.

Each of pCX-hOCT3/4 (0.5 μg), pCX-hSK (1.0 μg), and pCX-hMLN-shp53 (1.5 μg) was electrically introduced into $6.0 \times 10^5$ cells of HDF-120-Slc using Microporator (100 μL tip, 1600 V, 10 ms, 3 times). Ten days later, each vector was once again electrically introduced under the same conditions, and the cells were sown onto MSTO (100 mm dish). These cells were cultured using DMEM/10% FCS until day 10, thereafter using a primate ES cell culture medium (ReproCELL) supplemented with 4 ng/ml recombinant human bFGF (WAKO). Photographs of cells on day 35 after the first electroporation are shown in FIG. 22. Photographs of cells after passage culture are shown in FIG. 23. A typical ES cell-like morphology was exhibited, confirming the establishment of human iPS cells. Genomic-PCR analysis demonstrated the integration of the transgenes (lane 279A-2 in FIG. 24).

Example 7

Expression vectors separately incorporating the four kinds of genes Oct3/4, Klf4, Sox2 and c-Myc (pCX-Oct4, pCX-Sox2, pCX-Klf4, pCX-c-Myc) were introduced into MEF cells derived from a Nanog reporter mouse (Okita et al. Nature, Vol. 448, pp. 313-317, 2007) per the protocol in Example 2.

Figure 25:
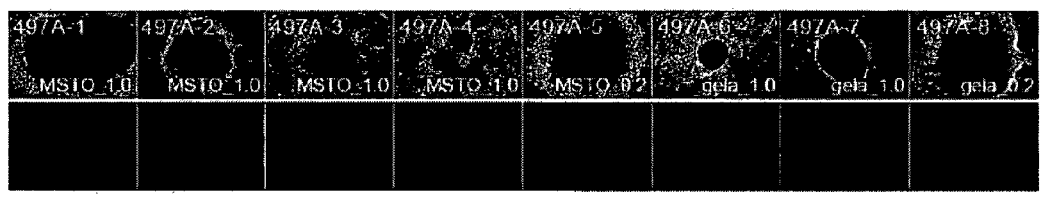
FIG. 25 shows photographs of iPS cells (8 clones: 497A-1 to A-8) after the selection (colonies were selected on day 25 after transfection). The upper panels show phase-contrast images, and the lower panels show GFP-positive colonies.
Figure 26:
FIG. 26 shows the results of genomic-PCR analysis of 5 iPS cell clones (497A-1 to A-5). In 497A-2 and 497A-5, no exogenous gene was not integrated into the genome.

First, the Nanog reporter MEF cells were sown onto a gelatin-coated 6-well plate ($1.3 \times 10^5$ cells/well), and transfected with each of pCX-Oct4 (0.37 μg), pCX-Sox2 (0.36 μg), pCX-Klf4 (0.39 μg), and pCX-c-Myc (0.38 μg) using FuGene6 on days 1, 3, 5, and 7. On day 9, $1 \times 10^6$ cells (1.0) or $0.2 \times 10^6$ cells (0.2) were sown onto MSTO-PH or gelatin (100-mm dish), and colonies were selected on day 25. Photographs of cells after the selection are shown in FIG. 25. A colony shape characteristic of mouse iPS cells and GFP-positive results were obtained, confirming the establishment of mouse iPS cells. The mouse iPS cell clones established (497A-1 to A-5) were subjected to genomic-PCR analysis. The results are shown in FIG. 26. Both 497A-2 and 497A-5 were shown to be iPS cells without integration of any of the exogenous genes.

INDUSTRIAL APPLICABILITY

According to the method of the present invention, it is possible to prepare a highly safe induced pluripotent stem cell from, for example, a patient's somatic cell. The cells obtained by differentiating the induced pluripotent stem cell (e.g., myocardial cells, insulin-producing cells, nerve cells and the like) can be safely used for stem cell transplantation therapy for a broad range of diseases, including heart failure, insulin-dependent diabetes, Parkinson's disease and spinal injury.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "Claims".

The contents disclosed in any publication cited here, including patents and patent applications, are hereby incorporated in their entireties by reference, to the extent that they have been disclosed herein.

This application is based on U.S. provisional patent application Nos. 61/071,508, 61/136,246, 61/136,615 and 61/193,363, the contents of which are hereby incorporated by reference.

What is claimed is:

1. A method of producing an induced pluripotent stem cell, comprising the steps of:
concurrently introducing two or more plasmids into a mammalian somatic cell in vitro, wherein the two or more plasmids encode the following reprogramming factors:
Oct 3/4, Sox 2, Klf4, and a Myc family member selected from the group consisting of c-Myc, N-Myc, L-Myc and T58A mutant of c-Myc,
wherein at least one plasmid vector encodes two or more of the reprogramming factors via an intervening sequence enabling polycistronic expression, and
culturing the mammalian somatic cell in a medium that supports pluripotent stem cells such that iPS cells are obtained, wherein at least a portion of the one or more plasmids are not integrated into a chromosome of the somatic cell.

2. The method of claim 1, wherein the reprogramming factors further comprise one or more factors selected from the group consisting of Lin28, Lin28B, Nanog, TERT, SV40 Large T antigen, HPV16 E6, HPV16 E7, and Bmi1.

3. The method of claim 1, wherein the genes that encode Klf4 and Sox 2 are incorporated in one plasmid with an intervening sequence enabling polycistronic expression.

4. The method of claim 3, wherein the intervening sequence is a 2A sequence derived from foot-and-mouth disease virus.

5. The method of claim 3, wherein the plasmid comprising the genes that encode Klf4 and Sox 2 further comprise the Oct 3/4 gene.

6. The method of claim 1, wherein the genes that encode Sox 2 and Klf4 are incorporated in a first plasmid vector with an intervening sequence enabling polycistronic expression, and the Myc family gene is incorporated in a second plasmid vector.

7. The method of claim 1, wherein the mammalian somatic cell is a human somatic cell.

8. The method of claim 1, wherein the intervening sequence is a 2A sequence derived from foot-and-mouth disease virus.

9. The method of claim 6, wherein the intervening sequence is a 2A sequence derived from foot-and-mouth disease virus.

* * * * *

SEQUENCE LISTING

```
<160> NUMBER OF SEQ ID NOS: 62

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for G3PDH

<400> SEQUENCE: 1
accacagtcc atgccatcac                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for G3PDH
```

<400> SEQUENCE: 2
tccaccaccc tgttgctgta                                              20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for Nanog

<400> SEQUENCE: 3
agggtctgct actgagatgc t                                            21

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for Nanog

<400> SEQUENCE: 4
caacacctgg tttttctgcc accg                                         24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for Rex1

<400> SEQUENCE: 5
acgagtggca gtttcttctt ggga                                         24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for Rex1

<400> SEQUENCE: 6
tatgactcac ttccaggggg cact                                         24

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer for ECAT1

<400> SEQUENCE: 7
tgtggggccc tgaaaggcga gctgagat                                     28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer for ECAT1

-continued

```
<400> SEQUENCE: 8
atgggccgcc atacgacgac gctcaact                                          28

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for ERas

<400> SEQUENCE: 9
actgcccctc atcagactgc tact                                              24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for ERas

<400> SEQUENCE: 10
cactgccttg tactcgggta gctg                                              24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for Fbx15

<400> SEQUENCE: 11
gttggaatct gcttctacag                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for Fbx15

<400> SEQUENCE: 12
cttcaccaag atttccgatg                                                   20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for Esg1

<400> SEQUENCE: 13
gaagtctggt tccttggcag gatg                                              24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for Esg1

<400> SEQUENCE: 14
```
actcgataca ctggcctagc                                          20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for Oct3/4

<400> SEQUENCE: 15
ctgagggcca ggcaggagca cgag                                     24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for Oct3/4

<400> SEQUENCE: 16
ctgtagggag ggcttcgggc actt                                     24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for Sox2

<400> SEQUENCE: 17
ggttacctct tcctcccact ccag                                     24

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for Sox2

<400> SEQUENCE: 18
tcacatgtgc gacaggggca g                                        21

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer for Klf4

<400> SEQUENCE: 19
caccatggac ccgggcgtgg ctgccagaaa                               30

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer for Klf4

<400> SEQUENCE: 20

```
ttaggctgtt cttttccggg gccacga                                              27
```

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for c-Myc

<400> SEQUENCE: 21

```
cagaggagga acgagctgaa gcgc                                                 24
```

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      primer for c-Myc

<400> SEQUENCE: 22

```
ttatgcacca gagtttcgaa gctgttcg                                             28
```

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      primer for O-1

<400> SEQUENCE: 23

```
cggaattcaa ggagctagaa cagtttgcc                                            29
```

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer for O-1

<400> SEQUENCE: 24

```
ctgaaggttc tcattgttgt cg                                                   22
```

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for O-2

<400> SEQUENCE: 25

```
gatcactcac atcgccaatc                                                      20
```

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer for O-2

<400> SEQUENCE: 26

```
ctgggaaagg tgtcctgtag cc                                                   22
```

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer for K

<400> SEQUENCE: 27
gcgggaaggg agaagacact gcgtc                                        25

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for K

<400> SEQUENCE: 28
taggagggcc gggttgttac tgct                                         24

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer for K-S

<400> SEQUENCE: 29
ccttacacat gaagaggcac ttt                                          23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer for K-S

<400> SEQUENCE: 30
cagctccgtc tccatcatgt tat                                          23

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer for M

<400> SEQUENCE: 31
acactccccc aacaccagga cgttt                                        25

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      primer for M

<400> SEQUENCE: 32
gctcgcccaa atcctgtacc tcgtccgat                                    29

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer for M

<400> SEQUENCE: 33
gagatgagcc cgactccgac ctctt                                          25

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer for 1

<400> SEQUENCE: 34
aggtgcaggc tgcctatc                                                  18

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for 1

<400> SEQUENCE: 35
ttagccagaa gtcagatgct c                                              21

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for 2

<400> SEQUENCE: 36
tggcgtaatc atggtcatag                                                20

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer for 2

<400> SEQUENCE: 37
gcaacgcaat taatgtgagt tag                                            23

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for 3

<400> SEQUENCE: 38
ctggatccgc tgcattaatg a                                              21

```
<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer for 3

<400> SEQUENCE: 39
ccgagcgcag cgagtca                                                   17

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for 4

<400> SEQUENCE: 40
gccttatccg gtaactatcg t                                              21

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      primer for 4

<400> SEQUENCE: 41
gcaccgccta catacctc                                                  18

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer for 5

<400> SEQUENCE: 42
agttgcctga ctccccgtcg tg                                             22

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for 5

<400> SEQUENCE: 43
ggagccggtg agcgtgggtc                                                20

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for 6

<400> SEQUENCE: 44
ccgatcgttg tcagaagtaa gttg                                           24

<210> SEQ ID NO 45
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer for 6

<400> SEQUENCE: 45
tcacagaaaa gcatcttacg ga                                              22

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for 7

<400> SEQUENCE: 46
gaaaagtgcc acctggtcga catt                                            24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for 7

<400> SEQUENCE: 47
gggccattta ccgtaagtta tgta                                            24

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer for 8

<400> SEQUENCE: 48
tatcatatgc caagtacgc                                                  19

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer for 8

<400> SEQUENCE: 49
tagatgtact gccaagtagg aa                                              22

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer for 9

<400> SEQUENCE: 50
tctgactgac cgcgttact                                                  19

<210> SEQ ID NO 51
<211> LENGTH: 22
```

<212> TYPE: DNA
<213> ORGANISM: Artificial Sequence
<220> FEATURE:
<223> OTHER INFORMATION: Description of Artificial Sequence: Synthetic
      primer for 9

<400> SEQUENCE: 51
agaaaagaaa cgagccgtca tt                                            22

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for 10

<400> SEQUENCE: 52
gggggctgcg agggaacaa a                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for 10

<400> SEQUENCE: 53
gccgggccgt gctcagcaac t                                             21

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for 11

<400> SEQUENCE: 54
gcgagccgca gccattgcct ttta                                          24

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer for 11

<400> SEQUENCE: 55
cccagatttc ggctccgcca gat                                           23

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      primer for Nanog-reporter

<400> SEQUENCE: 56
tgggatccct atgctactcc gtcgaagttc                                    30

<210> SEQ ID NO 57
<211> LENGTH: 28
<212> TYPE: DNA

```
<213> ORGANISM: Artificial Sequence
<220> FEATURE:
<223> OTHER INFORMATION: Description of Artificial Sequence: Synthetic
      primer for Nanog-reporter

<400> SEQUENCE: 57
ctaggcaaac tgtggggacc aggaagac                                            28

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      primer for Fbx15-reporter

<400> SEQUENCE: 58
tggtccaaca tcttatacac agtaatga                                            28

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      primer for Fbx15-reporter

<400> SEQUENCE: 59
gtggaactcc cttctagccc tctatccc                                            28

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer for Fbx15-reporter

<400> SEQUENCE: 60
aatgggctga ccgcttcctc gtgctt                                              26

<210> SEQ ID NO 61
<211> LENGTH: 81
<212> TYPE: DNA
<213> ORGANISM: Artificial Sequence
<220> FEATURE:
<223> OTHER INFORMATION: Description of Artificial Sequence: Synthetic
      2A sequence

<400> SEQUENCE: 61
aaaattgtcg ctcctgtcaa acaaactctt aactttgatt tactcaaact ggctgggat         60 gtagaaagca atccaggtcc a                                                   81

<210> SEQ ID NO 62
<211> LENGTH: 48
<212> TYPE: DNA
<213> ORGANISM: Artificial Sequence
<220> FEATURE:
<223> OTHER INFORMATION: Description of Artificial Sequence: Synthetic
      shRNA against p53

<400> SEQUENCE: 62
gactccagtg gtaatctact gctcgagcag tagattacca ctggagtc                     48
```